US009206256B2

(12) United States Patent
Gurney et al.

(10) Patent No.: US 9,206,256 B2
(45) Date of Patent: Dec. 8, 2015

(54) DDR1-BINDING AGENTS AND METHODS OF USE THEREOF

(71) Applicant: OncoMed Pharmaceuticals, Inc., Redwood City, CA (US)

(72) Inventors: Austin L. Gurney, San Francisco, CA (US); Edward Thein Htun Van Der Horst, Palo Alto, CA (US); Sanjeev H. Satyal, San Carlos, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 0 days.

(21) Appl. No.: 14/148,669

(22) Filed: Jan. 6, 2014

(65) Prior Publication Data

US 2014/0199312 A1 Jul. 17, 2014

Related U.S. Application Data

(62) Division of application No. 13/058,684, filed as application No. PCT/US2009/053596 on Aug. 12, 2009, now Pat. No. 8,652,843.

(60) Provisional application No. 61/218,259, filed on Jun. 18, 2009, provisional application No. 61/088,286, filed on Aug. 12, 2008.

(51) Int. Cl.

| | |
|---|---|
| ***A61K 39/395*** | (2006.01) |
| ***C07K 16/28*** | (2006.01) |
| ***A61K 45/06*** | (2006.01) |
| *A61K 39/00* | (2006.01) |

(52) U.S. Cl.

CPC ....... *C07K 16/2896* (2013.01); *A61K 39/39558* (2013.01); *A61K 45/06* (2013.01); *C07K 16/2851* (2013.01); *A61K 2039/505* (2013.01); *C07K 2316/96* (2013.01); *C07K 2317/34* (2013.01); *C07K 2317/73* (2013.01); *C07K 2317/732* (2013.01); *C07K 2317/75* (2013.01); *C07K 2317/76* (2013.01); *C07K 2319/30* (2013.01); *C07K 2319/32* (2013.01)

(58) Field of Classification Search

None

See application file for complete search history.

(56) References Cited

U.S. PATENT DOCUMENTS

| | | | | |
|---|---|---|---|---|
| 3,773,919 | A | 11/1973 | Boswell et al. | |
| 4,485,045 | A | 11/1984 | Regen | |
| 4,544,545 | A | 10/1985 | Ryan et al. | |
| 4,588,585 | A | 5/1986 | Mark et al. | |
| 4,676,980 | A | 6/1987 | Segal et al. | |
| 4,816,567 | A | 3/1989 | Cabilly et al. | |
| 4,946,778 | A | 8/1990 | Ladner et al. | |
| 5,013,556 | A | 5/1991 | Woodle et al. | |
| 5,225,539 | A | 7/1993 | Winter | |
| 5,545,806 | A | 8/1996 | Lonberg et al. | |
| 5,545,807 | A | 8/1996 | Surani et al. | |
| 5,569,825 | A | 10/1996 | Lonberg et al. | |
| 5,585,089 | A | 12/1996 | Queen et al. | |
| 5,625,126 | A | 4/1997 | Lonberg et al. | |
| 5,633,425 | A | 5/1997 | Lonberg et al. | |
| 5,641,870 | A | 6/1997 | Rinderknecht et al. | |
| 5,661,016 | A | 8/1997 | Lonberg et al. | |
| 5,693,761 | A | 12/1997 | Queen et al. | |
| 5,693,762 | A | 12/1997 | Queen et al. | |
| 5,709,858 | A * | 1/1998 | Godowski et al. | 424/143.1 |
| 5,731,168 | A | 3/1998 | Carter et al. | |
| 5,750,373 | A | 5/1998 | Garrard et al. | |
| 5,807,706 | A | 9/1998 | Carter et al. | |
| 5,821,333 | A | 10/1998 | Carter et al. | |
| 6,004,528 | A | 12/1999 | Bergstein | |
| 7,642,228 | B2 | 1/2010 | Carter et al. | |
| 7,695,936 | B2 | 4/2010 | Carter et al. | |
| 8,044,259 | B2 | 10/2011 | Clarke et al. | |
| 8,158,757 | B2 | 4/2012 | Gurney et al. | |
| 8,158,758 | B2 | 4/2012 | Gurney | |
| 8,540,989 | B2 | 9/2013 | Gurney et al. | |
| 8,628,774 | B2 | 1/2014 | Gurney et al. | |
| 8,652,843 | B2 | 2/2014 | Gurney et al. | |
| 2004/0029129 | A1 | 2/2004 | Wang et al. | |
| 2005/0118170 | A1 | 6/2005 | Yoshimura | |

(Continued)

FOREIGN PATENT DOCUMENTS

| | | | |
|---|---|---|---|
| EP | 0 979 281 | A2 | 2/2000 |
| WO | WO 98/50431 | A2 | 11/1998 |

(Continued)

OTHER PUBLICATIONS

Al-Hajj, M., et al., "Prospective identification of tumorigenic breast cancer cells," *Proc. Nat'l. Acad. Sci. USA 100*:3983-3988, National Academy of Sciences, United States (2003).

Alves, F., et al., "Distinct structural characteristics of discoidin I subfamily receptor tyrosine kinases and complementary expression in human cancer," *Oncogene 10*:609-618, Nature Publishing Group, United Kingdom (1995).

Aubele, M. and Werner, M., "Heterogeneity in breast cancer and the problem of relevance of findings," *Anal. Cell. Path. 19*:53-58, Elsevier Science Publishers, Netherlands (1999).

Barker, K., et al., "Expression patterns of the novel receptor-like tyrosine kinase, DDR, in human breast tumours," *Oncogene 11*:569-575, Nature Publishing Group, United Kingdom (1995).

(Continued)

*Primary Examiner* — Shulamith H Shafer

(74) *Attorney, Agent, or Firm* — Sterne, Kessler, Goldstein & Fox P.L.L.C.

(57) ABSTRACT

The present invention relates to DDR1 binding agents and methods of using the agents for treating diseases such as cancer. The present invention provides antibodies that specifically bind to an extracellular domain of DDR1 and modulate DDR1 activity. The present invention further provides methods of using agents that modulate the activity of DDR1, such as antibodies that specifically bind DDR1, to reduce the tumorigenicity of tumors comprising cancer stem cells by reducing the frequency or number of cancer stem cells in the tumor. Also described are methods of treating cancer comprising administering a therapeutically effect amount of an agent or antibody of the present invention to a patient having a tumor or cancer.

22 Claims, 7 Drawing Sheets

(56) References Cited

U.S. PATENT DOCUMENTS

Figure 1:
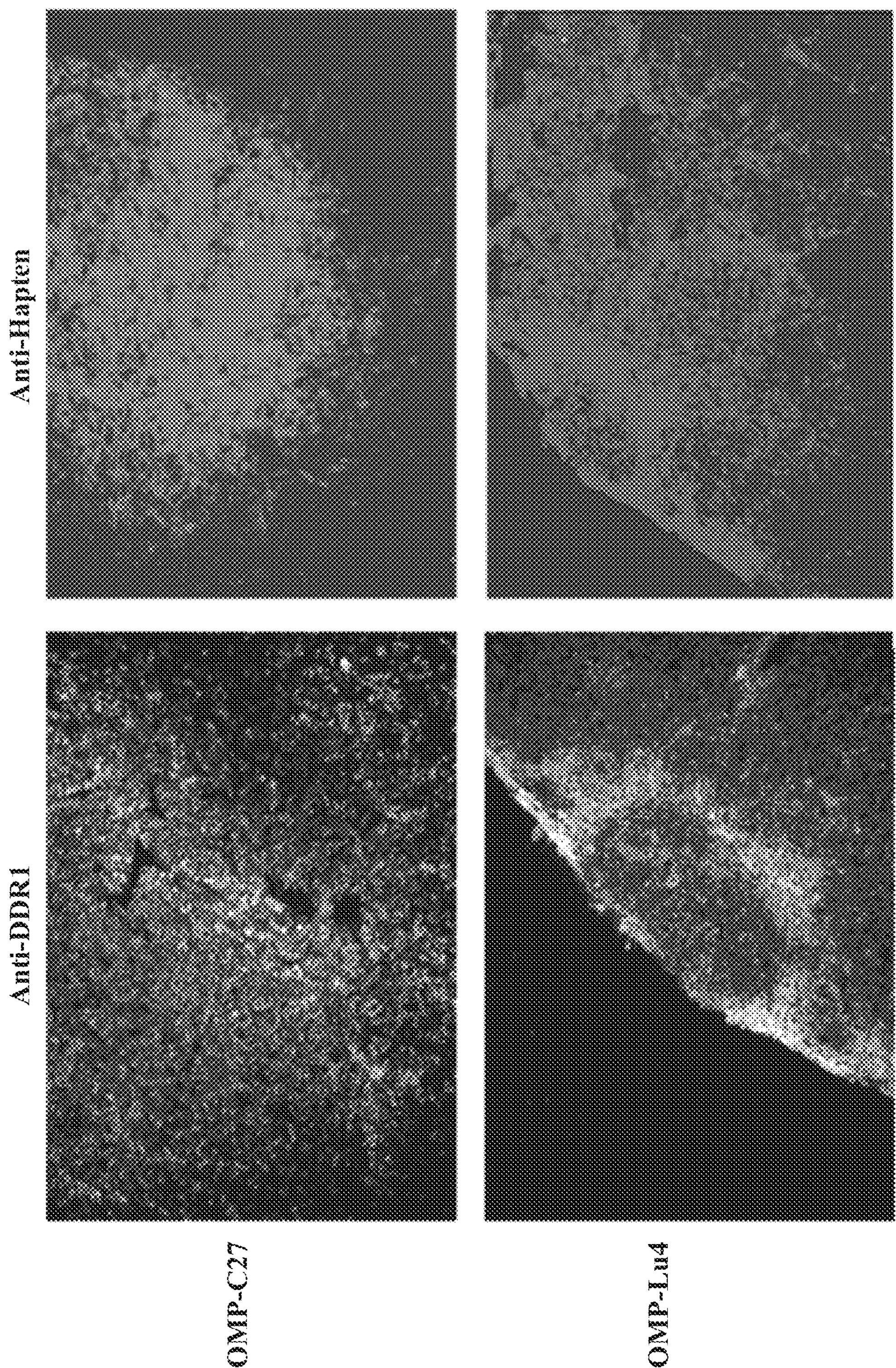

2005/0152899 A1 7/2005 Kinch et al.
2006/0286102 A1 12/2006 Jin et al.
2007/0031438 A1 2/2007 Junghans
2008/0064049 A1 3/2008 Clarke et al.
2008/0171045 A1 7/2008 Lewicki et al.
2008/0178305 A1 7/2008 Clark et al.
2009/0074782 A1 3/2009 Gurney et al.
2010/0286374 A1 11/2010 Kannan et al.
2011/0287011 A1 11/2011 Gurney et al.
2014/0086913 A1 3/2014 Smith et al.
2014/0248282 A1 9/2014 Ono et al.

FOREIGN PATENT DOCUMENTS

WO WO 03/080672 A1 10/2003
WO WO 2004/029094 A1 4/2004
WO WO 2005/000901 A2 1/2005
WO WO 2008/031056 A2 3/2008
WO WO 2008/042236 A2 4/2008

OTHER PUBLICATIONS

Barker, N., et al., "Identification of stem cells in small intestine and colon by marker gene *Lgr5,*" *Nature 449*:1003-1007, Nature Publishing Group, United Kingdom (2007).

Beachy, P., et al., "Tissue repair and stem cell renewal in carcinogenesis," *Nature 432*:324-331, Nature Publishing Group, United Kingdom (2004).

Beerman, H., et al., "Flow cytometric analysis of DNA stemline heterogeneity in primary and metastatic breast cancer," *Cytometry 12*:147-154, Wiley-Liss, Inc., United States (1991).

Boerner, P., et al., "Production of antigen-specific human monoclonal antibodies from in vitro-primed human splenocytes," *J. Immunol. 147*:86-95, American Association of Immunologists, United States (1991).

Bonnet, D. and Dick, J., "Human acute myeloid leukemia is organized as a hierarchy that originates from a primitive hematopoietic cell," *Nat. Med. 3*:730-737, Nature Publishing Company, United States (1997).

Bonsing, B., et al., "Allelotype analysis of flow-sorted breast cancer cells demonstrates genetically related diploid and aneuploid subpopulations in primary tumors and lymph node metastases," *Genes Chromosomes Cancer 82*:173-183, Wiley-Liss, Inc., United States (2000).

Bonsing, B., et al., "High levels of DNA index heterogeneity in advanced breast carcinomas," *Cancer 71*:382-391, American Cancer Society, United States (1993).

Bowie, J., et al., "Deciphering the message in protein sequences: tolerance to amino acid substitutions," *Science 247*:1306-1310, National Academy of Sciences, United States ( 1990).

Brennan, M., et al., "Preparation of Bispecific Aantibodies by Chemical Recombination of Monoclonal Immunoglobulin $G_1$ Fragments," *Science 229*:81-83, American Association for the Advancement of Science, United States (1985).

Clackson, T., et al., "Making antibody fragments using phage display libraries," *Nature 352*:624-628, Nature Publishing Group, United Kingdom (1991).

Cole, S., et al., "The EBV-Hybridoma Technique and Its Application to Human Lung Cancer," *Monoclonal Antibodies and Cancer Therapy 27*:77-96, Alan R. Liss, Inc., United States (1985).

Curat, C., et al., "Mapping of Epitopes in Discoidin Domain Receptor 1 Critical for Collagen Binding," *J. Biol. Chem. 276*:45952-45958, The American Society for Biochemistry and Molecular Biology, Inc., United States (2001).

Dejmek, J., et al., "Wnt-5a and G-protein signaling are required for collagen-induced DDR1 receptor activation and normal mammary cell adhesion," *Int. J. Cancer 103*:344-351, Wiley-Liss, Inc., United States (2003).

Dillman, R., "Antibodies as cytotoxic therapy," *J. Clin. Oncol. 12*:1497, American Society of Clinical Oncology, United States (1994).

Epstein, D., et al., "Biological activity of liposome-encapsulated murine interferon γ is mediated by a cell membrane receptor," *Proc. Natl. Acad. Sci. 82*:3688-3692, National Academy of Sciences, United States (1985).

Evitmova, V., et al., "Identification of genes associated with the invasive status of human mammary carcinoma cell lines by transcriptional profiling," *Tumour Biol. 24*: 189-198, Springer, Netherlands (2003).

Gluzman, Y., "SV40-transformed simian cells support the replication of early SV40 mutants," Cell 23:175-182, Cell Press, United States (1981).

Gruber, M., et al., "Efficient Tumor Cell Lysis Mediated by a Bispecific Single Chain Antibody Expressed in *Escherichia coli," J Immunol. 152*:5368-5374, The American Association of Immunologists, United States (1994).

Guo, A., et al., "Signaling networks assembled by oncogenic EGFR and c-Met.," *Proc. Natl. Acad. Sci. USA 105*:692-697, National Academy of Sciences (2008).

Heinzelmann-Schwarz, V., et al., "Overexpression of the Cell Adhesion Molecules DDR1, Claudin 3, and Ep-CAM in Metaplastic Ovarian Epithelium and Ovarian Cancer," *Clin. Cancer Res. 10*:4427-4436, American Association for Cancer Research, United States (2004).

Hoogenboom, H. and Winter, G., "By-passing Immunisation. Human Antibodies from Synthetic Repertoires of Germline $V_H$ Gene Segments Rearranged in Vitro," *J. Mol. Biol. 227*:381-388, Academic Press Limited, United States (1992).

Hope, K., et al., "Acute myeloid leukemia originates from a hierarchy of leukemic stem cell classes that differ in self-renewal capacity," *Nat. Immunol. 5*:738-743, Nature Publishing Group, United States (2004).

Huse, W., et al., "Generation of a Large Combinatorial Library of the Immunoglobulin Repertoire in Phage Lambda," *Science 246*:1275-1281, American Association for the Advancement of Science, United States (1989).

Hwang, K., et al., "Hepatic uptake and degradation of unilamellar sphingomyelin/cholesterol liposomes: a kinetic study," *Proc. Natl. Acad. Sci. 77*:4030-4034, National Academy of Sciences, United States (1980).

Ichikawa, O., et al., "Structural basis of the collagen-binding mode of discoidin domain receptor 2," *EMBO J.* 26:4168-4176, European Molecular Biology Organization, Germany (2007).

International Search Report for International Application No. PCT/US09/53596, United States Patent and Trademark Office, United States, mailed on Apr. 12, 2010, 6 pages.

Jefferis, R., et al., "IgG-Fc-mediated effector functions: molecular definition of interaction sites for effector ligands and the role of glycosylation," *Immunol. Rev. 163*:59-76, Munksgaard International Publishers, Germany (1998).

Jemal, A., et al., "Cancer Statistics, 2003," *Cancer J. Clin. 53*:5-26, American Cancer Society, United States (2003).

Jones, P., et al., "Replacing the complementarity-determining regions in a human antibody with those from a mouse," *Nature 321*:522-525, Nature Publishing Group, United States (1986).

Köhler, G. and Milstein, C., "Continuous cultures of fused cells secreting antibody of predefined specificity," *Nature 256*:495-497, Nature Publishing Group, United Kingdom (1975).

Kostelny, S., et al., "Formation of a Bispecific Antibody by the Use of Leucine Zippers," *J. Immunol. 148*:1547-1553, The American Association of Immunologists, United States (1992).

Kuukasjrävi, T., et al., "Genetic Heterogeneity and Clonal Evolution Underlying Development of Asynchronous Metastasis in Human Breast Cancer," *Cancer Res. 57*:1597-1604, American Association for Cancer Research, United States (1997).

Labrador, J., et al., "The collagen receptor DDR2 regulates proliferation and its elimination leads to dwarfism," *EMBO Rep. 2*:446-452, European Molecular Biology Organization, United States (2001).

Lapidot, T., et al., "A cell initiating human acute myeloid leukaemia after transplantation into SCID mice," *Nature 17*:645-648, Nature Publishing Group, United States (1994).

(56) References Cited

OTHER PUBLICATIONS

Laval, S., et al., "Isolation and Characterization of an Epithelial-specific Receptor Tyrosine Kinase from an Ovarian Cancer Cell Line," *Cell Growth Differ. 5*:1173-1183, The Association, United States (1994).
Luckow, V. and Summers, M., "Trends in the Development of Baculovirus Expression Vectors," *Nat. Biotechnol. 6*:47-55, Nature Publishing America, United States (1988).
Mark, D., et al., "Site-specific mutagenesis of the human fibroblast interferon gene," *Proc. Natl. Acad. Sci. USA 81*:5662-5066, National Academy of Sciences, Untied States (1984).
Marks, J., et al., "By-passing immunization. Human antibodies from V-gene libraries displayed on phage," *J Mol. Biol. 222*:581-597, Academic Press Limited, United States (1991).
McCafferty, J., et al., "Phage antibodies: filamentous phage displaying antibody variable domains," *Nature 348*:552-554, Nature Publishing Group, United Kingdom (1990).
Mihai, C., et al., "Discoidin domain receptor 2 inhibits fibrillogenesis of collagen type 1," *J. Mol. Biol. 361*:864-876, Academic Press Limited, United States (2006).
Millstein, C. and Cuello, A., "Hybrid hybridomas and their use in immunohistochemistry," *Nature 305*:537-539, Nature Publishing Group, United Kingdom (1983).
Morimoto, K. and Inouye, K., "Single-step purification of $F(ab')_2$ fragments of mouse monoclonal antibodies (immunoglobulins G1) by hydrophobic interaction high performance liquid chromatography using TSKgel Phenyl-5PW," *J. Biochem. Biophys. Methods 24*:107-117, Elsevier Science Publishers B.V., Netherlands (1992).
Morrison, S., et al., "Hematopoietic stem cells: challenges to expectations," *Curr. Opin. Immunol. 9*:216-221, Current Biology Ltd., United Kingdom (1997).
Morrison, S., et al., "Regulatory Mechanisms in Stem Cell Biology," *Cell 88*:287-298, Cell Press, United States (1997).
Morrison, S., et al., "The Biology of Hematopoietic Stem Cells," *Annu. Rev. Cell. Dev. Biol. 11*:35-71, Annual Reviews Inc., United States (1995).
Negoescu, A., et al., "Importance of DNA fragmentation in apoptosis with regard to TUNEL specificity," *Biomed Pharmacother. 52*:252-258, Masson Pub. USA, Inc., United States (1998).
Negoescu, A., et al., "In Situ Apoptotic Cell Labeling by the TUNEL Method: Improvement and Evaluation on Cell Preparations," *J. Histochem Cytochem. 44*:959-968, The Histochemical Society, Inc., United States (1996).
Nemoto, T., et al., "Overexpression of Protein Tyrosine Kinases in Human Esophageal Cancer," *Pathobiol. 65*:165-203, S. Karger A, Basel, Switzerland (1997).
Olaso, E., et al., "DDR2 receptor promotes MMP-2-mediated proliferation and invasion by hepatic stellate cells," *J. Clin. Invest. 108*:1369-1378, American Society for Clinical Investigation, United States (2001).
Pandis, N., et al., "Cytogenetic Comparison of Primary Tumors and Lymph Node Metastase in Breast Cancer Patients," *Genes, Chromosomes Cancer 12*:122-129, Wiley-Liss, Inc., United States (1998).
Park, C., et al., "Mouse Myeloma Tumor Stem Cells: a Primary Cell Culture Assay," *J. Natl. Cancer Inst. 46*:411-422, National Institutes of Health, United States (1971).
Preston, M., et al., "Production and Characterization of a Set of Mouse-Human Chimeric Immunoglobulin G (IgG) Subclass and IgA Monoclonal Antibodies with Identical Variable Regions Specific for *Pseudomonas aeruginosa* Serogroup O6 Lipopolysaccharide," *Infect. Immun. 66*:4137-4142, The American Society for Microbiology, United States (1998).
"Immunoglobulin heavy chain V-D-J region," NCBI FASTA Database Accession No. Q9QXE9, 2006, accessed on Mar. 8, 2010, accessed from http://www.ncbi.nlm.nih.gov/protein/81872711, 2 pages.
Riechmann, L, et al., "Reshaping human antibodies for therapy," *Nature 332*:323-327, Nature Publishing Group, United States (1988).
Shalaby, M., et al., "Development of Humanized Bispecific Antibodies Reactive with Cytotoxic Lymphocytes and Tumor Cells Overexpressing the *HER2* Protooncogene," *J. Exp. Med. 175*:217-225, The Rockefeller University Press, United States (1992).
Sheets, M., et al., "Efficient construction of a large nonimmune phage antibody library: The production of high-affinity human single-chain antibodies to protein antigens," *Proc. Natl. Acad. Sci. USA 95*:6157-6162, National Academy of Sciences, United States (1998).
Shen, C., et al., "Genome-wide Search for Loss of Heterozygosity Using Laser Capture Microdissected Tissue of Breast Carcinoma: An Implication for Mutator Phenotype and Breast Cancer Pathogenesis," *Cancer Res. 60*:3884-3892, American Association for Cancer Research, United States (2000).
Suresh, M., et al, "Bispecific Monoclonal Antibodies from Hybrid Hybridomas," *Methods in Enzymol. 121*:210-228, Academic Press, Inc., United States (1986).
Traunecker, A., et al., "Bispecific single chain molecules (Janusins) target cytotoxic lymphocytes on HIV infected cells," *EMBO J. 10*:3655-3659, Oxford University Press, United Kingdom (1991).
Tutt, A., et al., "Trispecific $F(ab')_3$ Derivatives That Use Cooperative Signaling Via the TCR/CD3 Complex and CD2 to Activate and Redirect Resting Cytotoxic T cells," *J. Immunol. 147*:60-69, The American Association of Immunologists, United States (1991).
Unanue, E. and Benacerraf, B., "Textbook of Immunology," 2nd ed., pp. 218, Lippincott Williams & Wilkins, United States (1984).
Vaughan, T., et al., "Human Antibodies with Sub-nanomolar Affinities Isolated from a Large Non-immunized Phage Display Library," *Nat. Biotech. 14*:309-314, Nature America, Inc., United States (1996).
Verhoeyen, M., et al., "Reshaping Human Antibodies: Grafting an Antilysozyme Activity," *Science 239*:1534-1536, American Association for the Advancement of Science, United States (1988).
Vogel, W., "Discoidin domain receptors: structural relations and functional implications," *FASEB 13*(*Supplement*):S77-S82, The Federation, United States (1999).
Wang, Y., et al., "An orthotopic metastatic prostate cancer model in SCID mice via grafting of a transplantable human prostate tumor line," *Laboratory Investigation 85*:1395-1404, USCAP, Inc., United States (2005).
Weiner, H., et al., "Consistent and Selective Expression of the Discoidin Domain Receptor-1 Tyrosine Kinase in Human Brain Tumors," *Neurosurgery 47*:1400-1409, Williams & Wilkins, United States (2000).
Weiner, H., et al., "Pediatric Brain Tumors Express Multiple Receptor Tyrosine Kinases Including Novel Cell Adhesion Kinases," *Pediatr. Neurosurg. 25*:64-72, S. Karger, Switzerland (1996).
Xu, L., et al., "Activation of the Discoidin Domain Receptor 2 Induces Expression of Matrix Metalloproteinase 13 Associated with Osteoarthritis in Mice," *J. Biol.Chem. 280*:548-555, The American Society for Biochemistry and Molecular Biology, Inc., United States (2005).
"(DDRI_HUMAN) Reviewed," UniProtKB/Swiss-Prot Identifer Q08345, accessed on Apr. 10, 2013, accessed from http://www.uniprot.org/uniprot/Q08345, 4 pages.
Paul, W.D., *Fundamental Immunology*, 3rd Edition, pp. 292-295, Raven Press, Ltd., United States (1993).
Rudikoff, S., et al., "Single amino acid substitution altering antigen-binding specificity," *Proc. Natl. Acad. Sci. USA 79*(6):1979-1983, National Academy of Sciences, United States (1982).
Colman, P.M., "Effects of amino acid sequence changes on antibody-antigen interactions," *Research in Immunology*, 145:33-36, Institut Pasteur/Elsevier, Paris (1994).
Janeway, C.A., et al., *Immunobiology*, 5th Edition, pp. 94-105, Garland Publishing, United States (2001).
Valiathan, R.R., et al., "Discoidin domain receptor tyrosine kinases: new players in cancer progression," *Cancer Metastasis Rev. 31*:295-321 Springer Science+Business Media, LLC, United States (Feb. 2012).
Kim, H-G., et al., "DDR1 Receptor Tyrosine Kinase Promotes Prosurvival Pathway through Notch 1 Activation," *J. Biol. Chem. 286*(20):17672-17681, The American Society for Biochemistry and Molecular Biology, Inc., United States (May 2011).

(56) References Cited

OTHER PUBLICATIONS

Valencia, K., et al., “Inhibition of collagen receptor Discoidin Domain Receptor-1 (DDR1) Reduces Cell Survival, Homing and Colonization in Lung Cancer Bone Metastasis,” *Clin. Can. Res. 18*:969-980, American Association for Cancer Research, United States (Jan. 2012).

Co-pending U.S. Appl. No. 13/801,198, inventors Gurney, A., et al., filed Mar. 13, 2013 (now published as U.S. Pat. Publ. No. 2013/0336970 A1).

Co-pending U.S. Appl. No. 14/087,853, inventors Gurney, A., et al., filed Nov. 22, 2013.

Office Action, mailed Apr. 17, 2013, in U.S. Appl. No. 13/058,684, Gurney, A.L., et al., filed May 9, 2011.

* cited by examiner 5A
5B
5C
5D

SEQUENCE LISTING

<160> NUMBER OF SEQ ID NOS: 41

<210> SEQ ID NO 1
<211> LENGTH: 417
<212> TYPE: PRT
<213> ORGANISM: Artificial Sequence
<220> FEATURE:
<223> OTHER INFORMATION: Synthetic DDR1 immunized fragment

<400> SEQUENCE: 1

```
Met Gly Pro Glu Ala Leu Ser Ser Leu Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285
```

```
Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala


<210> SEQ ID NO 2
<211> LENGTH: 876
<212> TYPE: PRT
<213> ORGANISM: Artificial Sequence
<220> FEATURE:
<223> OTHER INFORMATION: Synthetic DDR1 transcript A sequence

<400> SEQUENCE: 2

Met Gly Pro Glu Ala Leu Ser Ser Leu Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220
```

```
Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
    450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Tyr Ser Gly Asp Tyr Met Glu
            500                 505                 510

Pro Glu Lys Pro Gly Ala Pro Leu Leu Pro Pro Pro Pro Gln Asn Ser
        515                 520                 525

Val Pro His Tyr Ala Glu Ala Asp Ile Val Thr Leu Gln Gly Val Thr
    530                 535                 540

Gly Gly Asn Thr Tyr Ala Val Pro Ala Leu Pro Pro Gly Ala Val Gly
545                 550                 555                 560

Asp Gly Pro Pro Arg Val Asp Phe Pro Arg Ser Arg Leu Arg Phe Lys
                565                 570                 575

Glu Lys Leu Gly Glu Gly Gln Phe Gly Glu Val His Leu Cys Glu Val
            580                 585                 590

Asp Ser Pro Gln Asp Leu Val Ser Leu Asp Phe Pro Leu Asn Val Arg
        595                 600                 605

Lys Gly His Pro Leu Leu Val Ala Val Lys Ile Leu Arg Pro Asp Ala
    610                 615                 620

Thr Lys Asn Ala Arg Asn Asp Phe Leu Lys Glu Val Lys Ile Met Ser
625                 630                 635                 640

Arg Leu Lys Asp Pro Asn Ile Ile Arg Leu Leu Gly Val Cys Val Gln
```

```
                645                 650                 655

Asp Asp Pro Leu Cys Met Ile Thr Asp Tyr Met Glu Asn Gly Asp Leu
            660                 665                 670

Asn Gln Phe Leu Ser Ala His Gln Leu Glu Asp Lys Ala Ala Glu Gly
        675                 680                 685

Ala Pro Gly Asp Gly Gln Ala Ala Gln Gly Pro Thr Ile Ser Tyr Pro
    690                 695                 700

Met Leu Leu His Val Ala Ala Gln Ile Ala Ser Gly Met Arg Tyr Leu
705                 710                 715                 720

Ala Thr Leu Asn Phe Val His Arg Asp Leu Ala Thr Arg Asn Cys Leu
                725                 730                 735

Val Gly Glu Asn Phe Thr Ile Lys Ile Ala Asp Phe Gly Met Ser Arg
            740                 745                 750

Asn Leu Tyr Ala Gly Asp Tyr Tyr Arg Val Gln Gly Arg Ala Val Leu
        755                 760                 765

Pro Ile Arg Trp Met Ala Trp Glu Cys Ile Leu Met Gly Lys Phe Thr
    770                 775                 780

Thr Ala Ser Asp Val Trp Ala Phe Gly Val Thr Leu Trp Glu Val Leu
785                 790                 795                 800

Met Leu Cys Arg Ala Gln Pro Phe Gly Gln Leu Thr Asp Glu Gln Val
                805                 810                 815

Ile Glu Asn Ala Gly Glu Phe Phe Arg Asp Gln Gly Arg Gln Val Tyr
            820                 825                 830

Leu Ser Arg Pro Pro Ala Cys Pro Gln Gly Leu Tyr Glu Leu Met Leu
        835                 840                 845

Arg Cys Trp Ser Arg Glu Ser Glu Gln Arg Pro Pro Phe Ser Gln Leu
    850                 855                 860

His Arg Phe Leu Ala Glu Asp Ala Leu Asn Thr Val
865                 870                 875


<210> SEQ ID NO 3
<211> LENGTH: 855
<212> TYPE: PRT
<213> ORGANISM: Artificial Sequence
<220> FEATURE:
<223> OTHER INFORMATION: Synthetic human DDR2 sequence

<400> SEQUENCE: 3

Met Ile Leu Ile Pro Arg Met Leu Leu Val Leu Phe Leu Leu Leu Pro
1               5                   10                  15

Ile Leu Ser Ser Ala Lys Ala Gln Val Asn Pro Ala Ile Cys Arg Tyr
            20                  25                  30

Pro Leu Gly Met Ser Gly Gly Gln Ile Pro Asp Glu Asp Ile Thr Ala
        35                  40                  45

Ser Ser Gln Trp Ser Glu Ser Thr Ala Ala Lys Tyr Gly Arg Leu Asp
    50                  55                  60

Ser Glu Glu Gly Asp Gly Ala Trp Cys Pro Glu Ile Pro Val Glu Pro
65                  70                  75                  80

Asp Asp Leu Lys Glu Phe Leu Gln Ile Asp Leu His Thr Leu His Phe
                85                  90                  95

Ile Thr Leu Val Gly Thr Gln Gly Arg His Ala Gly Gly His Gly Ile
            100                 105                 110

Glu Phe Ala Pro Met Tyr Lys Ile Asn Tyr Ser Arg Asp Gly Thr Arg
        115                 120                 125

Trp Ile Ser Trp Arg Asn Arg His Gly Lys Gln Val Leu Asp Gly Asn
```

-continued

```
    130                 135                 140

Ser Asn Pro Tyr Asp Ile Phe Leu Lys Asp Leu Glu Pro Pro Ile Val
145                 150                 155                 160

Ala Arg Phe Val Arg Phe Ile Pro Val Thr Asp His Ser Met Asn Val
                165                 170                 175

Cys Met Arg Val Glu Leu Tyr Gly Cys Val Trp Leu Asp Gly Leu Val
            180                 185                 190

Ser Tyr Asn Ala Pro Ala Gly Gln Gln Phe Val Leu Pro Gly Gly Ser
        195                 200                 205

Ile Ile Tyr Leu Asn Asp Ser Val Tyr Asp Gly Ala Val Gly Tyr Ser
    210                 215                 220

Met Thr Glu Gly Leu Gly Gln Leu Thr Asp Gly Val Ser Gly Leu Asp
225                 230                 235                 240

Asp Phe Thr Gln Thr His Glu Tyr His Val Trp Pro Gly Tyr Asp Tyr
                245                 250                 255

Val Gly Trp Arg Asn Glu Ser Ala Thr Asn Gly Tyr Ile Glu Ile Met
            260                 265                 270

Phe Glu Phe Asp Arg Ile Arg Asn Phe Thr Thr Met Lys Val His Cys
        275                 280                 285

Asn Asn Met Phe Ala Lys Gly Val Lys Ile Phe Lys Glu Val Gln Cys
    290                 295                 300

Tyr Phe Arg Ser Glu Ala Ser Glu Trp Glu Pro Asn Ala Ile Ser Phe
305                 310                 315                 320

Pro Leu Val Leu Asp Asp Val Asn Pro Ser Ala Arg Phe Val Thr Val
                325                 330                 335

Pro Leu His His Arg Met Ala Ser Ala Ile Lys Cys Gln Tyr His Phe
            340                 345                 350

Ala Asp Thr Trp Met Met Phe Ser Glu Ile Thr Phe Gln Ser Asp Ala
        355                 360                 365

Ala Met Tyr Asn Asn Ser Glu Ala Leu Pro Thr Ser Pro Met Ala Pro
    370                 375                 380

Thr Thr Tyr Asp Pro Met Leu Lys Val Asp Asp Ser Asn Thr Arg Ile
385                 390                 395                 400

Leu Ile Gly Cys Leu Val Ala Ile Ile Phe Ile Leu Leu Ala Ile Ile
                405                 410                 415

Val Ile Ile Leu Trp Arg Gln Phe Trp Gln Lys Met Leu Glu Lys Ala
            420                 425                 430

Ser Arg Arg Met Leu Asp Asp Glu Met Thr Val Ser Leu Ser Leu Pro
        435                 440                 445

Ser Asp Ser Ser Met Phe Asn Asn Asn Arg Ser Ser Ser Pro Ser Glu
    450                 455                 460

Gln Gly Ser Asn Ser Thr Tyr Asp Arg Ile Phe Pro Leu Arg Pro Asp
465                 470                 475                 480

Tyr Gln Glu Pro Ser Arg Leu Ile Arg Lys Leu Pro Glu Phe Ala Pro
                485                 490                 495

Gly Glu Glu Glu Ser Gly Cys Ser Gly Val Val Lys Pro Val Gln Pro
            500                 505                 510

Ser Gly Pro Glu Gly Val Pro His Tyr Ala Glu Ala Asp Ile Val Asn
        515                 520                 525

Leu Gln Gly Val Thr Gly Gly Asn Thr Tyr Ser Val Pro Ala Val Thr
    530                 535                 540

Met Asp Leu Leu Ser Gly Lys Asp Val Ala Val Glu Glu Phe Pro Arg
545                 550                 555                 560
```

```
Lys Leu Leu Thr Phe Lys Glu Lys Leu Gly Glu Gly Gln Phe Gly Glu
                565                 570                 575

Val His Leu Cys Glu Val Glu Gly Met Glu Lys Phe Lys Asp Lys Asp
            580                 585                 590

Phe Ala Leu Asp Val Ser Ala Asn Gln Pro Val Leu Val Ala Val Lys
        595                 600                 605

Met Leu Arg Ala Asp Ala Asn Lys Asn Ala Arg Asn Asp Phe Leu Lys
    610                 615                 620

Glu Ile Lys Ile Met Ser Arg Leu Lys Asp Pro Asn Ile Ile His Leu
625                 630                 635                 640

Leu Ser Val Cys Ile Thr Asp Asp Pro Leu Cys Met Ile Thr Glu Tyr
                645                 650                 655

Met Glu Asn Gly Asp Leu Asn Gln Phe Leu Ser Arg His Glu Pro Pro
            660                 665                 670

Asn Ser Ser Ser Ser Asp Val Arg Thr Val Ser Tyr Thr Asn Leu Lys
        675                 680                 685

Phe Met Ala Thr Gln Ile Ala Ser Gly Met Lys Tyr Leu Ser Ser Leu
    690                 695                 700

Asn Phe Val His Arg Asp Leu Ala Thr Arg Asn Cys Leu Val Gly Lys
705                 710                 715                 720

Asn Tyr Thr Ile Lys Ile Ala Asp Phe Gly Met Ser Arg Asn Leu Tyr
                725                 730                 735

Ser Gly Asp Tyr Tyr Arg Ile Gln Gly Arg Ala Val Leu Pro Ile Arg
            740                 745                 750

Trp Met Ser Trp Glu Ser Ile Leu Leu Gly Lys Phe Thr Thr Ala Ser
        755                 760                 765

Asp Val Trp Ala Phe Gly Val Thr Leu Trp Glu Thr Phe Thr Phe Cys
    770                 775                 780

Gln Glu Gln Pro Tyr Ser Gln Leu Ser Asp Glu Gln Val Ile Glu Asn
785                 790                 795                 800

Thr Gly Glu Phe Phe Arg Asp Gln Gly Arg Gln Thr Tyr Leu Pro Gln
                805                 810                 815

Pro Ala Ile Cys Pro Asp Ser Val Tyr Lys Leu Met Leu Ser Cys Trp
            820                 825                 830

Arg Arg Asp Thr Lys Asn Arg Pro Ser Phe Gln Glu Ile His Leu Leu
        835                 840                 845

Leu Leu Gln Gln Gly Asp Glu
    850                 855
```

<210> SEQ ID NO 4
<211> LENGTH: 1253
<212> TYPE: DNA
<213> ORGANISM: Artificial Sequence
<220> FEATURE:
<223> OTHER INFORMATION: Synthetic DDR1 immunized fragment

<400> SEQUENCE: 4

```
atgggaccag aggccctgtc atctttactg ctgctgctct tggtggcaag tggagatgct     60

gacatgaagg gacattttga tcctgccaag tgccgctatg ccctgggcat gcaggaccgg    120

accatcccag acagtgacat ctctgcttcc agctcctggt cagattccac tgccgcccgc    180

cacagcaggt tggagagcag tgacggggat ggggcctggt gccccgcagg gtcggtgttt    240

cccaaggagg aggagtactt gcaggtggat ctacaacgac tgcacctggt ggctctggtg    300

ggcacccagg gacggcatgc cgggggcctg ggcaaggagt tctcccggag ctaccggctg    360
```

cgttactccc gggatggtcg ccgctggatg ggctggaagg accgctgggg tcaggaggtg 420
atctcaggca atgaggaccc tgagggagtg gtgctgaagg accttgggcc ccccatggtt 480
gcccgactgg ttcgcttcta cccccgggct gaccgggtca tgagcgtctg tctgcgggta 540
gagctctatg gctgcctctg gagggatgga ctcctgtctt acactgcccc tgtggggcag 600
acaatgtatt tatctgaggc cgtgtacctc aacgactcca cctatgacgg acataccgtg 660
ggcggactgc agtatggggg tctgggccag ctggcagatg gtgtggtggg gctggatgac 720
tttaggaaga gtcaggagct gcgggtctgg ccaggctatg actatgtggg atggagcaac 780
cacagcttct ccagtggcta tgtggagatg gagtttgagt ttgaccggct gagggccttc 840
caggctatgc aggtccactg taacaacatg cacacgctgg gagcccgtct gcctggcggg 900
gtggaatgtc gcttccggcg tggccctgcc atggcctggg agggggagcc catgcgccac 960
aacctagggg gcaacctggg ggaccccaga gcccgggctg tctcagtgcc ccttggcggc 1020
cgtgtggctc gctttctgca gtgccgcttc ctctttgcgg ggccctggtt actcttcagc 1080
gaaatctcct tcatctctga tgtggtgaac aattcctctc cggcactggg aggcaccttc 1140
ccgccagccc cctggtggcc gcctggccca cctcccacca acttcagcag cttggagctg 1200
gagcccagag gccagcagcc cgtggccaag gccgagggga gcccgaccgc cgg 1253

<210> SEQ ID NO 5
<211> LENGTH: 2631
<212> TYPE: DNA
<213> ORGANISM: Artificial Sequence
<220> FEATURE:
<223> OTHER INFORMATION: Synthetic DDR1 transcript A sequence

<400> SEQUENCE: 5
atgggaccag aggccctgtc atctttactg ctgctgctct tggtggcaag tggagatgct 60
gacatgaagg gacattttga tcctgccaag tgccgctatg ccctgggcat gcaggaccgg 120
accatcccag acagtgacat ctctgcttcc agctcctggt cagattccac tgccgcccgc 180
cacagcaggt tggagagcag tgacggggat ggggcctggt gccccgcagg gtcggtgttt 240
cccaaggagg aggagtactt gcaggtggat ctacaacgac tgcacctggt ggctctggtg 300
ggcacccagg gacggcatgc cgggggcctg ggcaaggagt tctcccggag ctaccggctg 360
cgttactccc gggatggtcg ccgctggatg ggctggaagg accgctgggg tcaggaggtg 420
atctcaggca atgaggaccc tgagggagtg gtgctgaagg accttgggcc ccccatggtt 480
gcccgactgg ttcgcttcta cccccgggct gaccgggtca tgagcgtctg tctgcgggta 540
gagctctatg gctgcctctg gagggatgga ctcctgtctt acactgcccc tgtggggcag 600
acaatgtatt tatctgaggc cgtgtacctc aacgactcca cctatgacgg acataccgtg 660
ggcggactgc agtatggggg tctgggccag ctggcagatg gtgtggtggg gctggatgac 720
tttaggaaga gtcaggagct gcgggtctgg ccaggctatg actatgtggg atggagcaac 780
cacagcttct ccagtggcta tgtggagatg gagtttgagt ttgaccggct gagggccttc 840
caggctatgc aggtccactg taacaacatg cacacgctgg gagcccgtct gcctggcggg 900
gtggaatgtc gcttccggcg tggccctgcc atggcctggg agggggagcc catgcgccac 960
aacctagggg gcaacctggg ggaccccaga gcccgggctg tctcagtgcc ccttggcggc 1020
cgtgtggctc gctttctgca gtgccgcttc ctctttgcgg ggccctggtt actcttcagc 1080
gaaatctcct tcatctctga tgtggtgaac aattcctctc cggcactggg aggcaccttc 1140

```
ccgccagccc cctggtggcc gcctggccca cctcccacca acttcagcag cttggagctg   1200

gagcccagag gccagcagcc cgtggccaag gccgagggga gcccgaccgc catcctcatc   1260

ggctgcctgg tggccatcat cctgctcctg ctgctcatca ttgccctcat gctctggcgg   1320

ctgcactggc gcaggctcct cagcaaggct gaacggaggg tgttggaaga ggagctgacg   1380

gttcacctct ctgtccctgg ggacactatc ctcatcaaca accgcccagg tcctagagag   1440

ccacccccgt accaggagcc ccggcctcgt gggaatccgc cccactccgc tccctgtgtc   1500

cccaatggct ctgcctacag tggggactat atggagcctg agaagccagg cgccccgctt   1560

ctgcccccac ctccccagaa cagcgtcccc cattatgccg aggctgacat tgttaccctg   1620

cagggcgtca ccgggggcaa cacctatgct gtgcctgcac tgcccccagg ggcagtcggg   1680

gatgggcccc ccagagtgga tttccctcga tctcgactcc gcttcaagga gaagcttggc   1740

gagggccagt ttggggaggt gcacctgtgt gaggtcgaca gccctcaaga tctggttagt   1800

cttgatttcc cccttaatgt gcgtaaggga caccctttgc tggtagctgt caagatctta   1860

cggccagatg ccaccaagaa tgccaggaat gatttcctga aagaggtgaa gatcatgtcg   1920

aggctcaagg acccaaacat cattcggctg ctgggcgtgt gtgtgcagga cgacccccctc   1980

tgcatgatta ctgactacat ggagaacggc gacctcaacc agttcctcag tgcccaccag   2040

ctggaggaca aggcagccga gggggcccct ggggacgggc aggctgcgca ggggcccacc   2100

atcagctacc caatgctgct gcatgtggca gcccagatcg cctccggcat gcgctatctg   2160

gccacactca actttgtaca tcgggacctg gccacgcgga actgcctagt tggggaaaat   2220

ttcaccatca aaatcgcaga ctttggcatg agccggaacc tctatgctgg ggactattac   2280

cgtgtgcagg gccgggcagt gctgcccatc cgctggatgg cctgggagtg catcctcatg   2340

gggaagttca cgactgcgag tgacgtgtgg gcctttggtg tgaccctgtg ggaggtgctg   2400

atgctctgta gggcccagcc ctttgggcag ctcaccgacg agcaggtcat cgagaacgcg   2460

ggggagttct tccgggacca gggccggcag gtgtacctgt cccggccgcc tgcctgcccg   2520

cagggcctat atgagctgat gcttcggtgc tggagccggg agtctgagca gcgaccaccc   2580

ttttcccagc tgcatcggtt cctggcagag gatgcactca acacggtgtg a            2631
```

<210> SEQ ID NO 6
<211> LENGTH: 2568
<212> TYPE: DNA
<213> ORGANISM: Artificial Sequence
<220> FEATURE:
<223> OTHER INFORMATION: Synthetic DDR2 sequence

<400> SEQUENCE: 6

```
atgatcctga ttcccagaat gctcttggtg ctgttcctgc tgctgcctat cttgagttct     60

gcaaaagctc aggttaatcc agctatatgc cgctatcctc tgggcatgtc aggaggccag    120

attccagatg aggacatcac agcttccagt cagtggtcag agtccacagc tgccaaatat    180

ggaaggctgg actcagaaga aggggatgga gcctggtgcc ctgagattcc agtggaacct    240

gatgacctga aggagtttct gcagattgac ttgcacaccc tccattttat cactctggtg    300

gggacccagg ggcgccatgc aggaggtcat ggcatcgagt ttgcccccat gtacaagatc    360

aattacagtc gggatggcac tcgctggatc tcttggcgga accgtcatgg gaaacaggtg    420

ctggatggaa atagtaaccc ctatgacatt ttcctaaagg acttggagcc gcccattgta    480

gccagatttg tccggttcat tccagtcacc gaccactcca tgaatgtgtg tatgagagtg    540

gagctttacg gctgtgtctg gctagatggc ttggtgtctt acaatgctcc agctgggcag    600
```

```
cagtttgtac tccctggagg ttccatcatt tatctgaatg attctgtcta tgatggagct    660
gttggataca gcatgacaga agggctaggc caattgaccg atggtgtgtc tggcctggac    720
gatttcaccc agacccatga ataccacgtg tggcccggct atgactatgt gggctggcgg    780
aacgagagtg ccaccaatgg ctacattgag atcatgtttg aatttgaccg catcaggaat    840
ttcactacca tgaaggtcca ctgcaacaac atgtttgcta aaggtgtgaa gatctttaag    900
gaggtacagt gctacttccg ctctgaagcc agtgagtggg aacctaatgc catttccttc    960
ccccttgtcc tggatgacgt caaccccagt gctcggtttg tcacggtgcc tctccaccac   1020
cgaatggcca gtgccatcaa gtgtcaatac cattttgcag atacctggat gatgttcagt   1080
gagatcacct tccaatcaga tgctgcaatg tacaacaact ctgaagccct gcccacctct   1140
cctatggcac ccacaaccta tgatccaatg cttaaagttg atgacagcaa cactcggatc   1200
ctgattggct gcttggtggc catcatcttt atcctcctgg ccatcattgt catcatcctc   1260
tggaggcagt tctggcagaa aatgctggag aaggcttctc ggaggatgct ggatgatgaa   1320
atgacagtca gcctttccct gccaagtgat tctagcatgt tcaacaataa ccgctcctca   1380
tcacctagtg aacaagggtc caactcgact tacgatcgca tctttcccct tcgccctgac   1440
taccaggagc catccaggct gatacgaaaa ctcccagaat ttgctccagg ggaggaggag   1500
tcaggctgca gcggtgttgt gaagccagtc cagcccagtg gccctgaggg ggtgccccac   1560
tatgcagagg ctgacatagt gaacctccaa ggagtgacag gaggcaacac atactcagtg   1620
cctgccgtca ccatggacct gctctcagga aaagatgtgg ctgtggagga gttccccagg   1680
aaactcctaa ctttcaaaga gaagctggga gaaggacagt ttggggaggt tcatctctgt   1740
gaagtggagg gaatggaaaa attcaaagac aaagattttg ccctagatgt cagtgccaac   1800
cagcctgtcc tggtggctgt gaaaatgctc cgagcagatg ccaacaagaa tgccaggaat   1860
gattttctta aggagataaa gatcatgtct cggctcaagg acccaaacat catccatcta   1920
ttatctgtgt gtatcactga tgaccctctc tgtatgatca ctgaatacat ggagaatgga   1980
gatctcaatc agtttctttc ccgccacgag ccccctaatt cttcctccag cgatgtacgc   2040
actgtcagtt acaccaatct gaagtttatg gctacccaaa ttgcctctgg catgaagtac   2100
ctttcctctc ttaattttgt tcaccgagat ctggccacac gaaactgttt agtgggtaag   2160
aactacacaa tcaagatagc tgactttgga atgagcagga acctgtacag tggtgactat   2220
taccggatcc agggccgggc agtgctccct atccgctgga tgtcttggga gagtatcttg   2280
ctgggcaagt tcactacagc aagtgatgtg tgggcctttg ggttactttt gtgggagact   2340
ttcacctttt gtcaagaaca gccctattcc cagctgtcag atgaacaggt tattgagaat   2400
actggagagt tcttccgaga ccaagggagg cagacttacc tccctcaacc agccatttgt   2460
cctgactctg tgtataagct gatgctcagc tgctggagaa gagatacgaa gaaccgtccc   2520
tcattccaag aaatccacct tctgctcctt caacaaggcg acgagtga                2568
```

<210> SEQ ID NO 7
<211> LENGTH: 1941
<212> TYPE: DNA
<213> ORGANISM: Artificial Sequence
<220> FEATURE:
<223> OTHER INFORMATION: Synthetic DDR1-Fc sequence

<400> SEQUENCE: 7

```
atgggaccag aggccctgtc atctttactg ctgctgctct tggtggcaag tggagatgct     60
```

```
gacatgaagg gacattttga tcctgccaag tgccgctatg ccctgggcat gcaggaccgg    120

accatcccag acagtgacat ctctgcttcc agctcctggt cagattccac tgccgcccgc    180

cacagcaggt tggagagcag tgacggggat ggggcctggt gccccgcagg gtcggtgttt    240

cccaaggagg aggagtactt gcaggtggat ctacaacgac tgcacctggt ggctctggtg    300

ggcacccagg gacggcatgc cgggggcctg ggcaaggagt tctcccggag ctaccggctg    360

cgttactccc gggatggtcg ccgctggatg ggctggaagg accgctgggg tcaggaggtg    420

atctcaggca atgaggaccc tgagggagtg gtgctgaagg accttgggcc ccccatggtt    480

gcccgactgg ttcgcttcta cccccgggct gaccgggtca tgagcgtctg tctgcgggta    540

gagctctatg gctgcctctg gagggatgga ctcctgtctt acactgcccc tgtggggcag    600

acaatgtatt tatctgaggc cgtgtacctc aacgactcca cctatgacgg acataccgtg    660

ggcggactgc agtatggggg tctgggccag ctggcagatg gtgtggtggg gctggatgac    720

tttaggaaga gtcaggagct gcgggtctgg ccaggctatg actatgtggg atggagcaac    780

cacagcttct ccagtggcta tgtggagatg gagtttgagt ttgaccggct gagggccttc    840

caggctatgc aggtccactg taacaacatg cacacgctgg gagcccgtct gcctggcggg    900

gtggaatgtc gcttccggcg tggccctgcc atggcctggg agggggagcc catgcgccac    960

aacctagggg gcaacctggg ggaccccaga gcccgggctg tctcagtgcc ccttggcggc   1020

cgtgtggctc gctttctgca gtgccgcttc ctctttgcgg ggccctggtt actcttcagc   1080

gaaatctcct tcatctctga tgtggtgaac aattcctctc cggcactggg aggcaccttc   1140

ccgccagccc cctggtggcc gcctggccca cctcccacca acttcagcag cttggagctg   1200

gagcccagag gccagcagcc cgtggccaag gccgagggga gcccgaccgc cgggcgcgcc   1260

gacaaaactc acacatgccc accgtgccca gcacctgaac tcctgggggg accgtcagtc   1320

ttcctcttcc ccccaaaacc caaggacacc ctcatgatct cccggacccc tgaggtcaca   1380

tgcgtggtgg tggacgtgag ccacgaagac cctgaggtca agttcaactg gtacgtggac   1440

ggcgtggagg tgcataatgc caagacaaag ccgcgggagg agcagtacaa cagcacgtac   1500

cgtgtggtca gcgtcctcac cgtcctgcac caggactggc tgaatggcaa ggagtacaag   1560

tgcaaggtct ccaacaaagc cctcccagcc cccatcgaga aaaccatctc caaagccaaa   1620

gggcagcccc gagaaccaca ggtgtacacc ctgcccccat cccgggatga gctgaccaag   1680

aaccaggtca gcctgacctg cctggtcaaa ggcttctatc ccagcgacat cgccgtggag   1740

tgggagagca atgggcagcc ggagaacaac tacaagacca cgcctcccgt gctggactcc   1800

gacggctcct tcttcctcta cagcaagctc accgtggaca agagcaggtg gcagcagggg   1860

aacgtcttct catgctccgt gatgcatgag gctctgcaca accactacac acagaagagc   1920

ctctccctgt ctccgggtaa a                                             1941
```

<210> SEQ ID NO 8
<211> LENGTH: 647
<212> TYPE: PRT
<213> ORGANISM: Artificial Sequence
<220> FEATURE:
<223> OTHER INFORMATION: Synthetic DDR1-Fc sequence

<400> SEQUENCE: 8

```
Met Gly Pro Glu Ala Leu Ser Ser Leu Leu Leu Leu Leu Leu Val Ala
1               5                   10                  15

Ser Gly Asp Ala Asp Met Lys Gly His Phe Asp Pro Ala Lys Cys Arg
            20                  25                  30
```

```
Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Gly Arg Ala Asp Lys Thr His Thr Cys Pro Pro Cys Pro Ala Pro
            420                 425                 430

Glu Leu Leu Gly Gly Pro Ser Val Phe Leu Phe Pro Pro Lys Pro Lys
        435                 440                 445
```

```
Asp Thr Leu Met Ile Ser Arg Thr Pro Glu Val Thr Cys Val Val Val
    450                 455                 460

Asp Val Ser His Glu Asp Pro Glu Val Lys Phe Asn Trp Tyr Val Asp
465                 470                 475                 480

Gly Val Glu Val His Asn Ala Lys Thr Lys Pro Arg Glu Glu Gln Tyr
                485                 490                 495

Asn Ser Thr Tyr Arg Val Val Ser Val Leu Thr Val Leu His Gln Asp
            500                 505                 510

Trp Leu Asn Gly Lys Glu Tyr Lys Cys Lys Val Ser Asn Lys Ala Leu
        515                 520                 525

Pro Ala Pro Ile Glu Lys Thr Ile Ser Lys Ala Lys Gly Gln Pro Arg
    530                 535                 540

Glu Pro Gln Val Tyr Thr Leu Pro Pro Ser Arg Asp Glu Leu Thr Lys
545                 550                 555                 560

Asn Gln Val Ser Leu Thr Cys Leu Val Lys Gly Phe Tyr Pro Ser Asp
                565                 570                 575

Ile Ala Val Glu Trp Glu Ser Asn Gly Gln Pro Glu Asn Asn Tyr Lys
            580                 585                 590

Thr Thr Pro Pro Val Leu Asp Ser Asp Gly Ser Phe Phe Leu Tyr Ser
        595                 600                 605

Lys Leu Thr Val Asp Lys Ser Arg Trp Gln Gln Gly Asn Val Phe Ser
    610                 615                 620

Cys Ser Val Met His Glu Ala Leu His Asn His Tyr Thr Gln Lys Ser
625                 630                 635                 640

Leu Ser Leu Ser Pro Gly Lys
                645


<210> SEQ ID NO 9
<211> LENGTH: 876
<212> TYPE: PRT
<213> ORGANISM: Artificial Sequence
<220> FEATURE:
<223> OTHER INFORMATION: Synthetic human DDR1a sequence

<400> SEQUENCE: 9

Met Gly Pro Glu Ala Leu Ser Ser Leu Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160
```

-continued

```
Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
    450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Tyr Ser Gly Asp Tyr Met Glu
            500                 505                 510

Pro Glu Lys Pro Gly Ala Pro Leu Leu Pro Pro Pro Pro Gln Asn Ser
        515                 520                 525

Val Pro His Tyr Ala Glu Ala Asp Ile Val Thr Leu Gln Gly Val Thr
    530                 535                 540

Gly Gly Asn Thr Tyr Ala Val Pro Ala Leu Pro Pro Gly Ala Val Gly
545                 550                 555                 560

Asp Gly Pro Pro Arg Val Asp Phe Pro Arg Ser Arg Leu Arg Phe Lys
                565                 570                 575

Glu Lys Leu Gly Glu Gly Gln Phe Gly Glu Val His Leu Cys Glu Val
```

580 585 590

Asp Ser Pro Gln Asp Leu Val Ser Leu Asp Phe Pro Leu Asn Val Arg
595 600 605

Lys Gly His Pro Leu Leu Val Ala Val Lys Ile Leu Arg Pro Asp Ala
610 615 620

Thr Lys Asn Ala Arg Asn Asp Phe Leu Lys Glu Val Lys Ile Met Ser
625 630 635 640

Arg Leu Lys Asp Pro Asn Ile Ile Arg Leu Leu Gly Val Cys Val Gln
645 650 655

Asp Asp Pro Leu Cys Met Ile Thr Asp Tyr Met Glu Asn Gly Asp Leu
660 665 670

Asn Gln Phe Leu Ser Ala His Gln Leu Glu Asp Lys Ala Ala Glu Gly
675 680 685

Ala Pro Gly Asp Gly Gln Ala Ala Gln Gly Pro Thr Ile Ser Tyr Pro
690 695 700

Met Leu Leu His Val Ala Ala Gln Ile Ala Ser Gly Met Arg Tyr Leu
705 710 715 720

Ala Thr Leu Asn Phe Val His Arg Asp Leu Ala Thr Arg Asn Cys Leu
725 730 735

Val Gly Glu Asn Phe Thr Ile Lys Ile Ala Asp Phe Gly Met Ser Arg
740 745 750

Asn Leu Tyr Ala Gly Asp Tyr Tyr Arg Val Gln Gly Arg Ala Val Leu
755 760 765

Pro Ile Arg Trp Met Ala Trp Glu Cys Ile Leu Met Gly Lys Phe Thr
770 775 780

Thr Ala Ser Asp Val Trp Ala Phe Gly Val Thr Leu Trp Glu Val Leu
785 790 795 800

Met Leu Cys Arg Ala Gln Pro Phe Gly Gln Leu Thr Asp Glu Gln Val
805 810 815

Ile Glu Asn Ala Gly Glu Phe Phe Arg Asp Gln Gly Arg Gln Val Tyr
820 825 830

Leu Ser Arg Pro Pro Ala Cys Pro Gln Gly Leu Tyr Glu Leu Met Leu
835 840 845

Arg Cys Trp Ser Arg Glu Ser Glu Gln Arg Pro Pro Phe Ser Gln Leu
850 855 860

His Arg Phe Leu Ala Glu Asp Ala Leu Asn Thr Val
865 870 875

<210> SEQ ID NO 10
<211> LENGTH: 2631
<212> TYPE: DNA
<213> ORGANISM: Artificial Sequence
<220> FEATURE:
<223> OTHER INFORMATION: Synthetic human DDR1a sequence

<400> SEQUENCE: 10
atgggaccag aggccctgtc atctttactg ctgctgctct tggtggcaag tggagatgct 60
gacatgaagg gacattttga tcctgccaag tgccgctatg ccctgggcat gcaggaccgg 120
accatcccag acagtgacat ctctgcttcc agctcctggt cagattccac tgccgcccgc 180
cacagcaggt tggagagcag tgacggggat ggggcctggt gccccgcagg gtcggtgttt 240
cccaaggagg aggagtactt gcaggtggat ctacaacgac tgcacctggt ggctctggtg 300
ggcacccagg gacggcatgc cgggggcctg ggcaaggagt tctcccggag ctaccggctg 360
cgttactccc gggatggtcg ccgctggatg ggctggaagg accgctgggg tcaggaggtg 420

```
atctcaggca atgaggaccc tgagggagtg gtgctgaagg accttgggcc ccccatggtt    480
gcccgactgg ttcgcttcta cccccgggct gaccgggtca tgagcgtctg tctgcgggta    540
gagctctatg gctgcctctg gagggatgga ctcctgtctt acactgcccc tgtggggcag    600
acaatgtatt tatctgaggc cgtgtacctc aacgactcca cctatgacgg acataccgtg    660
ggcggactgc agtatggggg tctgggccag ctggcagatg gtgtggtggg gctggatgac    720
tttaggaaga gtcaggagct gcgggtctgg ccaggctatg actatgtggg atggagcaac    780
cacagcttct ccagtggcta tgtggagatg gagtttgagt ttgaccggct gagggccttc    840
caggctatgc aggtccactg taacaacatg cacacgctgg gagcccgtct gcctggcggg    900
gtggaatgtc gcttccggcg tggccctgcc atggcctggg agggggagcc catgcgccac    960
aacctagggg gcaacctggg ggaccccaga gcccgggctg tctcagtgcc ccttggcggc   1020
cgtgtggctc gctttctgca gtgccgcttc ctctttgcgg ggccctggtt actcttcagc   1080
gaaatctcct tcatctctga tgtggtgaac aattcctctc cggcactggg aggcaccttc   1140
ccgccagccc cctggtggcc gcctggccca cctcccacca acttcagcag cttggagctg   1200
gagcccagag gccagcagcc cgtggccaag gccgagggga gcccgaccgc catcctcatc   1260
ggctgcctgg tggccatcat cctgctcctg ctgctcatca ttgccctcat gctctggcgg   1320
ctgcactggc gcaggctcct cagcaaggct gaacggaggg tgttggaaga ggagctgacg   1380
gttcacctct ctgtccctgg ggacactatc ctcatcaaca accgcccagg tcctagagag   1440
ccacccccgt accaggagcc ccggcctcgt gggaatccgc cccactccgc tccctgtgtc   1500
cccaatggct ctgcctacag tggggactat atggagcctg agaagccagg cgccccgctt   1560
ctgcccccac ctccccagaa cagcgtcccc cattatgccg aggctgacat tgttaccctg   1620
cagggcgtca ccgggggcaa cacctatgct gtgcctgcac tgcccccagg ggcagtcggg   1680
gatgggcccc ccagagtgga tttccctcga tctcgactcc gcttcaagga gaagcttggc   1740
gagggccagt ttggggaggt gcacctgtgt gaggtcgaca gccctcaaga tctggttagt   1800
cttgatttcc cccttaatgt gcgtaaggga cacccctttgc tggtagctgt caagatctta   1860
cggccagatg ccaccaagaa tgccaggaat gatttcctga aagaggtgaa gatcatgtcg   1920
aggctcaagg acccaaacat cattcggctg ctgggcgtgt gtgtgcagga cgacccccctc   1980
tgcatgatta ctgactacat ggagaacggc gacctcaacc agttcctcag tgcccaccag   2040
ctggaggaca aggcagccga gggggcccct ggggacgggc aggctgcgca ggggcccacc   2100
atcagctacc caatgctgct gcatgtggca gcccagatcg cctccggcat gcgctatctg   2160
gccacactca actttgtaca tcgggacctg gccacgcgga actgcctagt tggggaaaat   2220
ttcaccatca aaatcgcaga ctttggcatg agccggaacc tctatgctgg ggactattac   2280
cgtgtgcagg gccgggcagt gctgcccatc cgctggatgg cctgggagtg catcctcatg   2340
ggaagttca cgactgcgag tgacgtgtgg gcctttggtg tgaccctgtg ggaggtgctg   2400
atgctctgta gggcccagcc ctttgggcag ctcaccgacg agcaggtcat cgagaacgcg   2460
ggggagttct tccgggacca gggccggcag gtgtacctgt cccggccgcc tgcctgcccg   2520
cagggcctat atgagctgat gcttcggtgc tggagccggg agtctgagca gcgaccaccc   2580
ttttcccagc tgcatcggtt cctggcagag gatgcactca acacggtgtg a            2631
```

<210> SEQ ID NO 11
<211> LENGTH: 2742
<212> TYPE: DNA

<213> ORGANISM: Artificial Sequence
<220> FEATURE:
<223> OTHER INFORMATION: Synthetic human DDR1b sequence

<400> SEQUENCE: 11

```
atgggaccag aggccctgtc atctttactg ctgctgctct tggtggcaag tggagatgct     60
gacatgaagg gacattttga tcctgccaag tgccgctatg ccctgggcat gcaggaccgg    120
accatcccag acagtgacat ctctgcttcc agctcctggt cagattccac tgccgcccgc    180
cacagcaggt tggagagcag tgacggggat ggggcctggt gccccgcagg gtcggtgttt    240
cccaaggagg aggagtactt gcaggtggat ctacaacgac tgcacctggt ggctctggtg    300
ggcacccagg gacggcatgc cgggggcctg ggcaaggagt tctcccggag ctaccggctg    360
cgttactccc gggatggtcg ccgctggatg ggctggaagg accgctgggg tcaggaggtg    420
atctcaggca atgaggaccc tgagggagtg gtgctgaagg accttgggcc ccccatggtt    480
gcccgactgg ttcgcttcta cccccgggct gaccgggtca tgagcgtctg tctgcgggta    540
gagctctatg gctgcctctg gagggatgga ctcctgtctt acaccgcccc tgtggggcag    600
acaatgtatt tatctgaggc cgtgtacctc aacgactcca cctatgacgg acataccgtg    660
ggcggactgc agtatggggg tctgggccag ctggcagatg gtgtggtggg gctggatgac    720
tttaggaaga gtcaggagct gcgggtctgg ccaggctatg actatgtggg atggagcaac    780
cacagcttct ccagtggcta tgtggagatg gagtttgagt ttgaccggct gagggccttc    840
caggctatgc aggtccactg taacaacatg cacacgctgg gagcccgtct gcctggcggg    900
gtggaatgtc gcttccggcg tggccctgcc atggcctggg agggggagcc catgcgccac    960
aacctagggg gcaacctggg ggaccccaga gcccgggctg tctcagtgcc ccttggcggc   1020
cgtgtggctc gctttctgca gtgccgcttc ctctttgcgg ggccctggtt actcttcagc   1080
gaaatctcct tcatctctga tgtggtgaac aattcctctc cggcactggg aggcaccttc   1140
ccgccagccc cctggtggcc gcctggccca cctcccacca acttcagcag cttggagctg   1200
gagcccagag gccagcagcc cgtggccaag gccgaggga gcccgaccgc catcctcatc    1260
ggctgcctgg tggccatcat cctgctcctg ctgctcatca ttgccctcat gctctggcgg   1320
ctgcactggc gcaggctcct cagcaaggct gaacggaggg tgttggaaga ggagctgacg   1380
gttcacctct ctgtccctgg ggacactatc ctcatcaaca accgcccagg tcctagagag   1440
ccacccccgt accaggagcc ccggcctcgt gggaatccgc cccactccgc tccctgtgtc   1500
cccaatggct ctgcgttgct gctctccaat ccagcctacc gcctccttct ggccacttac   1560
gcccgtcccc ctcgaggccc gggccccccc acacccgcct gggccaaacc caccaacacc   1620
caggcctaca gtggggacta tatggagcct gagaagccag gcgccccgct tctgccccca   1680
cctccccaga acagcgtccc ccattatgcc gaggctgaca ttgttaccct gcagggcgtc   1740
accgggggca acacctatgc tgtgcctgca ctgcccccag gggcagtcgg ggatgggccc   1800
cccagagtgg atttccctcg atctcgactc cgcttcaagg agaagcttgg cgagggccag   1860
tttggggagg tgcacctgtg tgaggtcgac agccctcaag atctggttag tcttgatttc   1920
ccccttaatg tgcgtaaggg acaccctttg ctggtagctg tcaagatctt acggccagat   1980
gccaccaaga atgccaggaa tgatttcctg aaagaggtga agatcatgtc gaggctcaag   2040
gacccaaaca tcattcggct gctgggcgtg tgtgtgcagg acgaccccct ctgcatgatt   2100
actgactaca tggagaacgg cgacctcaac cagttcctca gtgcccacca gctggaggac   2160
aaggcagccg agggggcccc tggggacggg caggctgcgc aggggcccac catcagctac   2220
```

```
ccaatgctgc tgcatgtggc agcccagatc gcctccggca tgcgctatct ggccacactc   2280

aactttgtac atcgggacct ggccacgcgg aactgcctag ttggggaaaa tttcaccatc   2340

aaaatcgcag actttggcat gagccggaac ctctatgctg gggactatta ccgtgtgcag   2400

ggccgggcag tgctgcccat ccgctggatg gcctgggagt gcatcctcat ggggaagttc   2460

acgactgcga gtgacgtgtg ggcctttggt gtgaccctgt gggaggtgct gatgctctgt   2520

agggcccagc cctttgggca gctcaccgac gagcaggtca tcgagaacgc gggggagttc   2580

ttccgggacc agggccggca ggtgtacctg tcccggccgc ctgcctgccc gcagggccta   2640

tatgagctga tgcttcggtg ctggagccgg gagtctgagc agcgaccacc cttttcccag   2700

ctgcatcggt tcctggcaga ggatgcactc aacacggtgt ga                      2742
```

```
<210> SEQ ID NO 12
<211> LENGTH: 913
<212> TYPE: PRT
<213> ORGANISM: Artificial Sequence
<220> FEATURE:
<223> OTHER INFORMATION: Synthetic human DDR1b sequence

<400> SEQUENCE: 12

Met Gly Pro Glu Ala Leu Ser Ser Leu Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270
```

```
Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
    450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
            500                 505                 510

Tyr Arg Leu Leu Leu Ala Thr Tyr Ala Arg Pro Pro Arg Gly Pro Gly
        515                 520                 525

Pro Pro Thr Pro Ala Trp Ala Lys Pro Thr Asn Thr Gln Ala Tyr Ser
    530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575

Leu Gln Gly Val Thr Gly Gly Asn Thr Tyr Ala Val Pro Ala Leu Pro
            580                 585                 590

Pro Gly Ala Val Gly Asp Gly Pro Pro Arg Val Asp Phe Pro Arg Ser
        595                 600                 605

Arg Leu Arg Phe Lys Glu Lys Leu Gly Glu Gly Gln Phe Gly Glu Val
    610                 615                 620

His Leu Cys Glu Val Asp Ser Pro Gln Asp Leu Val Ser Leu Asp Phe
625                 630                 635                 640

Pro Leu Asn Val Arg Lys Gly His Pro Leu Leu Val Ala Val Lys Ile
                645                 650                 655

Leu Arg Pro Asp Ala Thr Lys Asn Ala Arg Asn Asp Phe Leu Lys Glu
            660                 665                 670

Val Lys Ile Met Ser Arg Leu Lys Asp Pro Asn Ile Ile Arg Leu Leu
        675                 680                 685
```

```
Gly Val Cys Val Gln Asp Asp Pro Leu Cys Met Ile Thr Asp Tyr Met
    690                 695                 700

Glu Asn Gly Asp Leu Asn Gln Phe Leu Ser Ala His Gln Leu Glu Asp
705                 710                 715                 720

Lys Ala Ala Glu Gly Ala Pro Gly Asp Gly Gln Ala Ala Gln Gly Pro
                725                 730                 735

Thr Ile Ser Tyr Pro Met Leu Leu His Val Ala Ala Gln Ile Ala Ser
            740                 745                 750

Gly Met Arg Tyr Leu Ala Thr Leu Asn Phe Val His Arg Asp Leu Ala
        755                 760                 765

Thr Arg Asn Cys Leu Val Gly Glu Asn Phe Thr Ile Lys Ile Ala Asp
    770                 775                 780

Phe Gly Met Ser Arg Asn Leu Tyr Ala Gly Asp Tyr Tyr Arg Val Gln
785                 790                 795                 800

Gly Arg Ala Val Leu Pro Ile Arg Trp Met Ala Trp Glu Cys Ile Leu
                805                 810                 815

Met Gly Lys Phe Thr Thr Ala Ser Asp Val Trp Ala Phe Gly Val Thr
            820                 825                 830

Leu Trp Glu Val Leu Met Leu Cys Arg Ala Gln Pro Phe Gly Gln Leu
        835                 840                 845

Thr Asp Glu Gln Val Ile Glu Asn Ala Gly Glu Phe Phe Arg Asp Gln
    850                 855                 860

Gly Arg Gln Val Tyr Leu Ser Arg Pro Pro Ala Cys Pro Gln Gly Leu
865                 870                 875                 880

Tyr Glu Leu Met Leu Arg Cys Trp Ser Arg Glu Ser Glu Gln Arg Pro
                885                 890                 895

Pro Phe Ser Gln Leu His Arg Phe Leu Ala Glu Asp Ala Leu Asn Thr
            900                 905                 910

Val
```

<210> SEQ ID NO 13
<211> LENGTH: 2760
<212> TYPE: DNA
<213> ORGANISM: Artificial Sequence
<220> FEATURE:
<223> OTHER INFORMATION: Synthetic human DDR1c sequence

<400> SEQUENCE: 13

```
atgggaccag aggccctgtc atctttactg ctgctgctct tggtggcaag tggagatgct      60

gacatgaagg gacattttga tcctgccaag tgccgctatg ccctgggcat gcaggaccgg     120

accatcccag acagtgacat ctctgcttcc agctcctggt cagattccac tgccgcccgc     180

cacagcaggt tggagagcag tgacggggat ggggcctggt gccccgcagg gtcggtgttt     240

cccaaggagg aggagtactt gcaggtggat ctacaacgac tgcacctggt ggctctggtg     300

ggcacccagg gacggcatgc cgggggcctg ggcaaggagt tctcccggag ctaccggctg     360

cgttactccc gggatggtcg ccgctggatg ggctggaagg accgctgggg tcaggaggtg     420

atctcaggca atgaggaccc tgagggagtg gtgctgaagg accttgggcc ccccatggtt     480

gcccgactgg ttcgcttcta cccccgggct gaccgggtca tgagcgtctg tctgcgggta     540

gagctctatg gctgcctctg gagggatgga ctcctgtctt acaccgcccc tgtggggcag     600

acaatgtatt tatctgaggc cgtgtacctc aacgactcca cctatgacgg acataccgtg     660

ggcggactgc agtatggggg tctgggccag ctggcagatg gtgtggtggg gctggatgac     720

tttaggaaga gtcaggagct gcgggtctgg ccaggctatg actatgtggg atggagcaac     780
```

```
cacagcttct ccagtggcta tgtggagatg gagtttgagt ttgaccggct gagggccttc    840

caggctatgc aggtccactg taacaacatg cacacgctgg gagcccgtct gcctggcggg    900

gtggaatgtc gcttccggcg tggccctgcc atggcctggg agggggagcc catgcgccac    960

aacctagggg gcaacctggg ggaccccaga gcccgggctg tctcagtgcc ccttggcggc   1020

cgtgtggctc gctttctgca gtgccgcttc ctctttgcgg ggccctggtt actcttcagc   1080

gaaatctcct tcatctctga tgtggtgaac aattcctctc cggcactggg aggcaccttc   1140

ccgccagccc cctggtggcc gcctggccca cctcccacca acttcagcag cttggagctg   1200

gagcccagag gccagcagcc cgtggccaag gccgagggga gcccgaccgc catcctcatc   1260

ggctgcctgg tggccatcat cctgctcctg ctgctcatca ttgccctcat gctctggcgg   1320

ctgcactggc gcaggctcct cagcaaggct gaacggaggg tgttggaaga ggagctgacg   1380

gttcacctct ctgtccctgg ggacactatc ctcatcaaca accgcccagg tcctagagag   1440

ccacccccgt accaggagcc ccggcctcgt gggaatccgc cccactccgc tccctgtgtc   1500

cccaatggct ctgcgttgct gctctccaat ccagcctacc gcctccttct ggccacttac   1560

gcccgtcccc ctcgaggccc gggccccccc acacccgcct gggccaaacc caccaacacc   1620

caggcctaca gtggggacta tatggagcct gagaagccag gcgccccgct tctgccccca   1680

cctccccaga acagcgtccc ccattatgcc gaggctgaca ttgttaccct gcagggcgtc   1740

accgggggca acacctatgc tgtgcctgca ctgcccccag ggcagtcggg ggatgggccc   1800

cccagagtgg atttccctcg atctcgactc cgcttcaagg agaagcttgg cgagggccag   1860

tttggggagg tgcacctgtg tgaggtcgac agccctcaag atctggttag tcttgatttc   1920

ccccttaatg tgcgtaaggg acaccctttg ctggtagctg tcaagatctt acggccagat   1980

gccaccaaga atgccagctt ctccttgttc tccaggaatg atttcctgaa agaggtgaag   2040

atcatgtcga ggctcaagga cccaaacatc attcggctgc tgggcgtgtg tgtgcaggac   2100

gaccccctct gcatgattac tgactacatg gagaacggcg acctcaacca gttcctcagt   2160

gcccaccagc tggaggacaa ggcagccgag gggccccctg gggacgggca ggctgcgcag   2220

gggcccacca tcagctaccc aatgctgctg catgtggcag cccagatcgc ctccggcatg   2280

cgctatctgg ccacactcaa ctttgtacat cgggacctgg ccacgcggaa ctgcctagtt   2340

ggggaaaatt tcaccatcaa aatcgcagac tttggcatga gccggaacct ctatgctggg   2400

gactattacc gtgtgcaggg ccgggcagtg ctgcccatcc gctggatggc ctgggagtgc   2460

atcctcatgg ggaagttcac gactgcgagt gacgtgtggg cctttggtgt gaccctgtgg   2520

gaggtgctga tgctctgtag ggcccagccc tttgggcagc tcaccgacga gcaggtcatc   2580

gagaacgcgg gggagttctt ccgggaccag ggccggcagg tgtacctgtc ccggccgcct   2640

gcctgcccgc agggcctata tgagctgatg cttcggtgct ggagccggga gtctgagcag   2700

cgaccaccct tttcccagct gcatcggttc ctggcagagg atgcactcaa cacggtgtga   2760
```

<210> SEQ ID NO 14
<211> LENGTH: 919
<212> TYPE: PRT
<213> ORGANISM: Artificial Sequence
<220> FEATURE:
<223> OTHER INFORMATION: Synthetic human DDR1c sequence

<400> SEQUENCE: 14

```
Met Gly Pro Glu Ala Leu Ser Ser Leu Leu Leu Leu Leu Leu Val Ala
1               5                   10                  15
```

```
Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
        35                  40                  45

Ala Ser Ser Ser Trp Ser Asp Ser Thr Ala Ala Arg His Ser Arg Leu
    50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
    210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
    290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
    370                 375                 380

Trp Trp Pro Pro Gly Pro Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430
```

```
Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
    450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
            500                 505                 510

Tyr Arg Leu Leu Leu Ala Thr Tyr Ala Arg Pro Pro Arg Gly Pro Gly
        515                 520                 525

Pro Pro Thr Pro Ala Trp Ala Lys Pro Thr Asn Thr Gln Ala Tyr Ser
    530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575

Leu Gln Gly Val Thr Gly Gly Asn Thr Tyr Ala Val Pro Ala Leu Pro
            580                 585                 590

Pro Gly Ala Val Gly Asp Gly Pro Pro Arg Val Asp Phe Pro Arg Ser
        595                 600                 605

Arg Leu Arg Phe Lys Glu Lys Leu Gly Glu Gly Gln Phe Gly Glu Val
    610                 615                 620

His Leu Cys Glu Val Asp Ser Pro Gln Asp Leu Val Ser Leu Asp Phe
625                 630                 635                 640

Pro Leu Asn Val Arg Lys Gly His Pro Leu Leu Val Ala Val Lys Ile
                645                 650                 655

Leu Arg Pro Asp Ala Thr Lys Asn Ala Ser Phe Ser Leu Phe Ser Arg
            660                 665                 670

Asn Asp Phe Leu Lys Glu Val Lys Ile Met Ser Arg Leu Lys Asp Pro
        675                 680                 685

Asn Ile Ile Arg Leu Leu Gly Val Cys Val Gln Asp Asp Pro Leu Cys
    690                 695                 700

Met Ile Thr Asp Tyr Met Glu Asn Gly Asp Leu Asn Gln Phe Leu Ser
705                 710                 715                 720

Ala His Gln Leu Glu Asp Lys Ala Ala Glu Gly Ala Pro Gly Asp Gly
                725                 730                 735

Gln Ala Ala Gln Gly Pro Thr Ile Ser Tyr Pro Met Leu Leu His Val
            740                 745                 750

Ala Ala Gln Ile Ala Ser Gly Met Arg Tyr Leu Ala Thr Leu Asn Phe
        755                 760                 765

Val His Arg Asp Leu Ala Thr Arg Asn Cys Leu Val Gly Glu Asn Phe
    770                 775                 780

Thr Ile Lys Ile Ala Asp Phe Gly Met Ser Arg Asn Leu Tyr Ala Gly
785                 790                 795                 800

Asp Tyr Tyr Arg Val Gln Gly Arg Ala Val Leu Pro Ile Arg Trp Met
                805                 810                 815

Ala Trp Glu Cys Ile Leu Met Gly Lys Phe Thr Thr Ala Ser Asp Val
            820                 825                 830

Trp Ala Phe Gly Val Thr Leu Trp Glu Val Leu Met Leu Cys Arg Ala
        835                 840                 845

Gln Pro Phe Gly Gln Leu Thr Asp Glu Gln Val Ile Glu Asn Ala Gly
```

```
    850                 855                 860

Glu Phe Phe Arg Asp Gln Gly Arg Gln Val Tyr Leu Ser Arg Pro Pro
865                 870                 875                 880

Ala Cys Pro Gln Gly Leu Tyr Glu Leu Met Leu Arg Cys Trp Ser Arg
                885                 890                 895

Glu Ser Glu Gln Arg Pro Pro Phe Ser Gln Leu His Arg Phe Leu Ala
            900                 905                 910

Glu Asp Ala Leu Asn Thr Val
        915


<210> SEQ ID NO 15
<211> LENGTH: 397
<212> TYPE: PRT
<213> ORGANISM: Artificial Sequence
<220> FEATURE:
<223> OTHER INFORMATION: Synthetic human DDR1 mature ECD sequence

<400> SEQUENCE: 15

Asp Met Lys Gly His Phe Asp Pro Ala Lys Cys Arg Tyr Ala Leu Gly
1               5                   10                  15

Met Gln Asp Arg Thr Ile Pro Asp Ser Asp Ile Ser Ala Ser Ser Ser
            20                  25                  30

Trp Ser Asp Ser Thr Ala Ala Arg His Ser Arg Leu Glu Ser Ser Asp
        35                  40                  45

Gly Asp Gly Ala Trp Cys Pro Ala Gly Ser Val Phe Pro Lys Glu Glu
    50                  55                  60

Glu Tyr Leu Gln Val Asp Leu Gln Arg Leu His Leu Val Ala Leu Val
65                  70                  75                  80

Gly Thr Gln Gly Arg His Ala Gly Gly Leu Gly Lys Glu Phe Ser Arg
                85                  90                  95

Ser Tyr Arg Leu Arg Tyr Ser Arg Asp Gly Arg Arg Trp Met Gly Trp
            100                 105                 110

Lys Asp Arg Trp Gly Gln Glu Val Ile Ser Gly Asn Glu Asp Pro Glu
        115                 120                 125

Gly Val Val Leu Lys Asp Leu Gly Pro Pro Met Val Ala Arg Leu Val
    130                 135                 140

Arg Phe Tyr Pro Arg Ala Asp Arg Val Met Ser Val Cys Leu Arg Val
145                 150                 155                 160

Glu Leu Tyr Gly Cys Leu Trp Arg Asp Gly Leu Leu Ser Tyr Thr Ala
                165                 170                 175

Pro Val Gly Gln Thr Met Tyr Leu Ser Glu Ala Val Tyr Leu Asn Asp
            180                 185                 190

Ser Thr Tyr Asp Gly His Thr Val Gly Gly Leu Gln Tyr Gly Gly Leu
        195                 200                 205

Gly Gln Leu Ala Asp Gly Val Val Gly Leu Asp Asp Phe Arg Lys Ser
    210                 215                 220

Gln Glu Leu Arg Val Trp Pro Gly Tyr Asp Tyr Val Gly Trp Ser Asn
225                 230                 235                 240

His Ser Phe Ser Ser Gly Tyr Val Glu Met Glu Phe Glu Phe Asp Arg
                245                 250                 255

Leu Arg Ala Phe Gln Ala Met Gln Val His Cys Asn Asn Met His Thr
            260                 265                 270

Leu Gly Ala Arg Leu Pro Gly Gly Val Glu Cys Arg Phe Arg Arg Gly
        275                 280                 285

Pro Ala Met Ala Trp Glu Gly Glu Pro Met Arg His Asn Leu Gly Gly
```

```
    290                 295                 300

Asn Leu Gly Asp Pro Arg Ala Arg Ala Val Ser Val Pro Leu Gly Gly
305                 310                 315                 320

Arg Val Ala Arg Phe Leu Gln Cys Arg Phe Leu Phe Ala Gly Pro Trp
                325                 330                 335

Leu Leu Phe Ser Glu Ile Ser Phe Ile Ser Asp Val Val Asn Asn Ser
            340                 345                 350

Ser Pro Ala Leu Gly Gly Thr Phe Pro Pro Ala Pro Trp Trp Pro Pro
        355                 360                 365

Gly Pro Pro Pro Thr Asn Phe Ser Ser Leu Glu Leu Glu Pro Arg Gly
    370                 375                 380

Gln Gln Pro Val Ala Lys Ala Glu Gly Ser Pro Thr Ala
385                 390                 395
```

<210> SEQ ID NO 16
<211> LENGTH: 1371
<212> TYPE: DNA
<213> ORGANISM: Artificial Sequence
<220> FEATURE:
<223> OTHER INFORMATION: Synthetic 20M102 Heavy chain sequence

<400> SEQUENCE: 16

```
atgaaatgga cctgggtcat cctctttctc ttgtcaggaa ctggaggtgt cctctctgag     60

gtccagctgc aacagtctgg atctgagctg gtgaagcctg gggcttcagt gaagatgtcc    120

tgcaaggctt ctggatacac cttcactgac tacttcatga agtgggtgaa gcagagccat    180

ggaaagagcc ttgaatggat tggagatatt aatcccaaca atggtgatac tttctacatc    240

cagaagttca agggcaaggc cactttgact gtagacaaat cctccagtac agcctacatg    300

cagctcaaca gcctgacatc tgaggactct gcagtctatt actgttcaag agaccttgct    360

tactggggcc aagggactct ggtcgctgtc tcctcagcca aaacgacacc cccatctgtc    420

tatccactgg cccctggatc tgctgcccaa actaactcca tggtgaccct gggatgcctg    480

gtcaagggct atttccctga gccagtgaca gtgacctgga actctggatc cctgtccagc    540

ggtgtgcaca ccttcccagc tgtcctgcag tctgacctct acactctgag cagctcagtg    600

actgtcccct ccagcacctg gcccagcgag accgtcacct gcaacgttgc ccacccggcc    660

agcagcacca aggtggacaa gaaaattgtg cccagggatt gtggttgtaa gccttgcata    720

tgtacagtcc cagaagtatc atctgtcttc atcttccccc caaagcccaa ggatgtgctc    780

accattactc tgactcctaa ggtcacgtgt gttgtggtag acatcagcaa ggatgatccc    840

gaggtccagt tcagctggtt tgtagatgat gtggaggtgc acacagctca gacgcaaccc    900

cgggaggagc agttcaacag cactttccgc tcagtcagtg aacttcccat catgcaccag    960

gactggctca atggcaagga gttcaaatgc agggtcaaca gtgcagcttt ccctgccccc   1020

atcgagaaaa ccatctccaa aaccaaaggc agaccgaagg ctccacaggt gtacaccatt   1080

ccacctccca aggagcagat ggccaaggat aaagtcagtc tgacctgcat gataacagac   1140

ttcttccctg aagacattac tgtggagtgg cagtggaatg ggcagccagc ggagaactac   1200

aagaacactc agcccatcat ggacacagat ggctcttact tcgtctacag caagctcaat   1260

gtgcagaaga gcaactggga ggcaggaaat actttcacct gctctgtgtt acatgagggc   1320

ctgcacaacc accatactga gaagagcctc tcccactctc ctggtaaatg a             1371
```

<210> SEQ ID NO 17
<211> LENGTH: 456

<212> TYPE: PRT
<213> ORGANISM: Artificial Sequence
<220> FEATURE:
<223> OTHER INFORMATION: Synthetic 20M102 Heavy chain sequence

<400> SEQUENCE: 17

```
Met Lys Trp Thr Trp Val Ile Leu Phe Leu Leu Ser Gly Thr Gly Gly
1               5                   10                  15

Val Leu Ser Glu Val Gln Leu Gln Gln Ser Gly Ser Glu Leu Val Lys
            20                  25                  30

Pro Gly Ala Ser Val Lys Met Ser Cys Lys Ala Ser Gly Tyr Thr Phe
        35                  40                  45

Thr Asp Tyr Phe Met Lys Trp Val Lys Gln Ser His Gly Lys Ser Leu
    50                  55                  60

Glu Trp Ile Gly Asp Ile Asn Pro Asn Asn Gly Asp Thr Phe Tyr Ile
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ser Arg Asp Leu Ala Tyr Trp Gly Gln Gly Thr Leu Val
        115                 120                 125

Ala Val Ser Ser Ala Lys Thr Thr Pro Pro Ser Val Tyr Pro Leu Ala
    130                 135                 140

Pro Gly Ser Ala Ala Gln Thr Asn Ser Met Val Thr Leu Gly Cys Leu
145                 150                 155                 160

Val Lys Gly Tyr Phe Pro Glu Pro Val Thr Val Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Pro Ser Ser Thr Trp Pro
        195                 200                 205

Ser Glu Thr Val Thr Cys Asn Val Ala His Pro Ala Ser Ser Thr Lys
    210                 215                 220

Val Asp Lys Lys Ile Val Pro Arg Asp Cys Gly Cys Lys Pro Cys Ile
225                 230                 235                 240

Cys Thr Val Pro Glu Val Ser Ser Val Phe Ile Phe Pro Pro Lys Pro
                245                 250                 255

Lys Asp Val Leu Thr Ile Thr Leu Thr Pro Lys Val Thr Cys Val Val
            260                 265                 270

Val Asp Ile Ser Lys Asp Asp Pro Glu Val Gln Phe Ser Trp Phe Val
        275                 280                 285

Asp Asp Val Glu Val His Thr Ala Gln Thr Gln Pro Arg Glu Glu Gln
    290                 295                 300

Phe Asn Ser Thr Phe Arg Ser Val Ser Glu Leu Pro Ile Met His Gln
305                 310                 315                 320

Asp Trp Leu Asn Gly Lys Glu Phe Lys Cys Arg Val Asn Ser Ala Ala
                325                 330                 335

Phe Pro Ala Pro Ile Glu Lys Thr Ile Ser Lys Thr Lys Gly Arg Pro
            340                 345                 350

Lys Ala Pro Gln Val Tyr Thr Ile Pro Pro Pro Lys Glu Gln Met Ala
        355                 360                 365

Lys Asp Lys Val Ser Leu Thr Cys Met Ile Thr Asp Phe Phe Pro Glu
    370                 375                 380
```

```
Asp Ile Thr Val Glu Trp Gln Trp Asn Gly Gln Pro Ala Glu Asn Tyr
385                 390                 395                 400

Lys Asn Thr Gln Pro Ile Met Asp Thr Asp Gly Ser Tyr Phe Val Tyr
                405                 410                 415

Ser Lys Leu Asn Val Gln Lys Ser Asn Trp Glu Ala Gly Asn Thr Phe
            420                 425                 430

Thr Cys Ser Val Leu His Glu Gly Leu His Asn His His Thr Glu Lys
        435                 440                 445

Ser Leu Ser His Ser Pro Gly Lys
    450                 455


<210> SEQ ID NO 18
<211> LENGTH: 711
<212> TYPE: DNA
<213> ORGANISM: Artificial Sequence
<220> FEATURE:
<223> OTHER INFORMATION: Synthetic 20M102 Light chain sequence

<400> SEQUENCE: 18

atgaagttgc ctgttaggct gttggtgctc tggattcagg aaaccaacgg tgatgttgtg      60

atgacccaga ctccactcac tttgtcggtt aacattggac aaccagcctc tatctcttgc     120

aagtcaagtc agagcctctt atatagtaat gggaaaacct atttgaattg gttattacag     180

aggccaggcc agtctccaag gcgcctaatc tatcaggtgt ctaaactgga ctctggagtc     240

cctgacaggt tcactggcag tggatcagga acagatttta cattgaaaat cagcagagtg     300

gaggctgagg atttgggagt ttattactgc gtgcaaggta cagattttcc tcagacgttc     360

ggtggaggca ccaagctgga aatcaaacgg gctgatgctg caccaactgt atccatcttc     420

ccaccatcca gtgagcagtt aacatctgga ggtgcctcag tcgtgtgctt cttgaacaac     480

ttctacccca aagacatcaa tgtcaagtgg aagattgatg gcagtgaacg acaaaatggc     540

gtcctgaaca gttggactga tcaggacagc aaagacagca cctacagcat gagcagcacc     600

ctcacgttga ccaaggacga gtatgaacga cataacagct atacctgtga ggccactcac     660

aagacatcaa cttcacccat cgtcaagagc ttcaacagga atgagtgtta g             711


<210> SEQ ID NO 19
<211> LENGTH: 236
<212> TYPE: PRT
<213> ORGANISM: Artificial Sequence
<220> FEATURE:
<223> OTHER INFORMATION: Synthetic 20M102 Light chain sequence

<400> SEQUENCE: 19

Met Lys Leu Pro Val Arg Leu Leu Val Leu Trp Ile Gln Glu Thr Asn
1               5                   10                  15

Gly Asp Val Val Met Thr Gln Thr Pro Leu Thr Leu Ser Val Asn Ile
            20                  25                  30

Gly Gln Pro Ala Ser Ile Ser Cys Lys Ser Ser Gln Ser Leu Leu Tyr
        35                  40                  45

Ser Asn Gly Lys Thr Tyr Leu Asn Trp Leu Leu Gln Arg Pro Gly Gln
    50                  55                  60

Ser Pro Arg Arg Leu Ile Tyr Gln Val Ser Lys Leu Asp Ser Gly Val
65                  70                  75                  80

Pro Asp Arg Phe Thr Gly Ser Gly Ser Gly Thr Asp Phe Thr Leu Lys
                85                  90                  95

Ile Ser Arg Val Glu Ala Glu Asp Leu Gly Val Tyr Tyr Cys Val Gln
            100                 105                 110
```

```
Gly Thr Asp Phe Pro Gln Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235


<210> SEQ ID NO 20
<211> LENGTH: 390
<212> TYPE: DNA
<213> ORGANISM: Artificial Sequence
<220> FEATURE:
<223> OTHER INFORMATION: Synthetic 20M102 Heavy chain variable region

<400> SEQUENCE: 20

atgaaatgga cctgggtcat cctctttctc ttgtcaggaa ctggaggtgt cctctctgag     60

gtccagctgc aacagtctgg atctgagctg gtgaagcctg gggcttcagt gaagatgtcc    120

tgcaaggctt ctggatacac cttcactgac tacttcatga agtgggtgaa gcagagccat    180

ggaaagagcc ttgaatggat tggagatatt aatcccaaca atggtgatac tttctacatc    240

cagaagttca agggcaaggc cactttgact gtagacaaat cctccagtac agcctacatg    300

cagctcaaca gcctgacatc tgaggactct gcagtctatt actgttcaag agaccttgct    360

tactggggcc aagggactct ggtcgctgtc                                      390


<210> SEQ ID NO 21
<211> LENGTH: 130
<212> TYPE: PRT
<213> ORGANISM: Artificial Sequence
<220> FEATURE:
<223> OTHER INFORMATION: Synthetic 20M102 Heavy chain variable region

<400> SEQUENCE: 21

Met Lys Trp Thr Trp Val Ile Leu Phe Leu Leu Ser Gly Thr Gly Gly
1               5                   10                  15

Val Leu Ser Glu Val Gln Leu Gln Gln Ser Gly Ser Glu Leu Val Lys
            20                  25                  30

Pro Gly Ala Ser Val Lys Met Ser Cys Lys Ala Ser Gly Tyr Thr Phe
        35                  40                  45

Thr Asp Tyr Phe Met Lys Trp Val Lys Gln Ser His Gly Lys Ser Leu
    50                  55                  60

Glu Trp Ile Gly Asp Ile Asn Pro Asn Asn Gly Asp Thr Phe Tyr Ile
65                  70                  75                  80

Gln Lys Phe Lys Gly Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110
```

```
Tyr Tyr Cys Ser Arg Asp Leu Ala Tyr Trp Gly Gln Gly Thr Leu Val
        115                 120                 125

Ala Val
    130


<210> SEQ ID NO 22
<211> LENGTH: 10
<212> TYPE: PRT
<213> ORGANISM: Artificial Sequence
<220> FEATURE:
<223> OTHER INFORMATION: Synthetic 20M102 Heavy chain CDR1 sequence

<400> SEQUENCE: 22

Gly Tyr Thr Phe Thr Asp Tyr Phe Met Lys
1               5                   10


<210> SEQ ID NO 23
<211> LENGTH: 17
<212> TYPE: PRT
<213> ORGANISM: Artificial Sequence
<220> FEATURE:
<223> OTHER INFORMATION: Synthetic 20M102 Heavy chain CDR2 sequence

<400> SEQUENCE: 23

Asp Ile Asn Pro Asn Asn Gly Asp Thr Phe Tyr Ile Gln Lys Phe Lys
1               5                   10                  15

Gly


<210> SEQ ID NO 24
<211> LENGTH: 6
<212> TYPE: PRT
<213> ORGANISM: Artificial Sequence
<220> FEATURE:
<223> OTHER INFORMATION: Synthetic 20M102 Heavy chain CDR3 sequence

<400> SEQUENCE: 24

Ser Arg Asp Leu Ala Tyr
1               5


<210> SEQ ID NO 25
<211> LENGTH: 369
<212> TYPE: DNA
<213> ORGANISM: Artificial Sequence
<220> FEATURE:
<223> OTHER INFORMATION: Synthetic 20M102 Light chain variable region

<400> SEQUENCE: 25

atgaagttgc ctgttaggct gttggtgctc tggattcagg aaaccaacgg tgatgttgtg     60

atgacccaga ctccactcac tttgtcggtt aacattggac aaccagcctc tatctcttgc    120

aagtcaagtc agagcctctt atatagtaat gggaaaacct atttgaattg gttattacag    180

aggccaggcc agtctccaag gcgcctaatc tatcaggtgt ctaaactgga ctctggagtc    240

cctgacaggt tcactggcag tggatcagga acagatttta cattgaaaat cagcagagtg    300

gaggctgagg atttgggagt ttattactgc gtgcaaggta cagattttcc tcagacgttc    360

ggtggaggc                                                            369


<210> SEQ ID NO 26
<211> LENGTH: 123
<212> TYPE: PRT
<213> ORGANISM: Artificial Sequence
<220> FEATURE:
<223> OTHER INFORMATION: Synthetic 20M102 Light chain variable region
```

<400> SEQUENCE: 26

```
Met Lys Leu Pro Val Arg Leu Leu Val Leu Trp Ile Gln Glu Thr Asn
1               5                   10                  15

Gly Asp Val Val Met Thr Gln Thr Pro Leu Thr Leu Ser Val Asn Ile
            20                  25                  30

Gly Gln Pro Ala Ser Ile Ser Cys Lys Ser Ser Gln Ser Leu Leu Tyr
        35                  40                  45

Ser Asn Gly Lys Thr Tyr Leu Asn Trp Leu Leu Gln Arg Pro Gly Gln
    50                  55                  60

Ser Pro Arg Arg Leu Ile Tyr Gln Val Ser Lys Leu Asp Ser Gly Val
65                  70                  75                  80

Pro Asp Arg Phe Thr Gly Ser Gly Ser Gly Thr Asp Phe Thr Leu Lys
                85                  90                  95

Ile Ser Arg Val Glu Ala Glu Asp Leu Gly Val Tyr Tyr Cys Val Gln
            100                 105                 110

Gly Thr Asp Phe Pro Gln Thr Phe Gly Gly Gly
        115                 120
```

<210> SEQ ID NO 27
<211> LENGTH: 16
<212> TYPE: PRT
<213> ORGANISM: Artificial Sequence
<220> FEATURE:
<223> OTHER INFORMATION: Synthetic 20M102 Light chain CDR1 sequence

<400> SEQUENCE: 27

```
Lys Ser Ser Gln Ser Leu Leu Tyr Ser Asn Gly Lys Thr Tyr Leu Asn
1               5                   10                  15
```

<210> SEQ ID NO 28
<211> LENGTH: 7
<212> TYPE: PRT
<213> ORGANISM: Artificial Sequence
<220> FEATURE:
<223> OTHER INFORMATION: Synthetic 20M102 Light chain CDR2 sequence

<400> SEQUENCE: 28

```
Gln Val Ser Lys Leu Asp Ser
1               5
```

<210> SEQ ID NO 29
<211> LENGTH: 9
<212> TYPE: PRT
<213> ORGANISM: Artificial Sequence
<220> FEATURE:
<223> OTHER INFORMATION: Synthetic 20M102 Light chain CDR3 sequence

<400> SEQUENCE: 29

```
Val Gln Gly Thr Asp Phe Pro Gln Thr
1               5
```

<210> SEQ ID NO 30
<211> LENGTH: 13
<212> TYPE: PRT
<213> ORGANISM: Artificial Sequence
<220> FEATURE:
<223> OTHER INFORMATION: Synthetic partial DDR1 sequence

<400> SEQUENCE: 30

```
Ser Ala Ser Ser Ser Trp Ser Asp Ser Thr Ala Ala Arg
1               5                   10
```

<210> SEQ ID NO 31
<211> LENGTH: 13
<212> TYPE: PRT
<213> ORGANISM: Artificial Sequence
<220> FEATURE:
<223> OTHER INFORMATION: Synthetic partial DDR1 sequence

<400> SEQUENCE: 31

```
Ser Ala Ser Ser Ser Ala Ser Asp Ser Thr Ala Ala Arg
1               5                   10
```

<210> SEQ ID NO 32
<211> LENGTH: 333
<212> TYPE: DNA
<213> ORGANISM: Artificial Sequence
<220> FEATURE:
<223> OTHER INFORMATION: Synthetic 20M102 Heavy chain variable region

<400> SEQUENCE: 32

```
gaggtccagc tgcaacagtc tggatctgag ctggtgaagc ctggggcttc agtgaagatg     60

tcctgcaagg cttctggata caccttcact gactacttca tgaagtgggt gaagcagagc    120

catggaaaga gccttgaatg gattggagat attaatccca acaatggtga tactttctac    180

atccagaagt tcaagggcaa ggccactttg actgtagaca aatcctccag tacagcctac    240

atgcagctca acagcctgac atctgaggac tctgcagtct attactgttc aagagacctt    300

gcttactggg gccaagggac tctggtcgct gtc                                 333
```

<210> SEQ ID NO 33
<211> LENGTH: 111
<212> TYPE: PRT
<213> ORGANISM: Artificial Sequence
<220> FEATURE:
<223> OTHER INFORMATION: Synthetic 20M102 Heavy chain variable region

<400> SEQUENCE: 33

```
Glu Val Gln Leu Gln Gln Ser Gly Ser Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Phe Met Lys Trp Val Lys Gln Ser His Gly Lys Ser Leu Glu Trp Ile
        35                  40                  45

Gly Asp Ile Asn Pro Asn Asn Gly Asp Thr Phe Tyr Ile Gln Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ser Arg Asp Leu Ala Tyr Trp Gly Gln Gly Thr Leu Val Ala Val
            100                 105                 110
```

<210> SEQ ID NO 34
<211> LENGTH: 318
<212> TYPE: DNA
<213> ORGANISM: Artificial Sequence
<220> FEATURE:
<223> OTHER INFORMATION: Synthetic 20M102 Light chain variable region

<400> SEQUENCE: 34

```
gatgttgtga tgacccagac tccactcact ttgtcggtta acattggaca accagcctct     60

atctcttgca agtcaagtca gagcctctta tatagtaatg ggaaaaccta tttgaattgg    120
```

ttattacaga ggccaggcca gtctccaagg cgcctaatct atcaggtgtc taaactggac 180
tctggagtcc ctgacaggtt cactggcagt ggatcaggaa cagattttac attgaaaatc 240
agcagagtgg aggctgagga tttgggagtt tattactgcg tgcaaggtac agattttcct 300
cagacgttcg gtggaggc 318

<210> SEQ ID NO 35
<211> LENGTH: 106
<212> TYPE: PRT
<213> ORGANISM: Artificial Sequence
<220> FEATURE:
<223> OTHER INFORMATION: Synthetic 20M102 Light chain variable region

<400> SEQUENCE: 35

Asp Val Val Met Thr Gln Thr Pro Leu Thr Leu Ser Val Asn Ile Gly
1 5 10 15

Gln Pro Ala Ser Ile Ser Cys Lys Ser Ser Gln Ser Leu Leu Tyr Ser
20 25 30

Asn Gly Lys Thr Tyr Leu Asn Trp Leu Leu Gln Arg Pro Gly Gln Ser
35 40 45

Pro Arg Arg Leu Ile Tyr Gln Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Val Tyr Tyr Cys Val Gln Gly
85 90 95

Thr Asp Phe Pro Gln Thr Phe Gly Gly Gly
100 105

<210> SEQ ID NO 36
<211> LENGTH: 2691
<212> TYPE: DNA
<213> ORGANISM: Artificial Sequence
<220> FEATURE:
<223> OTHER INFORMATION: Synthetic human DDR1-FLAG construct

<400> SEQUENCE: 36
atgtctgcac ttctgatcct agctcttgtt ggagctgcag ttgctgacta caaagaccat 60
gacggtgatt ataaagatca tgacatcgat tacaaggatg acgatgacaa ggcgatcgcg 120
gacatgaagg gacattttga tcctgccaag tgccgctatg ccctgggcat gcaggaccgg 180
accatcccag acagtgacat ctctgcttcc agctcctggt cagattccac tgccgcccgc 240
cacagcaggt tggagagcag tgacggggat ggggcctggt gccccgcagg gtcggtgttt 300
cccaaggagg aggagtactt gcaggtggat ctacaacgac tgcacctggt ggctctggtg 360
ggcacccagg gacggcatgc cgggggcctg ggcaaggagt tctcccggag ctaccggctg 420
cgttactccc gggatggtcg ccgctggatg ggctggaagg accgctgggg tcaggaggtg 480
atctcaggca atgaggaccc tgagggagtg gtgctgaagg accttgggcc ccccatggtt 540
gcccgactgg ttcgcttcta cccccgggct gaccgggtca tgagcgtctg tctgcgggta 600
gagctctatg gctgcctctg gagggatgga ctcctgtctt acactgcccc tgtggggcag 660
acaatgtatt tatctgaggc cgtgtacctc aacgactcca cctatgacgg acataccgtg 720
ggcggactgc agtatggggg tctgggccag ctggcagatg gtgtggtggg gctggatgac 780
tttaggaaga gtcaggagct gcgggtctgg ccaggctatg actatgtggg atggagcaac 840
cacagcttct ccagtggcta tgtggagatg gagtttgagt ttgaccggct gagggccttc 900

```
caggctatgc aggtccactg taacaacatg cacacgctgg gagcccgtct gcctggcggg    960

gtggaatgtc gcttccggcg tggccctgcc atggcctggg agggggagcc catgcgccac   1020

aacctagggg gcaacctggg ggaccccaga gcccgggctg tctcagtgcc ccttggcggc   1080

cgtgtggctc gctttctgca gtgccgcttc ctctttgcgg ggccctggtt actcttcagc   1140

gaaatctcct tcatctctga tgtggtgaac aattcctctc cggcactggg aggcaccttc   1200

ccgccagccc cctggtggcc gcctggccca cctcccacca acttcagcag cttggagctg   1260

gagcccagag gccagcagcc cgtggccaag gccgagggga gcccgaccgc catcctcatc   1320

ggctgcctgg tggccatcat cctgctcctg ctgctcatca ttgccctcat gctctggcgg   1380

ctgcactggc gcaggctcct cagcaaggct gaacggaggg tgttggaaga ggagctgacg   1440

gttcacctct ctgtccctgg ggacactatc ctcatcaaca accgcccagg tcctagagag   1500

ccacccccgt accaggagcc ccggcctcgt gggaatccgc cccactccgc tccctgtgtc   1560

cccaatggct ctgcctacag tggggactat atggagcctg agaagccagg cgccccgctt   1620

ctgcccccac ctccccagaa cagcgtcccc cattatgccg aggctgacat tgttaccctg   1680

cagggcgtca ccgggggcaa cacctatgct gtgcctgcac tgcccccagg ggcagtcggg   1740

gatgggcccc ccagagtgga tttccctcga tctcgactcc gcttcaagga gaagcttggc   1800

gagggccagt ttggggaggt gcacctgtgt gaggtcgaca gccctcaaga tctggttagt   1860

cttgatttcc cccttaatgt gcgtaaggga cacccttttgc tggtagctgt caagatctta   1920

cggccagatg ccaccaagaa tgccaggaat gatttcctga aagaggtgaa gatcatgtcg   1980

aggctcaagg acccaaacat cattcggctg ctgggcgtgt gtgtgcagga cgacccccctc   2040

tgcatgatta ctgactacat ggagaacggc gacctcaacc agttcctcag tgcccaccag   2100

ctggaggaca aggcagccga gggggcccct ggggacgggc aggctgcgca ggggcccacc   2160

atcagctacc caatgctgct gcatgtggca gcccagatcg cctccggcat gcgctatctg   2220

gccacactca actttgtaca tcgggacctg gccacgcgga actgcctagt tggggaaaat   2280

ttcaccatca aaatcgcaga ctttggcatg agccggaacc tctatgctgg ggactattac   2340

cgtgtgcagg gccgggcagt gctgcccatc cgctggatgg cctgggagtg catcctcatg   2400

gggaagttca cgactgcgag tgacgtgtgg gcctttggtg tgaccctgtg ggaggtgctg   2460

atgctctgta gggcccagcc ctttgggcag ctcaccgacg agcaggtcat cgagaacgcg   2520

ggggagttct tccgggacca gggccggcag gtgtacctgt cccggccgcc tgcctgcccg   2580

cagggcctat atgagctgat gcttcggtgc tggagccggg agtctgagca gcgaccaccc   2640

ttttcccagc tgcatcggtt cctggcagag gatgcactca acacggtgtg a            2691
```

<210> SEQ ID NO 37
<211> LENGTH: 896
<212> TYPE: PRT
<213> ORGANISM: Artificial Sequence
<220> FEATURE:
<223> OTHER INFORMATION: Synthetic human DDR1-FLAG construct

<400> SEQUENCE: 37

```
Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ala Ile Ala Asp Met Lys Gly His Phe Asp Pro
        35                  40                  45
```

```
Ala Lys Cys Arg Tyr Ala Leu Gly Met Gln Asp Arg Thr Ile Pro Asp
    50                  55                  60

Ser Asp Ile Ser Ala Ser Ser Ser Trp Ser Asp Ser Thr Ala Ala Arg
65                  70                  75                  80

His Ser Arg Leu Glu Ser Ser Asp Gly Asp Gly Ala Trp Cys Pro Ala
                85                  90                  95

Gly Ser Val Phe Pro Lys Glu Glu Glu Tyr Leu Gln Val Asp Leu Gln
            100                 105                 110

Arg Leu His Leu Val Ala Leu Val Gly Thr Gln Gly Arg His Ala Gly
        115                 120                 125

Gly Leu Gly Lys Glu Phe Ser Arg Ser Tyr Arg Leu Arg Tyr Ser Arg
    130                 135                 140

Asp Gly Arg Arg Trp Met Gly Trp Lys Asp Arg Trp Gly Gln Glu Val
145                 150                 155                 160

Ile Ser Gly Asn Glu Asp Pro Glu Gly Val Val Leu Lys Asp Leu Gly
                165                 170                 175

Pro Pro Met Val Ala Arg Leu Val Arg Phe Tyr Pro Arg Ala Asp Arg
            180                 185                 190

Val Met Ser Val Cys Leu Arg Val Glu Leu Tyr Gly Cys Leu Trp Arg
        195                 200                 205

Asp Gly Leu Leu Ser Tyr Thr Ala Pro Val Gly Gln Thr Met Tyr Leu
    210                 215                 220

Ser Glu Ala Val Tyr Leu Asn Asp Ser Thr Tyr Asp Gly His Thr Val
225                 230                 235                 240

Gly Gly Leu Gln Tyr Gly Gly Leu Gly Gln Leu Ala Asp Gly Val Val
                245                 250                 255

Gly Leu Asp Asp Phe Arg Lys Ser Gln Glu Leu Arg Val Trp Pro Gly
            260                 265                 270

Tyr Asp Tyr Val Gly Trp Ser Asn His Ser Phe Ser Ser Gly Tyr Val
        275                 280                 285

Glu Met Glu Phe Glu Phe Asp Arg Leu Arg Ala Phe Gln Ala Met Gln
    290                 295                 300

Val His Cys Asn Asn Met His Thr Leu Gly Ala Arg Leu Pro Gly Gly
305                 310                 315                 320

Val Glu Cys Arg Phe Arg Arg Gly Pro Ala Met Ala Trp Glu Gly Glu
                325                 330                 335

Pro Met Arg His Asn Leu Gly Gly Asn Leu Gly Asp Pro Arg Ala Arg
            340                 345                 350

Ala Val Ser Val Pro Leu Gly Gly Arg Val Ala Arg Phe Leu Gln Cys
        355                 360                 365

Arg Phe Leu Phe Ala Gly Pro Trp Leu Leu Phe Ser Glu Ile Ser Phe
    370                 375                 380

Ile Ser Asp Val Val Asn Asn Ser Ser Pro Ala Leu Gly Gly Thr Phe
385                 390                 395                 400

Pro Pro Ala Pro Trp Trp Pro Pro Gly Pro Pro Pro Thr Asn Phe Ser
                405                 410                 415

Ser Leu Glu Leu Glu Pro Arg Gly Gln Gln Pro Val Ala Lys Ala Glu
            420                 425                 430

Gly Ser Pro Thr Ala Ile Leu Ile Gly Cys Leu Val Ala Ile Ile Leu
        435                 440                 445

Leu Leu Leu Leu Ile Ile Ala Leu Met Leu Trp Arg Leu His Trp Arg
    450                 455                 460
```

```
Arg Leu Leu Ser Lys Ala Glu Arg Arg Val Leu Glu Glu Glu Leu Thr
465                 470                 475                 480

Val His Leu Ser Val Pro Gly Asp Thr Ile Leu Ile Asn Asn Arg Pro
                485                 490                 495

Gly Pro Arg Glu Pro Pro Pro Tyr Gln Glu Pro Arg Pro Arg Gly Asn
            500                 505                 510

Pro Pro His Ser Ala Pro Cys Val Pro Asn Gly Ser Ala Tyr Ser Gly
        515                 520                 525

Asp Tyr Met Glu Pro Glu Lys Pro Gly Ala Pro Leu Leu Pro Pro Pro
    530                 535                 540

Pro Gln Asn Ser Val Pro His Tyr Ala Glu Ala Asp Ile Val Thr Leu
545                 550                 555                 560

Gln Gly Val Thr Gly Gly Asn Thr Tyr Ala Val Pro Ala Leu Pro Pro
                565                 570                 575

Gly Ala Val Gly Asp Gly Pro Pro Arg Val Asp Phe Pro Arg Ser Arg
            580                 585                 590

Leu Arg Phe Lys Glu Lys Leu Gly Glu Gly Gln Phe Gly Glu Val His
        595                 600                 605

Leu Cys Glu Val Asp Ser Pro Gln Asp Leu Val Ser Leu Asp Phe Pro
    610                 615                 620

Leu Asn Val Arg Lys Gly His Pro Leu Leu Val Ala Val Lys Ile Leu
625                 630                 635                 640

Arg Pro Asp Ala Thr Lys Asn Ala Arg Asn Asp Phe Leu Lys Glu Val
                645                 650                 655

Lys Ile Met Ser Arg Leu Lys Asp Pro Asn Ile Ile Arg Leu Leu Gly
            660                 665                 670

Val Cys Val Gln Asp Asp Pro Leu Cys Met Ile Thr Asp Tyr Met Glu
        675                 680                 685

Asn Gly Asp Leu Asn Gln Phe Leu Ser Ala His Gln Leu Glu Asp Lys
    690                 695                 700

Ala Ala Glu Gly Ala Pro Gly Asp Gly Gln Ala Ala Gln Gly Pro Thr
705                 710                 715                 720

Ile Ser Tyr Pro Met Leu Leu His Val Ala Ala Gln Ile Ala Ser Gly
                725                 730                 735

Met Arg Tyr Leu Ala Thr Leu Asn Phe Val His Arg Asp Leu Ala Thr
            740                 745                 750

Arg Asn Cys Leu Val Gly Glu Asn Phe Thr Ile Lys Ile Ala Asp Phe
        755                 760                 765

Gly Met Ser Arg Asn Leu Tyr Ala Gly Asp Tyr Tyr Arg Val Gln Gly
    770                 775                 780

Arg Ala Val Leu Pro Ile Arg Trp Met Ala Trp Glu Cys Ile Leu Met
785                 790                 795                 800

Gly Lys Phe Thr Thr Ala Ser Asp Val Trp Ala Phe Gly Val Thr Leu
                805                 810                 815

Trp Glu Val Leu Met Leu Cys Arg Ala Gln Pro Phe Gly Gln Leu Thr
            820                 825                 830

Asp Glu Gln Val Ile Glu Asn Ala Gly Glu Phe Phe Arg Asp Gln Gly
        835                 840                 845

Arg Gln Val Tyr Leu Ser Arg Pro Pro Ala Cys Pro Gln Gly Leu Tyr
    850                 855                 860

Glu Leu Met Leu Arg Cys Trp Ser Arg Glu Ser Glu Gln Arg Pro Pro
865                 870                 875                 880

Phe Ser Gln Leu His Arg Phe Leu Ala Glu Asp Ala Leu Asn Thr Val
```

885 890 895

<210> SEQ ID NO 38
<211> LENGTH: 2691
<212> TYPE: DNA
<213> ORGANISM: Artificial Sequence
<220> FEATURE:
<223> OTHER INFORMATION: Synthetic human DDR1 W53A Mutant-FLAG construct

<400> SEQUENCE: 38

```
atgtctgcac ttctgatcct agctcttgtt ggagctgcag ttgctgacta caaagaccat     60
gacggtgatt ataaagatca tgacatcgat tacaaggatg acgatgacaa ggcgatcgcg    120
gacatgaagg gacattttga tcctgccaag tgccgctatg ccctgggcat gcaggaccgg    180
accatcccag acagtgacat ctctgcttcc agctccgcgt cagattccac tgccgcccgc    240
cacagcaggt tggagagcag tgacggggat ggggcctggt gccccgcagg gtcggtgttt    300
cccaaggagg aggagtactt gcaggtggat ctacaacgac tgcacctggt ggctctggtg    360
ggcacccagg gacggcatgc cgggggcctg ggcaaggagt tctcccggag ctaccggctg    420
cgttactccc gggatggtcg ccgctggatg ggctggaagg accgctgggg tcaggaggtg    480
atctcaggca atgaggaccc tgagggagtg gtgctgaagg accttgggcc ccccatggtt    540
gcccgactgg ttcgcttcta cccccgggct gaccgggtca tgagcgtctg tctgcgggta    600
gagctctatg gctgcctctg gagggatgga ctcctgtctt acactgcccc tgtggggcag    660
acaatgtatt tatctgaggc cgtgtacctc aacgactcca cctatgacgg acataccgtg    720
ggcggactgc agtatggggg tctgggccag ctggcagatg gtgtggtggg gctggatgac    780
tttaggaaga gtcaggagct gcgggtctgg ccaggctatg actatgtggg atggagcaac    840
cacagcttct ccagtggcta tgtggagatg gagtttgagt ttgaccggct gagggccttc    900
caggctatgc aggtccactg taacaacatg cacacgctgg gagcccgtct gcctggcggg    960
gtggaatgtc gcttccggcg tggccctgcc atggcctggg agggggagcc catgcgccac   1020
aacctagggg gcaacctggg ggaccccaga gcccgggctg tctcagtgcc ccttggcggc   1080
cgtgtggctc gctttctgca gtgccgcttc ctctttgcgg ggccctggtt actcttcagc   1140
gaaatctcct tcatctctga tgtggtgaac aattcctctc cggcactggg aggcaccttc   1200
ccgccagccc cctggtggcc gcctggccca cctcccacca acttcagcag cttggagctg   1260
gagcccagag gccagcagcc cgtggccaag gccgagggga gcccgaccgc catcctcatc   1320
ggctgcctgg tggccatcat cctgctcctg ctgctcatca ttgccctcat gctctggcgg   1380
ctgcactggc gcaggctcct cagcaaggct gaacggaggg tgttggaaga ggagctgacg   1440
gttcacctct ctgtccctgg ggacactatc ctcatcaaca accgcccagg tcctagagag   1500
ccacccccgt accaggagcc ccggcctcgt gggaatccgc cccactccgc tccctgtgtc   1560
cccaatggct ctgcctacag tggggactat atggagcctg agaagccagg cgccccgctt   1620
ctgcccccac ctccccagaa cagcgtcccc cattatgccg aggctgacat tgttaccctg   1680
cagggcgtca ccgggggcaa cacctatgct gtgcctgcac tgcccccagg ggcagtcggg   1740
gatgggcccc ccagagtgga tttccctcga tctcgactcc gcttcaagga gaagcttggc   1800
gagggccagt ttggggaggt gcacctgtgt gaggtcgaca gccctcaaga tctggttagt   1860
cttgatttcc cccttaatgt gcgtaaggga caccctttgc tggtagctgt caagatctta   1920
cggccagatg ccaccaagaa tgccaggaat gatttcctga aagaggtgaa gatcatgtcg   1980
aggctcaagg acccaaacat cattcggctg ctgggcgtgt gtgtgcagga cgacccctc    2040
```

```
tgcatgatta ctgactacat ggagaacggc gacctcaacc agttcctcag tgcccaccag   2100

ctggaggaca aggcagccga gggggcccct ggggacgggc aggctgcgca ggggcccacc   2160

atcagctacc caatgctgct gcatgtggca gcccagatcg cctccggcat gcgctatctg   2220

gccacactca actttgtaca tcgggacctg gccacgcgga actgcctagt tggggaaaat   2280

ttcaccatca aaatcgcaga ctttggcatg agccggaacc tctatgctgg ggactattac   2340

cgtgtgcagg gccgggcagt gctgcccatc cgctggatgg cctgggagtg catcctcatg   2400

gggaagttca cgactgcgag tgacgtgtgg gcctttggtg tgaccctgtg ggaggtgctg   2460

atgctctgta gggcccagcc ctttgggcag ctcaccgacg agcaggtcat cgagaacgcg   2520

ggggagttct tccgggacca gggccggcag gtgtacctgt cccggccgcc tgcctgcccg   2580

cagggcctat atgagctgat gcttcggtgc tggagccggg agtctgagca gcgaccaccc   2640

ttttcccagc tgcatcggtt cctggcagag gatgcactca acacggtgtg a            2691
```

```
<210> SEQ ID NO 39
<211> LENGTH: 896
<212> TYPE: PRT
<213> ORGANISM: Artificial Sequence
<220> FEATURE:
<223> OTHER INFORMATION: Synthetic human DDR1 W53A Mutant-FLAG construct

<400> SEQUENCE: 39

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ala Ile Ala Asp Met Lys Gly His Phe Asp Pro
        35                  40                  45

Ala Lys Cys Arg Tyr Ala Leu Gly Met Gln Asp Arg Thr Ile Pro Asp
    50                  55                  60

Ser Asp Ile Ser Ala Ser Ser Ser Ala Ser Asp Ser Thr Ala Ala Arg
65                  70                  75                  80

His Ser Arg Leu Glu Ser Ser Asp Gly Asp Gly Ala Trp Cys Pro Ala
                85                  90                  95

Gly Ser Val Phe Pro Lys Glu Glu Glu Tyr Leu Gln Val Asp Leu Gln
            100                 105                 110

Arg Leu His Leu Val Ala Leu Val Gly Thr Gln Gly Arg His Ala Gly
        115                 120                 125

Gly Leu Gly Lys Glu Phe Ser Arg Ser Tyr Arg Leu Arg Tyr Ser Arg
    130                 135                 140

Asp Gly Arg Arg Trp Met Gly Trp Lys Asp Arg Trp Gly Gln Glu Val
145                 150                 155                 160

Ile Ser Gly Asn Glu Asp Pro Glu Gly Val Val Leu Lys Asp Leu Gly
                165                 170                 175

Pro Pro Met Val Ala Arg Leu Val Arg Phe Tyr Pro Arg Ala Asp Arg
            180                 185                 190

Val Met Ser Val Cys Leu Arg Val Glu Leu Tyr Gly Cys Leu Trp Arg
        195                 200                 205

Asp Gly Leu Leu Ser Tyr Thr Ala Pro Val Gly Gln Thr Met Tyr Leu
    210                 215                 220

Ser Glu Ala Val Tyr Leu Asn Asp Ser Thr Tyr Asp Gly His Thr Val
225                 230                 235                 240

Gly Gly Leu Gln Tyr Gly Gly Leu Gly Gln Leu Ala Asp Gly Val Val
```

```
                245                 250                 255

Gly Leu Asp Asp Phe Arg Lys Ser Gln Glu Leu Arg Val Trp Pro Gly
            260                 265                 270

Tyr Asp Tyr Val Gly Trp Ser Asn His Ser Phe Ser Ser Gly Tyr Val
        275                 280                 285

Glu Met Glu Phe Glu Phe Asp Arg Leu Arg Ala Phe Gln Ala Met Gln
    290                 295                 300

Val His Cys Asn Asn Met His Thr Leu Gly Ala Arg Leu Pro Gly Gly
305                 310                 315                 320

Val Glu Cys Arg Phe Arg Arg Gly Pro Ala Met Ala Trp Glu Gly Glu
                325                 330                 335

Pro Met Arg His Asn Leu Gly Gly Asn Leu Gly Asp Pro Arg Ala Arg
            340                 345                 350

Ala Val Ser Val Pro Leu Gly Gly Arg Val Ala Arg Phe Leu Gln Cys
        355                 360                 365

Arg Phe Leu Phe Ala Gly Pro Trp Leu Leu Phe Ser Glu Ile Ser Phe
    370                 375                 380

Ile Ser Asp Val Val Asn Asn Ser Ser Pro Ala Leu Gly Gly Thr Phe
385                 390                 395                 400

Pro Pro Ala Pro Trp Trp Pro Pro Gly Pro Pro Pro Thr Asn Phe Ser
                405                 410                 415

Ser Leu Glu Leu Glu Pro Arg Gly Gln Gln Pro Val Ala Lys Ala Glu
            420                 425                 430

Gly Ser Pro Thr Ala Ile Leu Ile Gly Cys Leu Val Ala Ile Ile Leu
        435                 440                 445

Leu Leu Leu Leu Ile Ile Ala Leu Met Leu Trp Arg Leu His Trp Arg
    450                 455                 460

Arg Leu Leu Ser Lys Ala Glu Arg Arg Val Leu Glu Glu Glu Leu Thr
465                 470                 475                 480

Val His Leu Ser Val Pro Gly Asp Thr Ile Leu Ile Asn Asn Arg Pro
                485                 490                 495

Gly Pro Arg Glu Pro Pro Pro Tyr Gln Glu Pro Arg Pro Arg Gly Asn
            500                 505                 510

Pro Pro His Ser Ala Pro Cys Val Pro Asn Gly Ser Ala Tyr Ser Gly
        515                 520                 525

Asp Tyr Met Glu Pro Glu Lys Pro Gly Ala Pro Leu Leu Pro Pro Pro
    530                 535                 540

Pro Gln Asn Ser Val Pro His Tyr Ala Glu Ala Asp Ile Val Thr Leu
545                 550                 555                 560

Gln Gly Val Thr Gly Gly Asn Thr Tyr Ala Val Pro Ala Leu Pro Pro
                565                 570                 575

Gly Ala Val Gly Asp Gly Pro Pro Arg Val Asp Phe Pro Arg Ser Arg
            580                 585                 590

Leu Arg Phe Lys Glu Lys Leu Gly Glu Gly Gln Phe Gly Glu Val His
        595                 600                 605

Leu Cys Glu Val Asp Ser Pro Gln Asp Leu Val Ser Leu Asp Phe Pro
    610                 615                 620

Leu Asn Val Arg Lys Gly His Pro Leu Leu Val Ala Val Lys Ile Leu
625                 630                 635                 640

Arg Pro Asp Ala Thr Lys Asn Ala Arg Asn Asp Phe Leu Lys Glu Val
                645                 650                 655

Lys Ile Met Ser Arg Leu Lys Asp Pro Asn Ile Ile Arg Leu Leu Gly
            660                 665                 670
```

```
Val Cys Val Gln Asp Asp Pro Leu Cys Met Ile Thr Asp Tyr Met Glu
        675                 680                 685

Asn Gly Asp Leu Asn Gln Phe Leu Ser Ala His Gln Leu Glu Asp Lys
    690                 695                 700

Ala Ala Glu Gly Ala Pro Gly Asp Gly Gln Ala Ala Gln Gly Pro Thr
705                 710                 715                 720

Ile Ser Tyr Pro Met Leu Leu His Val Ala Ala Gln Ile Ala Ser Gly
                725                 730                 735

Met Arg Tyr Leu Ala Thr Leu Asn Phe Val His Arg Asp Leu Ala Thr
            740                 745                 750

Arg Asn Cys Leu Val Gly Glu Asn Phe Thr Ile Lys Ile Ala Asp Phe
        755                 760                 765

Gly Met Ser Arg Asn Leu Tyr Ala Gly Asp Tyr Tyr Arg Val Gln Gly
    770                 775                 780

Arg Ala Val Leu Pro Ile Arg Trp Met Ala Trp Glu Cys Ile Leu Met
785                 790                 795                 800

Gly Lys Phe Thr Thr Ala Ser Asp Val Trp Ala Phe Gly Val Thr Leu
                805                 810                 815

Trp Glu Val Leu Met Leu Cys Arg Ala Gln Pro Phe Gly Gln Leu Thr
            820                 825                 830

Asp Glu Gln Val Ile Glu Asn Ala Gly Glu Phe Phe Arg Asp Gln Gly
        835                 840                 845

Arg Gln Val Tyr Leu Ser Arg Pro Pro Ala Cys Pro Gln Gly Leu Tyr
    850                 855                 860

Glu Leu Met Leu Arg Cys Trp Ser Arg Glu Ser Glu Gln Arg Pro Pro
865                 870                 875                 880

Phe Ser Gln Leu His Arg Phe Leu Ala Glu Asp Ala Leu Asn Thr Val
                885                 890                 895


<210> SEQ ID NO 40
<211> LENGTH: 8
<212> TYPE: PRT
<213> ORGANISM: Artificial Sequence
<220> FEATURE:
<223> OTHER INFORMATION: Synthetic FLAG Tag sequence

<400> SEQUENCE: 40

Asp Tyr Lys Asp Asp Asp Asp Lys
1               5


<210> SEQ ID NO 41
<211> LENGTH: 155
<212> TYPE: PRT
<213> ORGANISM: Artificial Sequence
<220> FEATURE:
<223> OTHER INFORMATION: Synthetic DDR1 Discoidin Domain sequence

<400> SEQUENCE: 41

Cys Arg Tyr Ala Leu Gly Met Gln Asp Arg Thr Ile Pro Asp Ser Asp
1               5                   10                  15

Ile Ser Ala Ser Ser Ser Trp Ser Asp Ser Thr Ala Ala Arg His Ser
            20                  25                  30

Arg Leu Glu Ser Ser Asp Gly Asp Gly Ala Trp Cys Pro Ala Gly Ser
        35                  40                  45

Val Phe Pro Lys Glu Glu Glu Tyr Leu Gln Val Asp Leu Gln Arg Leu
    50                  55                  60

His Leu Val Ala Leu Val Gly Thr Gln Gly Arg His Ala Gly Gly Leu
```

-continued

```
65                  70                  75                  80

Gly Lys Glu Phe Ser Arg Ser Tyr Arg Leu Arg Tyr Ser Arg Asp Gly
                85                  90                  95

Arg Arg Trp Met Gly Trp Lys Asp Arg Trp Gly Gln Glu Val Ile Ser
            100                 105                 110

Gly Asn Glu Asp Pro Glu Gly Val Val Leu Lys Asp Leu Gly Pro Pro
        115                 120                 125

Met Val Ala Arg Leu Val Arg Phe Tyr Pro Arg Ala Asp Arg Val Met
    130                 135                 140

Ser Val Cys Leu Arg Val Glu Leu Tyr Gly Cys
145                 150                 155
```

DDR1-BINDING AGENTS AND METHODS OF USE THEREOF

CROSS REFERENCE TO RELATED APPLICATIONS

This application is a divisional application of U.S. National Phase of International Application No. PCT/US2009/053596, filed Aug. 12, 2009, now U.S. Pat. No. 8,652,843, which claims the benefit of U.S. Provisional Application No. 61/218,259, filed Jun. 18, 2009, and U.S. Provisional Application No. 61/088,286, filed Aug. 12, 2008.

BACKGROUND OF THE INVENTION

1. Field of the Invention

The present invention relates to the field of oncology and provides novel compositions and methods for treating and diagnosing cancer. In particular, the present invention provides antibodies against DDR1 for the treatment and diagnosis of solid tumors.

2. Background Art

Cancer is one of the leading causes of death in the developed world, with over one million people diagnosed with cancer and 500,000 deaths per year in the United States alone. Overall it is estimated that more than 1 in 3 people will develop some form of cancer during their lifetime. There are more than 200 different types of cancer, four of which—breast, lung, colorectal, and prostate—account for over half of all new cases (Jemal et al., 2003, *Cancer J. Clin.* 53:5-26).

Cancer of the breast, lung, colorectal, and prostate, as well as many other cancers, present as solid tumors that are composed of heterogeneous cell populations. For example, breast cancers are a mixture of cancer cells and normal cells, including mesenchymal (stromal) cells, inflammatory cells, and endothelial cells. Several models of cancer provide different explanations for the presence of this heterogeneity. One model, the classic model of cancer, holds that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells have some degree of tumorigenic potential. (Pandis et al., 1998, *Genes, Chromosomes & Cancer* 12:122-129; Kuukasjrvi et al., 1997, *Cancer Res.* 57:1597-1604; Bonsing et al., 1993, *Cancer* 71:382-391; Bonsing et al., 2000, *Genes Chromosomes & Cancer* 82: 173-183; Beerman H et al., 1991, *Cytometry* 12:147-54; Aubele M & Werner M, 1999, *Analyt. Cell. Path.* 19:53; Shen L et al., 2000, *Cancer Res.* 60:3884).

An alternative model for the observed solid tumor cell heterogeneity derives from the impact of stem cells on tumor development. According to this model cancer arises from dysregulation of the mechanisms that control normal tissue development and maintenance. (Beachy et al., 2004, Nature 432:324). During normal animal development, cells of most or all tissues are derived from normal precursors, called stem cells (Morrison et al., 1997, *Cell* 88:287-98; Morrison et al., 1997, *Curr. Opin. Imnmunol.* 9:216-21; Morrison et al., 1995, *Annu. Rev. Cell. Dev. Biol.* 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-studied example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain. Tumors derived from a "solid tumor stem cell" (or "cancer stem cell" from a solid tumor) subsequently undergo chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, *Nature* 17:645-8). More recently it has been demonstrated that malignant human breast tumors similarly harbor a small, distinct population of cancer stem cells enriched for the ability to form tumors in immunodeficient mice. An ESA+, CD44+, CD24−/low, Lin-cell population was found to be 50-fold enriched for tumorigenic cells compared to unfractionated tumor cells (Al-Hajj et al., 2003, *Proc. Nat'l. Acad. Sci.* 100:3983-8). The ability to prospectively isolate the tumorigenic cancer cells has permitted investigation of critical biological pathways that underlie tumorigenicity in these cells, and thus promises the development of better diagnostic assays and therapeutics for cancer patients.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

BRIEF SUMMARY OF THE INVENTION

The invention provides agents which bind to and/or modulate the activity of the discoidin domain receptor 1 (DDR1) and compositions, such as pharmaceutical compositions, comprising those agents. In certain embodiments, the agents are antibodies. In certain embodiments, the agents are antibodies that specifically bind to DDR1 (e.g., human DDR1). In certain embodiments, the agents that specifically bind to and/or modulate the activity of DDR1 further specifically bind to and/or modulate the activity of the discoidin domain receptor 2 (DDR2). The invention further provides methods of targeting cancer stem cells with the agents. In certain embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor. The invention also provides methods of using the agents in the treatment of cancer and/or in the inhibition of the growth of tumors comprising cancer stem cells.

In one aspect, the invention provides a method of inhibiting the growth of a tumor in a subject, comprising administering to the subject a therapeutically effective amount of an agent that modulates the activity of DDR1. In certain embodiments the tumor comprises cancer stem cells. In certain embodiments, the agent reduces tumorigenicity of the tumor by reducing the number and/or frequency of cancer stem cells in the tumor. In certain embodiments, the agent is an antibody, such as an antibody that specifically binds to DDR1. In certain embodiments, the agent reduces the frequency of cancer stem cells in the tumor.

In another aspect, the invention provides a method of reducing the tumorigenicity of a tumor comprising cancer stem cells by reducing the number and/or frequency of cancer stem cells in the tumor, wherein the method comprises contacting the tumor with an effective amount of an agent that modulates the activity of DDR1. In certain embodiments, the agent is an antibody, such as an antibody that specifically binds to DDR1.

In another aspect, the invention provides an antibody that modulates the activity of DDR1. In certain embodiments, the antibody reduces the frequency of cancer stem cells in a tumor, reduces the number of cancer stem cells in a tumor, reduces the tumorigenicity of a tumor, and/or reduces the tumorigenicity of a tumor by reducing the number and/or frequency of cancer stem cells in the tumor. In certain embodiments, the antibody specifically binds to DDR1. Pharmaceutical compositions comprising both the antibody and a pharmaceutically acceptable vehicle are further provided, as are cell lines that produce the antibody. Methods of treating cancer and/or inhibiting tumor growth in a subject (e.g., a human) comprising administering to the subject an effective amount of a composition comprising the antibody are also provided. Methods of inhibiting inflammation and/or fibrosis in a subject comprising administering to the subject an effective amount of a composition comprising the antibody are further provided.

In certain embodiments of each of the aforementioned aspects, as well as other aspects described elsewhere herein, the agent or antibody specifically binds to the extracellular domain of DDR1. In certain embodiments, the agent or antibody binds the discoidin domain of DDR1. In certain embodiments, the agent or antibody binds to at least one amino acid in the sequence SASSSWSDSTAAR (SEQ ID NO:30) within human DDR1. In some embodiments, the agent or antibody further binds to additional amino acid residues within DDR1. In certain embodiments, the agent or antibody competes with an antibody that binds to at least one amino acid in the sequence SASSSWSDSTAAR (SEQ ID NO:30) within human DDR1.

In another aspect, the invention provides an antibody that specifically binds to an extracellular domain of human DDR1. In certain embodiments, the antibody comprises a heavy chain variable region having at least 90% sequence identity to SEQ ID NO:33, and/or a light chain variable region having at least 90% sequence identity to SEQ ID NO:35. In some embodiments, the antibody comprises a heavy chain variable region having at least 95% sequence identity to SEQ ID NO:33, and/or a light chain variable region having at least 95% sequence identity to SEQ ID NO:35. In some embodiments, the antibody comprises a heavy chain variable region comprising the sequence of SEQ ID NO:33, and/or a light chain variable region comprising the sequence of SEQ ID NO:35. In certain embodiments, the antibody comprises a heavy chain CDR1 comprising GYTFTDYFMK (SEQ ID NO:22), a heavy chain CDR2 comprising DINPNNGDTFYIQKFKG (SEQ ID NO:23), and/or a heavy chain CDR3 comprising SRDLAY (SEQ ID NO:24), and/or the antibody comprises a light chain CDR1 comprising KSSQSLLYSNGKTYLN (SEQ ID NO:27), a light chain CDR2 comprising QVSKLDS (SEQ ID NO:28), and/or a light chain CDR3 comprising VQGTDFPQT (SEQ ID NO:29). In certain embodiments, the antibody comprises a heavy chain variable region comprising (a) a heavy chain CDR1 comprising GYTFTDYFMK (SEQ ID NO:22), or a variant thereof comprising 1, 2, 3 or 4 amino acid substitutions; (b) a heavy chain CDR2 comprising DINPNNGDTFYIQKFKG (SEQ ID NO:23), or a variant thereof comprising 1, 2, 3 or 4 amino acid substitutions; and/or (c) a heavy chain CDR3 comprising SRDLAY (SEQ ID NO:24), or a variant thereof comprising 1, 2, 3 or 4 amino acid substitutions. In other embodiments, the antibody further comprises a light chain variable region comprising (a) a light chain CDR1 comprising KSSQSLLYSNGKTYLN (SEQ ID NO:27), or a variant thereof comprising 1, 2, 3 or 4 amino acid substitutions; (b) a light chain CDR2 comprising QVSKLDS (SEQ ID NO:28), or a variant thereof comprising 1, 2, 3 or 4 amino acid substitutions; and/or (c) a light chain CDR3 comprising VQGTDFPQT (SEQ ID NO:29), or a variant thereof comprising 1, 2, 3 or 4 amino acid substitutions. In some embodiments, the amino acid substitutions are conservative amino acid substitutions.

In another aspect, the invention provides an antibody, 20M102, produced by the hybridoma cell line deposited as ATCC deposit number PTA-10051. In some embodiments, the antibody is a humanized version of 20M102. In some embodiments, the invention provides an antibody which specifically binds to the same DDR1 epitope as the epitope to which antibody 20M102 binds. In other embodiments, the invention provides an antibody which competes with any of the antibodies as described in the aforementioned embodiments and/or aspects, as well as other aspects/embodiments described elsewhere herein, for specific binding to DDR1.

In certain embodiments of each of the aforementioned aspects, as well as other aspects described elsewhere herein, the agent or antibody that specifically binds to and/or modulates the activity of DDR1 further specifically binds to and/or modulates the activity of DDR2. In certain embodiments, the antibody binds the discoidin domain of DDR2.

In certain embodiments of each of the aforementioned aspects, as well as other aspects described elsewhere herein, the agent or antibody is an antagonist of DDR1. In some embodiments, the agent or antibody is also an antagonist of DDR2.

In certain embodiments of each of the aforementioned aspects, as well as other aspects described elsewhere herein, the agent or antibody inhibits the binding of a ligand to DDR1. In some embodiments, the agent or antibody inhibits the binding of collagen to DDR1. In some embodiments, the agent or antibody inhibits or blocks the activation of DDR1. In some embodiments, the agent or antibody inhibits or blocks phosphorylation of DDR1. In some embodiments, the agent or antibody inhibits or blocks collagen-induced phosphorylation of DDR1. In some embodiments, the agent or antibody also inhibits the binding of collagen to DDR2.

In certain embodiments of each of the aforementioned aspects or embodiments, as well as other aspects and/or embodiments described elsewhere herein, the antibody is a recombinant antibody. In certain embodiments, the antibody is a monoclonal antibody, a chimeric antibody, a humanized antibody, or a human antibody. In some embodiments, the antibody is an antibody fragment. In certain embodiments, the antibody or antibody fragment is monovalent, monospecific, bivalent, bispecific, or multispecific. In certain embodiments, the antibody is conjugated to a cytotoxic moiety. In certain embodiments, the antibody is isolated. In still further embodiments, the antibody is substantially pure.

In another aspect, the invention provides a polypeptide. In some embodiments, the polypeptide is an antibody and/or a fragment of an antibody. In some embodiments, the polypeptide is isolated. In certain embodiments, the polypeptide is substantially pure. In some embodiments, the polypeptide comprises the amino acid sequence of SEQ ID NO:33, and/or the amino acid sequence of SEQ ID NO:35. In some embodiments, the polypeptide comprises at least a portion of the amino acid sequence of SEQ ID NO:33, and/or at least a portion of the amino acid sequence of SEQ ID NO: 35. Pharmaceutical compositions comprising both the polypeptide and a pharmaceutically acceptable vehicle are further provided, as are cell lines that produce the polypeptide.

In another aspect, the invention provides a polynucleotide molecule encoding any of the antibodies and/or polypeptides of the aforementioned aspects, as well as other aspects as described herein. In some embodiments, an expression vector comprises the polynucleotide molecule. In other embodiments, a host cell comprises the expression vector. In some embodiments, the host cell is a hybridoma cell line. In certain embodiments of each of the aforementioned aspects, as well as other aspects described elsewhere herein, DDR1 is human DDR1. Likewise, in some embodiments, DDR2 is human DDR2.

In certain embodiments of each of the aforementioned aspects, as well as other aspects described elsewhere herein, the treatment methods further comprise administering at least one additional therapeutic agent appropriate for effecting combination therapy (e.g., a chemotherapeutic agent or other anticancer agent, if cancer is to be treated).

In certain embodiments of each of the aforementioned aspects, as well as other aspects described elsewhere herein, the tumors which are targeted comprise cells which are Hes1-expressing cells and/or which are LGR5-expressing cells. In some embodiments, the Hes1-expressing cells and/or LGR5-expressing cells are cancer stem cells.

In certain embodiments of each of the aforementioned aspects, as well as other aspects described elsewhere herein, the tumors which are targeted are breast, colorectal, hepatic, renal, lung, pancreatic, ovarian, prostate, or head and neck tumors.

The present invention further provides methods of treating cancer in a subject. In some embodiments, the method comprises administering to a subject a therapeutically effective amount of any of the antibodies or polypeptides described in the aforementioned aspects, as well as other aspects and embodiments described elsewhere herein. In some embodiments, the cancer to be treated is breast cancer, colorectal cancer, hepatic cancer, kidney cancer, liver cancer, lung cancer, pancreatic cancer, gastrointestinal cancer, melanoma, ovarian cancer, prostate cancer, cervical cancer, bladder cancer, glioblastoma, and head and neck cancer. In some embodiments, the methods further comprise administering to the subject at least one additional anti-cancer agent.

The present invention further provides methods of identifying and/or isolating cancer stem cells (e.g., based on expression of DDR1), screening for anti-cancer agents, and screening patients for suitability for treatment with the agents described herein.

The present invention further provides methods of identifying an antibody that inhibits activity of DDR1, wherein the method comprises assaying antibodies for specific binding to DDR1 and for specific binding to a variant of DDR1. A reduction in binding by an antibody to the variant DDR1 as compared to native/wildtype DDR1 identifies an antibody that inhibits activity of DDR1. In some embodiments, the variant of DDR1 comprises a sequence in which the sequence SASSSWSDSTAAR (SEQ ID NO:30) has been replaced by sequence SASSSASDSTAAR (SEQ ID NO:31).

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTION OF THE DRAWINGS/FIGURES

FIG. 1. Detection of DDR1 protein expression by tumors.

Figure 2:
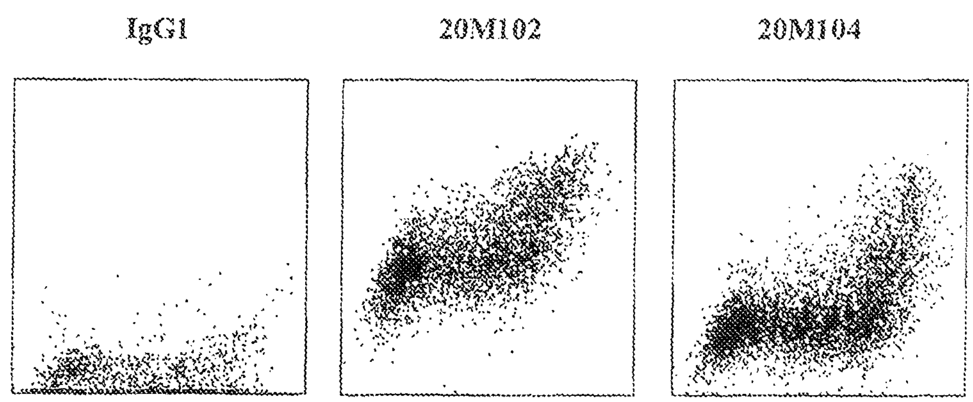

FIG. 2. FACS analysis of monoclonal antibodies for binding to DDR1 on the surface of HEK293 cells.

Figure 3A:
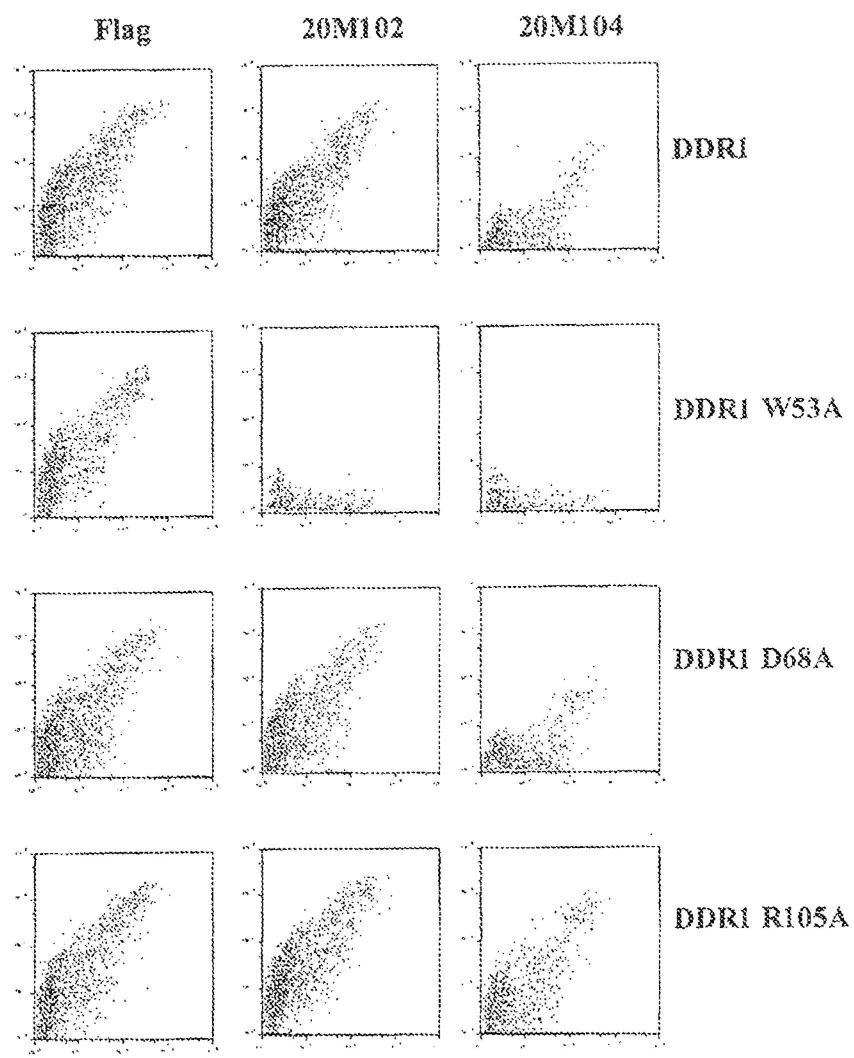
Figure 3B:
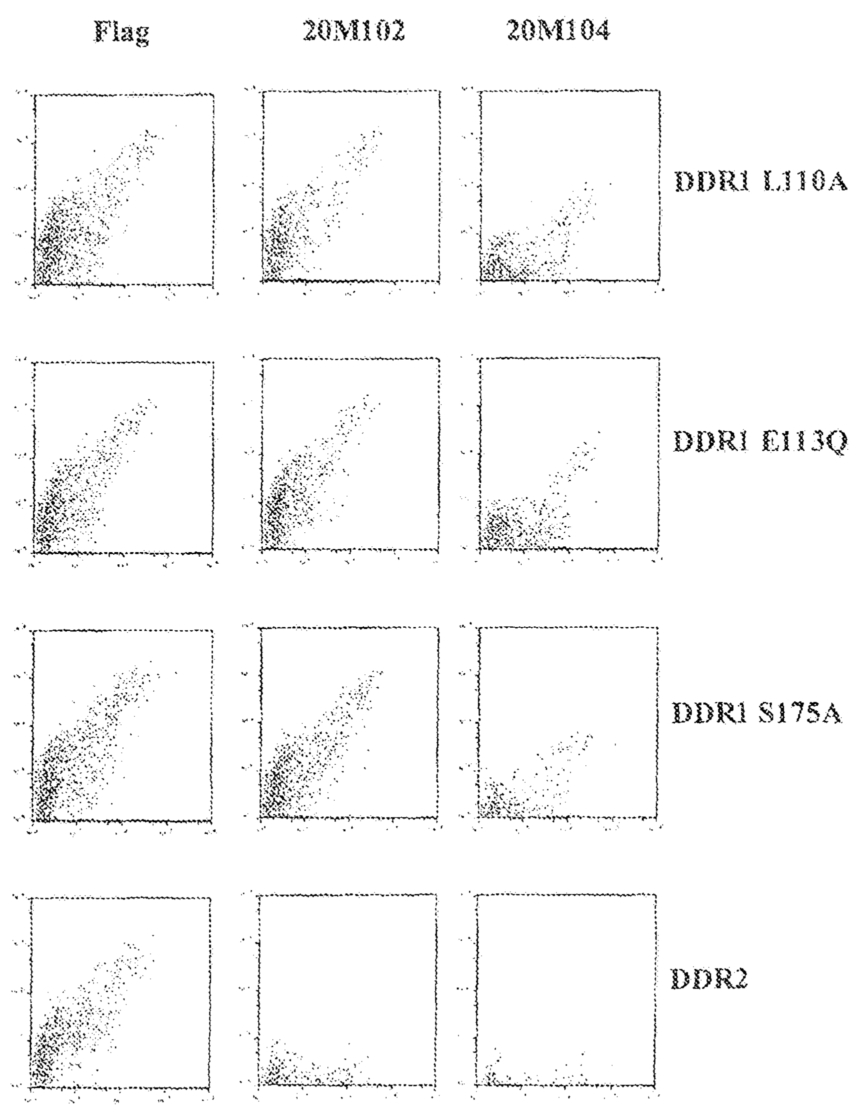

FIGS. 3A and 3B. FACS analysis of antibody binding to DDR1 variants. FIG. 3A shows antibody binding to DDR1 wildtype, DDR1 W53A, DDR1 D68A and DDR1 R105A variants. FIG. 3B shows antibody binding to DDR1 L110A, DDR1 E113Q and DDR1 S175A variants and DDR2.

Figure 4:
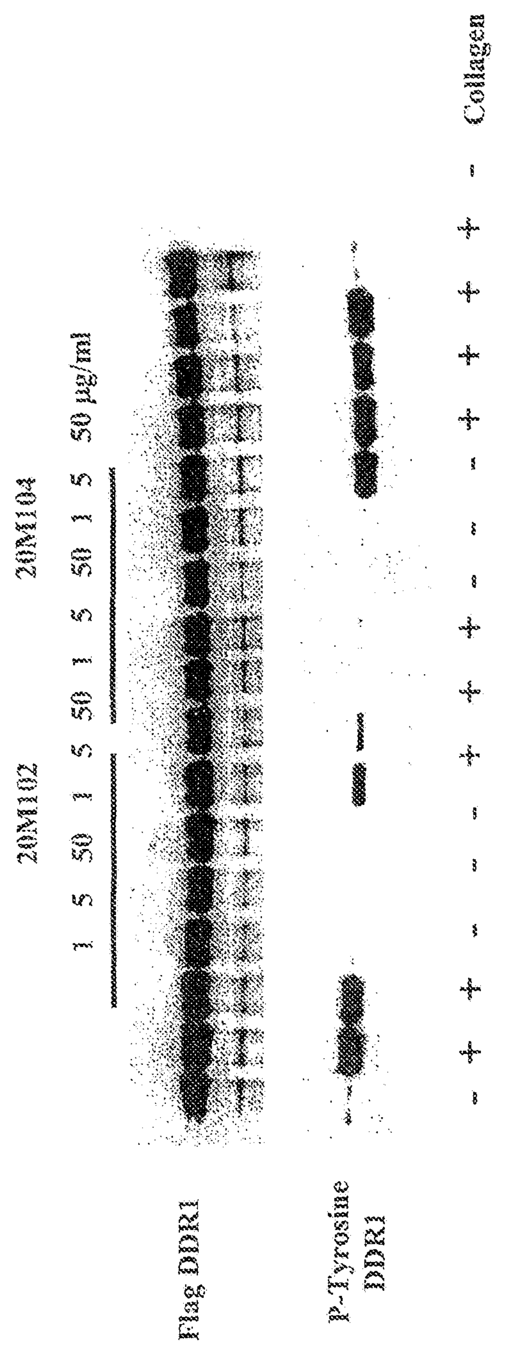

FIG. 4. Tyrosine phosphorylation assay with antibodies 20M102 and 20M104.

Figure 5:
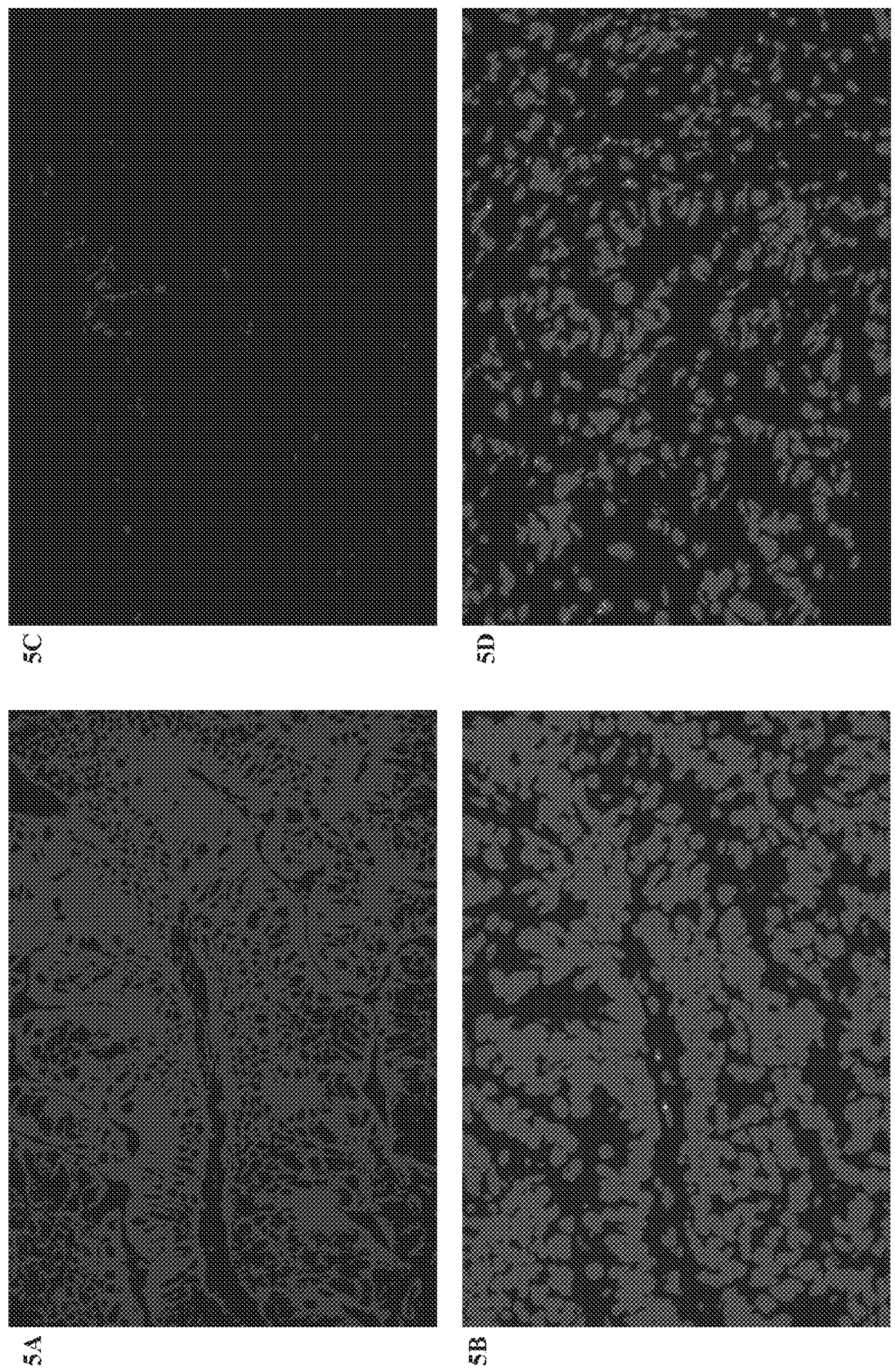

FIG. 5. Detection of DDR1 protein expression in OMP-C37 tumor cells. Cryosections of OMP-C37 colon tumor were stained with 20M102 (panels A and C) or control antibody (panels B and D). Immunofluorescence shows the localization of DDR1 protein in panel A, and panel C represents an image of nuclear DAPI staining for the cryosection. Shown in panel B is immunofluorescence associated with a control antibody, and panel D is the nuclear DAPI stain.

Figure 6:
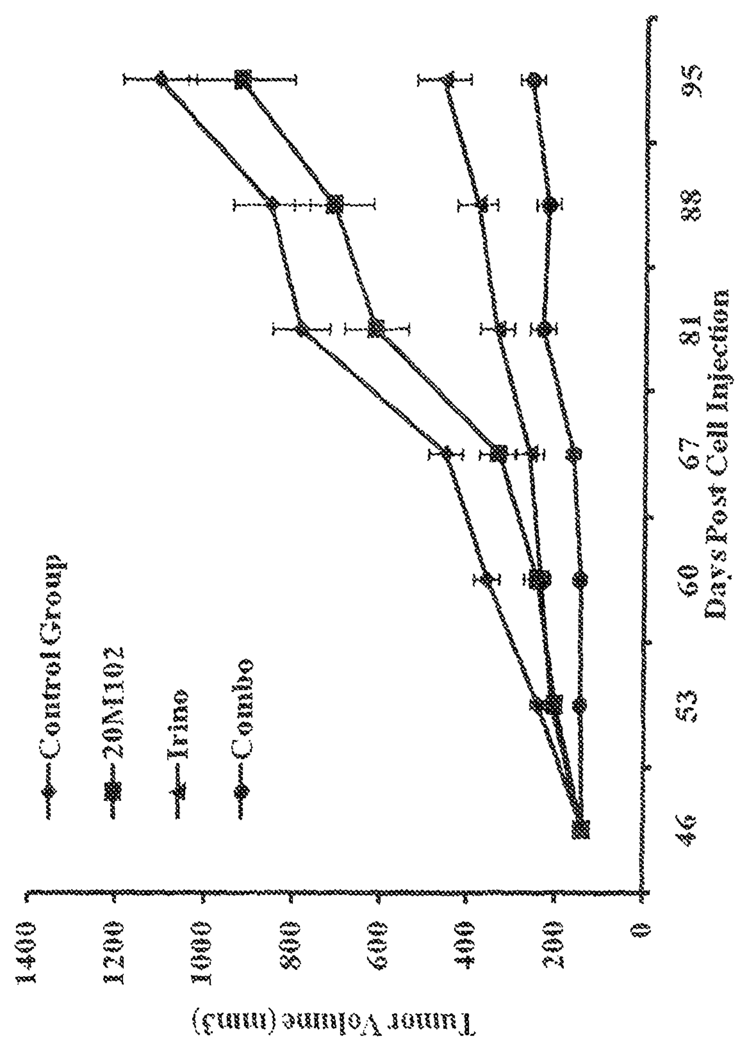

FIG. 6. Tumor xenograft efficacy study. SCID mice were injected with dissociated OMP-C37 cells and treated with anti-DDR1 antibody or control antibody in the presence or absence of irinotecan. Mice with established tumors were treated with control antibody, 20M102, irinotecan or combination of 20M102 and irinotecan. The combined treatment with 20M102 and irinotecan (circles) reduced tumor volume (y-axis $mm^3$) as compared to animals treated with either control antibody (diamonds) or 20M102 (squares) or irinotecan alone (triangles).

DETAILED DESCRIPTION OF THE INVENTION

The term "discoidin domain receptor 1" or "DDR1" as used herein refers to all isoforms and variants of the DDR1 protein, including DDR1a, DDR1b, DDR1c, DDR1d and DDR1e.

The term "antibody" is used to mean an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. In certain embodiments, antibodies of the present invention include antagonist antibodies that specifically bind to a cancer stem cell marker protein and interfere with, for example, ligand binding, receptor dimerization, expression of a cancer stem cell marker protein, and/or downstream signaling of a cancer stem cell marker protein. In certain embodiments, disclosed antibodies include agonist antibodies that specifically bind to a cancer stem cell marker protein and promote, for example, ligand binding, receptor dimerization, and/or signaling by a cancer stem cell marker protein. In certain embodiments, disclosed antibodies do not interfere with or promote the biological activity of a cancer stem cell marker protein but inhibit tumor growth by, for example, antibody internalization and/or recognition by the immune system. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to a homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including, but not limited to, by hybridoma, phage selection, recombinant expression, and transgenic animals.

As used herein, the term "humanized antibody" refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and/or capability. In some instances, the Fv framework region (FR) residues of a human immunoglobulin are replaced with the corresponding residues in an antibody from a non-human species that has the desired specificity, affinity, and/or capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all, or substantially all, of the CDR regions that correspond to the non-human immunoglobulin; whereas all, or substantially all, of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides. The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc.) with the desired specificity, affinity, and capability, while the constant regions are homologous to the sequences in antibodies derived from another species (usually human) to avoid eliciting an immune response in that species. The term chimeric antibody includes monovalent, divalent and polyvalent antibodies. The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (often referred to as "linear epitopes") are typically retained upon protein denaturing, whereas epitopes formed by tertiary folding (often referred to as "conformational epitopes") are typically lost upon protein denaturing. An epitope typically includes at least 3, and more usually, at least 5 or 8-10 amino acids in a unique spatial conformation.

That an antibody "selectively binds" or "specifically binds" means that the antibody reacts or associates more frequently, more rapidly, with greater duration, with greater affinity, or with some combination of the above to an epitope than with alternative substances, including unrelated proteins. "Selectively binds" or "specifically binds" means at times that an antibody binds to a protein with a $K_D$ of about 0.1 mM or less, at times about 1 μM or less, at times about 0.1 μM or less, at times about 0.01 μM or less, and at times about 1 nM or less. Because of the sequence identity between homologous proteins in different species, specific binding can include an antibody that recognizes a cancer stem cell marker protein in more than one species. It is understood that an antibody or binding moiety that specifically binds to a first target may or may not specifically bind to a second target. As such, "specific binding" does not necessarily require (although it can include) exclusive binding, i.e. binding to a single target. Generally, but not necessarily, reference to binding means specific binding.

The terms “isolated” or “purified” refer to material that is substantially or essentially free from components that normally accompany it in its native state. Purity and homogeneity are typically determined using analytical chemistry techniques such as polyacrylamide gel electrophoresis or high performance liquid chromatography. A protein (e.g., an antibody) or nucleic acid of the present disclosure that is the predominant species present in a preparation is substantially purified. In particular, in some embodiments, an isolated nucleic acid is separated from open reading frames that naturally flank the gene and encode proteins other than the protein encoded by the gene. In some embodiments, an isolated antibody is separated from other non-immunoglobulin proteins and from other immunoglobulin proteins with different antigen binding specificities. It can also mean that the nucleic acid or protein is in some embodiments at least 80% pure, in some embodiments at least 85% pure, in some embodiments at least 90% pure, in some embodiments at least 95% pure, and in some embodiments at least 99% pure.

As used herein, the terms “cancer” and “cancerous” refer to or describe the physiological condition in mammals in which a population of cells are characterized by unregulated cell growth.

Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancers.

“Tumor” and “neoplasm” as used herein refer to any mass of tissue that results from excessive cell growth or proliferation, either benign (noncancerous) or malignant (cancerous), including pre-cancerous lesions.

“Metastasis” as used herein refers to the process by which a cancer spreads or transfers from the site of origin to other regions of the body with the development of a similar cancerous lesion at the new location. A “metastatic” or “metastasizing” cell is one that loses adhesive contacts with neighboring cells and migrates via the bloodstream or lymph from the primary site of disease to invade neighboring body structures.

The terms “cancer stem cell”, “tumor stem cell”, or “solid tumor stem cell” are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of “cancer stem cells”, “tumor stem cells” or “solid tumor stem cells” confer on those cancer stem cells the ability to form palpable tumors upon serial transplantation into an immunocompromised mouse compared to the majority of tumor cells that fail to form tumors. Cancer stein cells undergo self-renewal versus differentiation in a chaotic manner to form tumors with abnormal cell types that can change over time as mutations occur. Solid tumor stem cells differ from the “cancer stem line” provided by U.S. Pat. No. 6,004,528. In that patent, the “cancer stem line” is defined as a slow growing progenitor cell type that itself has few mutations but which undergoes symmetric rather than asymmetric cell divisions as a result of tumorigenic changes that occur in the cell’s environment. This “cancer stem line” hypothesis thus proposes that highly mutated, rapidly proliferating tumor cells arise largely as a result of an abnormal environment, which causes relatively normal stem cells to accumulate and then undergo mutations that cause them to become tumor cells. U.S. Pat. No. 6,004,528 proposes that such a model can be used to enhance the diagnosis of cancer. The solid tumor stem cell model is fundamentally different from the “cancer stem line” model and as a result exhibits utilities not offered by the “cancer stem line” model. First, solid tumor stem cells are not “mutationally spared”. The “mutationally spared cancer stem line” described by U.S. Pat. No. 6,004,528 can be considered a pre-cancerous lesion, while solid tumor stem cells are cancer cells that may themselves contain the mutations that are responsible for tumorigenesis starting at the pre-cancerous stage through later stage cancer. That is, solid tumor stem cells (“cancer stem cells”) would be included among the highly mutated cells that are distinguished from the “cancer stem line” in U.S. Pat. No. 6,004,528. Second, the genetic mutations that lead to cancer can be largely intrinsic within the solid tumor stem cells as well as being environmental. The solid tumor stem cell model predicts that isolated solid tumor stem cells can give rise to additional tumors upon transplantation (thus explaining metastasis) while the “cancer stem line” model would predict that transplanted “cancer stem line” cells would not be able to give rise to a new tumor, since it was their abnormal environment that was tumorigenic. Indeed, the ability to transplant dissociated, and phenotypically isolated human solid tumor stem cells to mice (into an environment that is very different from the normal tumor environment) where they still form new tumors is distinguished from the “cancer stem line” model. Third, solid tumor stem cells likely divide both symmetrically and asymmetrically, such that symmetric cell division is not an obligate property. Fourth, solid tumor stem cells can divide rapidly or slowly, depending on many variables, such that a slow proliferation rate is not a defining characteristic.

The terms “cancer cell,” “tumor cell,” and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term “tumor cell” will be modified by the term “non-tumorigenic” when referring solely to those tumor cells lacking the capacity to renew and differentiate to distinguish those tumor cells from cancer stem cells.

As used herein “tumorigenic” refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor. These properties of self-renewal and proliferation to generate all other tumor cells confer on cancer stem cells the ability to form palpable tumors upon serial transplantation into an immunocompromised mouse compared to non-tumorigenic tumor cells, which are unable to form tumors upon serial transplantation. It has been observed that non-tumorigenic tumor cells may form a tumor upon primary transplantation into an immunocompromised mouse after obtaining the tumor cells from a solid tumor, but those non-tumorigenic tumor cells do not give rise to a tumor upon serial transplantation.

As used herein, the terms "stem cell cancer marker(s)", "cancer stem cell marker(s)", "tumor stem cell marker(s)", or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the terms "biopsy" and "biopsy tissue" refer to a sample of tissue or fluid that is removed from a subject for the purpose of determining if the sample contains cancerous tissue. In some embodiments, biopsy tissue or fluid is obtained because a subject is suspected of having cancer, and the biopsy tissue or fluid is then examined for the presence or absence of cancer.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable salt" refers to a salt of a compound that is pharmaceutically acceptable and that possesses the desired pharmacological activity of the parent compound.

"Pharmaceutically acceptable excipient, carrier or adjuvant" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the antibody.

"Pharmaceutically acceptable vehicle" refers to a diluent, adjuvant, excipient, or carrier with which at least one antibody of the present disclosure is administered.

The term "effective amount," "therapeutically effective amount" or "therapeutic effect" refers to an amount of an antibody, polypeptide, polynucleotide, small organic molecule, or other drug effective to "treat" a disease or disorder in a subject or mammal. In the case of cancer, the therapeutically effective amount of the drug has a therapeutic effect and as such can reduce the number of cancer cells; decrease tumorigenicity, tumorigenic frequency or tumorigenic capacity; reduce the number or frequency of cancer stem cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. Methods to determine tumorigenicity or tumorigenic frequency or capacity are demonstrated in copending application U.S. Ser. No. 11/776,935, incorporated by reference herein in its entirety. To the extent the drug prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus those in need of treatment include those already with the disorder, those prone to have the disorder; and those in whom the disorder is to be prevented. In certain embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity; reduction in the number or frequency of cancer stem cells; or some combination of effects.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA. The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length polypeptide or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. The term "gene" encompasses both cDNA and genomic forms of a gene.

The terms "polypeptide", "peptide", "protein", and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. "Amino acid analogs" refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant", including where the alteration results in the substitution of an amino acid with a chemically similar amino acid. Conservative substitution tables providing functionally similar amino acids are well known in the art (See, for example, Table 1). Guidance concerning which amino acid changes are likely to be phenotypically silent can also be found in Bowie et al., 1990, *Science* 247:1306 1310. Such conservatively modified variants are in addition to and do not exclude polymorphic variants, interspecies homologs, and alleles. Typical conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). As indicated, changes are typically of a minor nature, such as conservative amino acid substitutions that do not significantly affect the folding or activity of the protein.

TABLE 1

Conservative Amino Acid Substitutions

| Original Amino Acid | Exemplary Conservative Substitutions |
| --- | --- |
| Alanine | Valine, Isoleucine, Leucine, Glycine, Serine |
| Arginine | Lysine, Histidine, Glutamine, Asparagine |
| Asparagine | Glutamine, Histidine, Lysine, Arginine |
| Aspartic Acid | Glutamic Acid, Asparagine |
| Cysteine | Serine, Alanine |
| Glutamine | Asparagine |
| Glutamic Acid | Aspartic Acid, Glutamine |
| Clycine | Proline, Alanine |
| Histidine | Asparagine, Glutamine, Lysine, Arginine |
| Isoleucine | Leucine, Valine, Methionine, Alanine, Phenylalanine, Norleucine |
| Leucine | Norleucine, Isoleucine, Valine, Methionine, Alanine, Phenylalanine |
| Lysine | Arginine, Glutamine, Asparagine, Histidine |
| Methionine | Leucine, Phenylalanine, Isoleucine |
| Phenylalanine | Leucine, Valine, Isoleucine, Alanine, Tyrosine |
| Proline | Alanine, Glycine |
| Serine | Threonine |
| Threonine | Serine |
| Trytophan | Tyrosine, Phenylalanine |
| Tyrosine | Tryptophan, Phenylalanine, Threonine, Serine |
| Valine | Isoleucine, Methionine, Leucine, Phenylalanine, Alanine, Norleucine |

Like the tissues in which they originate, solid tumors consist of a heterogeneous population of cells. That the majority of these cells lack tumorigenicity suggested that the development and maintenance of solid tumors also relies on a small population of stem cells (i.e., tumorigenic cancer cells) with the capacity to proliferate and efficiently give rise both to additional tumor stem cells (self-renewal) and to the majority of more differentiated tumor cells that lack tumorigenic potential (i.e., non-tumorigenic cancer cells). The concept of cancer stem cells was first introduced soon after the discovery of hematopoietic stem cells (HSC) and was established experimentally in acute myelogenous leukemia (AML) (Park et al., 1971, *J. Natl. Cancer Inst.* 46:411-22; Lapidot et al., 1994, *Nature* 367:645-8; Bonnet & Dick, 1997, *Nat. Med.* 3:730-7; Hope et al., 2004, *Nat. Immunol.* 5:738-43). Stem cells from solid tumors have more recently been isolated based on their expression of a unique pattern of cell-surface receptors and on the assessment of their properties of self-renewal and proliferation in culture and in xenograft animal models. An ESA+ CD44+ CD24−/low Lineage-population greater than 50-fold enriched for the ability to form tumors relative to unfractionated tumor cells was discovered (Al-Hajj et al., 2003, *Proc. Nat'l. Acad. Sci.* 100:3983-8). The ability to isolate tumorigenic cancer stem cells from the bulk of non-tumorigenic tumor cells has led to the identification of cancer stem cell markers, genes with differential expression in cancer stem cells compared to non-tumorigenic tumor cells or normal epithelium, using microarray analysis. The present invention employs the knowledge of cancer stem cell markers to treat and diagnose cancer.

The cancer stem cell markers of the present invention relate to human discoidin domain receptor 1 (DDR1) and human discoidin domain receptor 2 (DDR2). The invention is based in part on the discovery of a correlation between the expression of DDR1 and Hes1 in a variety of tissue samples, as well as of a correlation between the expression of DDR1 and LGR5 (see Examples 10 and 11, below) in a variety of tissue samples. Expression of Hes1 is an indicator of Notch pathway activation, activity that may play an important role in tumorigenesis in certain tumors. LGR5 has previously been identified as both a stem cell marker (Barker et al., 2007, *Nature* 449:1003-7) and as a cancer stem cell marker (U.S. patent application Ser. No. 12/167,176, incorporated by reference herein in its entirety). The identification of DDR1 as a marker of cancer stem cells suggests that targeting this receptor may prove therapeutically effective in treating human cancers.

Furthermore, DDR2 has previously been identified as a cancer stem cell marker (U.S. Patent Publication No. 2008/0171045, incorporated by reference herein in its entirety).

Thus, the present identification of DDR1 as a cancer stem cell marker suggests the desirability of therapeutics, including, but not limited to, antibodies, that target both DDR1 and DDR2.

The discoidin domain receptors DDR1 and DDR2 form a subfamily of receptor tyrosine kinases based on the presence of an extracellular discoidin domain, a domain first identified in the slime mold *Dictyostelium discoideum* that functions in cell aggregation. Collagen serves as the physiological ligand for DDR2, and this interaction both inhibits fibrillogenesis of collagen and regulates expression of matrix-metalloproteases (MMP), enzymes that cleave native fibrillar collagen (Vogel, 1999, *FASEB* 13:S77-S82; Xu et al., 2005, *J. Biol. Chem.* 280:548-55; Mihai et al., 2006, *J. Mol. Biol.* 361:864-76). The role of DDR2 in regulation of the extracellular matrix suggests that dysregulation of DDR signaling may contribute to human carcinogenesis, including invasion and metastasis. DDR1 is also activated by collagen, including all types tested (types I-VI and VIII) (Vogel, 1999, *FASEB* 13:S77-S82; Curat et al., 2001, *J. Biol. Chem.* 276:45952-45958).

DDR2 signaling regulates proliferation of various cell populations including chondrocytes and fibroblasts (Labrador et al., 2001, *EMBO Rep.* 2:446-52). DDR2 is induced in hepatic stellate cells in response to collagen during liver injury, and over-expression of DDR enhanced hepatic stellate cell proliferation, activated expression of MMP-2, and enhanced cellular invasion through Matrigel™ (Olaso et al., 2001, *J. Clin. Invest.* 108:1369-78). DDR activation and adhesion in response to collagen may require Wnt and G-protein signaling (Dejmek et al., 2003, *Int. J. Cancer* 103:344-51).

DDR receptors are implicated in cancer. DDR1 is over-expressed in numerous human tumors including breast, ovarian, esophageal, and brain cancers (Barker et al., 1995, Oncogene 11:569-75; Laval et al., 1994, *Cell Growth Dif* 5:1173-83; Nemoto et al., 1997, *Pathobiol.* 65:165-203; Weiner et al., 1996, *Pediatr. Neurosurg.* 25:64-72; Weiner et al., 2000, *Neurosurgery* 47:1400-9; Heinzelmaun et al., 2004, 10:4427-36). DDR1 and DDR2 have mutually exclusive expression in ovarian and lung tumors, with transcripts for DDR1 in highly invasive tumor cells and transcripts for DDR2 detected in the surrounding stromal cells (Alves et al., 1995, *Oncogene* 10:609-18). DDR2 expression is also associated with invasive mammary carcinomas (Evitmova et al., 2003, *Tumour Biol.* 24:189-98).

In some aspects, the invention provides agents (e.g., antibodies) that bind to and/or modulate the activity of DDR1 and compositions, such as pharmaceutical compositions, comprising those agents. The invention also provides methods of targeting cancer stem cells with the agents and/or reducing the tumorigenicity of tumors comprising cancer stem cells. The invention further provides methods of using the agents in the treatment of cancer and in the inhibition of the growth of tumors comprising cancer stem cells.

In one aspect, the invention provides a method of inhibiting the growth of a tumor in a subject, wherein the tumor comprises cancer stem cells, comprising administering to the subject a therapeutically effective amount of an agent that modulates the activity of DDR1. In certain embodiments, the agent reduces tumorigenicity of the tumor by reducing the number or frequency of cancer stem cells in the tumor. In certain embodiments, the agent is an antibody, such as an antibody that specifically binds to DDR1. In certain embodiments, the tumor is selected from the group consisting of a breast tumor, colorectal tumor, hepatic tumor, renal tumor, lung tumor, pancreatic tumor, ovarian tumor, prostate tumor, and head and neck tumor. In certain embodiments, the tumor expresses LGR5. In certain embodiments, the tumor expresses LGR5 and the tumor is a colorectal tumor, hepatic tumor, ovarian tumor, or pancreatic tumor. In certain embodiments, the cancer stem cells express LGR5. In certain embodiments, the cancer stem cells express LGR5 and the tumor is a colorectal tumor, hepatic tumor, ovarian tumor, or pancreatic tumor. In certain embodiments, the tumor expresses Hes1. In certain embodiments, the tumor expresses Hes1 and the tumor is a breast tumor, colorectal tumor, renal tumor, lung tumor, pancreatic tumor, or prostate tumor. In certain embodiments, the cancer stem cells express Hes1. In certain embodiments, the cancer stem cells express Hes1 and the tumor is a breast tumor, colorectal tumor, renal tumor, lung tumor, pancreatic tumor, or prostate tumor. In certain embodiments, the subject is a human.

In certain embodiments, the invention provides a method of inhibiting growth of a tumor in a subject, comprising administering to the subject a therapeutically effective amount of an agent or antibody that competes with an antibody that binds to at least one amino acid in the sequence SASSSWSDSTAAR (SEQ ID NO:30) within DDR1. In some embodiments the agent or antibody specifically binds to at least one amino acid in the sequence SASSSWSDSTAAR (SEQ ID NO:30) within DDR1. In some embodiments, the antibody further binds to additional amino acid residues within DDR1.

In another aspect, the invention provides a method of reducing the tumorigenicity of a tumor comprising cancer stem cells by reducing the number or frequency of cancer stem cells in the tumor, wherein the method comprises contacting the tumor with an effective amount of an agent that modulates the activity of DDR1. In certain embodiments, the agent is an antibody, including, but not limited to, an antibody that specifically binds to DDR1. In certain embodiments, the tumor is a tumor selected from the group consisting of breast tumor, colorectal tumor, hepatic tumor, renal tumor, lung tumor, pancreatic tumor, ovarian tumor, prostate tumor, and head and neck tumor. In certain embodiments, the tumor expresses LGR5. In certain embodiments, the cancer stem cells express LGR5. In certain embodiments, the cancer stem cells express LGR5 and the tumor is colorectal tumor, hepatic tumor, ovarian tumor, or pancreatic tumor. In certain embodiments, the tumor expresses Hes1. In certain embodiments, the cancer stem cells express Hes1. In certain embodiments, the cancer stem cells express Hes1 and the tumor is breast tumor, colorectal tumor, renal tumor, lung tumor, pancreatic tumor, or prostate tumor. In some embodiments, the method is an in vivo method.

In another aspect, the invention provides an antibody that modulates the activity of DDR1. In certain embodiments, the antibody specifically binds to DDR1. In some embodiments, the antibody binds the extracellular domain of DDR1. In certain embodiments, the antibody binds the discoidin domain of DDR1. In certain embodiments, the antibody binds a region of DDR1 comprising amino acids 21 to 241 of SEQ ID NO:2. In certain embodiments, the antibody preferentially binds a human DDR1 relative to one or more mutants or variants of the human DDR1. For example, in certain embodiments, the antibody preferentially binds human DDR1 (for example, the DDR1 in SEQ ID NO:37) as compared to a W53A variant of DDR1 (for example, the variant DDR1 of SEQ ID NO:39). In some embodiments, the antibody binds to at least one amino acid in the sequence SASSSWSDSTAAR (SEQ NO ID:30). In some embodiments, the agent or antibody competes with an antibody that binds to at least one amino acid in the sequence SASSSWSDSTAAR (SEQ NO ID:30). In some embodiments, the antibody has reduced binding to a variant of DDR1 in which the sequence SASSSWSDSTAAR (SEQ NO ID:30) has been replaced with the sequence SASSSASDSTAAR (SEQ IS NO:31).

In certain embodiments, the antibody reduces the tumorigenicity of a tumor that comprises cancer stem cells. In certain embodiments, the antibody that modulates DDR1 inhibits growth of a tumor comprising cancer stem cells. In certain embodiments, the tumor cells express LGR5 and/or Hes1. In certain embodiments, the cancer stem cells express LGR5 and/or Hes1.

In certain embodiments, the agent or antibody is capable of reducing the tumorigenicity of a tumor comprising cancer stem cells in an animal model, such as a mouse xenograft model.

In certain embodiments, the number or frequency of cancer stem cells in the tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. An example of a limiting dilution assay used to test the efficacy of an anti-DDR1 antibody is provided in Example 12, below. Additional examples and guidance regarding the use of limiting dilution assays to determine a reduction in the number or frequency of cancer stem cells in a tumor can be found, e.g., in International Publication Number WO 2008/042236, U.S. Patent Application Publication No. 2008/0064049, and U.S. Patent Application Publication No. 2008/0178305, each of which is incorporated by reference herein in its entirety.

In certain embodiments, the agent or antibody is an antagonist of DDR1. In some embodiments, the term "antagonist" includes any molecule that partially or fully blocks, inhibits, or neutralizes a biological activity of a DDR1 and/or DDR2 protein or fragment thereof. In some embodiments, the antagonist molecules specifically include antagonist antibodies. In some embodiments, the term "antagonist" includes any molecule that partially or fully blocks, inhibits, or neutralizes the expression of DDR1, and/or DDR2 protein or fragment thereof.

In certain embodiments, the agent or antibody inhibits the binding of a ligand to DDR1. In some embodiments, the agent or antibody inhibits the binding of collagen to DDR1. In certain embodiments, the agent or antibody inhibits or blocks collagen-induced tyrosine phosphorylation of DDR1. In certain embodiments, the agent or antibody binds to at least one amino acid in the sequence SASSSWSDSTAAR (SEQ ID NO:30) within DDR1 and inhibits tyrosine phosphorylation of DDR1. In certain embodiments, the collagen is selected from the group consisting of collagen type I, collagen type II, collagen type III, collagen type IV and collagen type V.

In certain embodiments, DDR1 is human DDR1. In certain embodiments, DDR1 is selected from the group consisting of DDR1a, DDR1b, DDR1c, DDR1d, and DDR1e. In certain embodiments, DDR1 is SEQ ID NO:2, 9, 12, 14, or 37.

In certain embodiments, the antibody specifically binds to the extracellular domain of DDR1. In certain embodiments, the antibody binds the discoidin domain of DDR1 (SEQ ID NO:41). The discoidin domain is from about amino acid residue 30 to about amino acid residue 185 of DDR1.

In certain embodiments, the antibody that specifically binds to and/or modulates the activity of DDR1, further specifically binds to and/or modulates the activity of DDR2. In some embodiments, the antibody binds the extracellular domain of DDR2. In certain embodiments, the antibody binds the discoidin domain of DDR2. In certain embodiments, the antibody binds a region of DDR2 comprising amino acids 24 to 241 of SEQ ID NO:3. In certain embodiments, the antibody preferentially binds a human DDR2 (e.g., SEQ ID NO:3) relative to one or more mutants of the human DDR2 selected from the group consisting of W52A, D69A, and R105A. For instance, in certain embodiments, the antibody preferentially binds human DDR2 of SEQ ID NO:3 relative to the W52A mutant or the D69A mutant of DDR2.

In certain embodiments, the antibody is an antagonist of DDR2 and/or inhibits the binding of collagen to DDR2.

In certain embodiments, the antibodies are isolated. In certain embodiments, the antibodies are substantially purified.

In certain embodiments, the antibody is an IgG1 antibody or an IgG2 antibody. In certain embodiments, the antibody is an IgG1 antibody. In certain embodiments, the antibody is an IgG2 antibody.

In certain embodiments, the antibody does not have one or more effector functions. For instance, in some embodiments, the antibody has no antibody-dependent cellular cytotoxicity (ADCC) activity, and/or no complement-dependent cytotoxicity (CDC) activity. In certain embodiments, the antibody does not bind to an Fc receptor and/or complement factors. In certain embodiments, the antibody has no effector function.

In certain embodiments, the antibody is a monoclonal antibody, a chimeric antibody, a humanized antibody, or a human antibody. In certain embodiments, the antibody is an antibody fragment. In certain embodiments, the antibody is conjugated to a cytotoxic agent.

In certain embodiments, the treatment methods further comprise administering at least one additional therapeutic agent appropriate for effecting combination therapy (e.g., a chemotherapeutic agent or other anticancer agent if cancer is to be treated). In certain embodiments, the additional therapeutic agent is irinotecan or gemcitabine. In certain embodiments, the additional therapeutic agent is irinotecan. In certain embodiments, the additional therapeutic agent is gemcitabine.

The present invention further provides methods of identifying and/or isolating cancer stem cells (e.g., based on expression of DDR1), screening for anti-cancer agents, and screening patients for suitability for treatment with the agents described herein.

Expression of DDR1 can be used to identify subjects having cancers suitable for treatment with the compositions of the invention. In some embodiments, expression of a cancer stem cell marker is determined by polynucleotide expression such as, for example, mRNA encoding the cancer stem cell marker. The polynucleotide can be detected and quantified by any of a number of means well known to those of skill in the art. In some embodiments, mRNA encoding a cancer stem cell marker is detected by in situ hybridization of tissue sections from, for example, a patient biopsy. In some embodiments, RNA is isolated from a tissue and detected by, for example, Northern blot, quantitative RT-PCR, or microarrays. For example, total RNA can be extracted from a tissue sample and primers that specifically hybridize and amplify a cancer stem cell marker can be used to detect expression of a cancer stem cell marker polynucleotide using RT-PCR.

In certain embodiments, expression of a cancer stem cell marker can be determined by detection of the corresponding polypeptide. The polypeptide can be detected and quantified by any of a number of means well known to those of skill in the art. In some embodiments, a cancer stem cell marker polypeptide is detected using analytic biochemical methods such as, for example, electrophoresis, capillary electrophoresis, high performance liquid chromatography (HPLC) or thin layer chromatography (TLC). The isolated polypeptide can also be sequenced according to standard techniques. In some embodiments, a cancer stem cell marker protein is detected with antibodies raised against the protein using, for example, immunofluorescence or immunohistochemistry on tissue sections. Alternatively antibodies against a cancer stem cell marker can detect expression using, for example, ELISA, FACS, Western blot analysis, immunoprecipitation or protein microarrays. For example, cancer stem cells can be isolated from a patient biopsy and expression of a cancer stem cell marker protein detected with fluorescently labeled antibodies using FACS. In another method, the cells expressing a cancer stem cell marker can be detected in vivo using labeled antibodies in a typical imaging system. For example, antibodies labeled with paramagnetic isotopes can be used for magnetic resonance imaging (MRI).

In some embodiments of the present invention, a diagnostic assay comprises determining the expression or not of a cancer stem cell marker using, for example, immnunohistochemistry, in situ hybridization, or RT-PCR. In other embodiments, a diagnostic assay comprises determining expression levels of a cancer stem cell marker using, for example, quantitative RT-PCR. In some embodiments, a diagnostic assay further comprises determining expression levels of a cancer stem cell marker compared to a control tissue such as, for example, normal epithelium.

Detection of a cancer stem cell marker expression can then be used to select a therapy. A prognosis can be based on any known risk expression of a cancer stem cell marker indicates.

Furthermore, detection of a cancer stem cell marker can be used to select an appropriate therapy including, for example, treatment with antibodies against the detected cancer stem cell marker protein. In certain embodiments, the antibody specifically binds to the cancer stem cell marker protein human DDR1. In certain embodiments, the antibody further specifically binds to the extracellular domain of DDR2.

In some embodiments, a suitable antibody or agent is one that can have one or more of the following effects, for example: interfere with the expression of a cancer stem cell marker; interfere with activation of a cancer stem cell signal transduction pathway by, for example, sterically inhibiting interactions between a cancer stem cell marker and its ligand, receptor or co-receptors; activate a cancer stem cell signal transduction pathway by, for example, acting as a ligand or promoting the binding of an endogenous ligand; or bind to a cancer stein cell marker and inhibit tumor cell proliferation.

In certain embodiments, antibodies against a cancer stem cell marker act extracellularly to modulate the function of a cancer stem cell marker protein. In some embodiments, extracellular binding of an antibody against a cancer stem cell marker can inhibit the signaling of a cancer stem cell marker protein by, for example, inhibiting intrinsic activation (e.g. kinase activity) of a cancer stem cell marker and/or by sterically inhibiting the interaction, for example, of a cancer stem cell marker with its ligand, with its receptor, with a co-receptor, or with the extracellular matrix. In some embodiments, extracellular binding of an antibody against a cancer stem cell marker can down-regulate cell-surface expression of a cancer stem cell marker such as, for example, by internalization of a cancer stem cell marker protein or decreasing cell surface trafficking of a cancer stem cell marker. In some embodiments, extracellular binding of an antibody against a cancer stem cell marker can promote the signaling of a cancer stem cell marker protein by, for example, acting as a decoy ligand or increasing ligand binding.

In certain embodiments, antibodies against a cancer stem cell marker bind to a cancer stem cell marker protein and have one or more of the following effects: inhibit proliferation, trigger cell death, or prevent metastasis. In certain embodiments, antibodies against a cancer stem cell marker trigger cell death via a conjugated toxin, chemotherapeutic agent, radioisotope, or other such agent. For example, an antibody against a cancer stem cell marker is conjugated to a toxin that is activated in cells expressing the cancer stem cell marker by protein internalization. In certain embodiments, antibodies against a cancer stem cell marker mediate cell death of a cell expressing the cancer stem cell marker protein via antibody-dependent cellular cytotoxicity (ADCC). ADCC involves cell lysis by effector cells that recognize the Fc portion of an antibody. Many lymphocytes, monocytes, tissue macrophages, granulocytes and eosinophils, for example, have Fc receptors and can mediate cytolysis (Dillman, 1994, *J. Clin. Oncol.* 12:1497).

In certain embodiments, antibodies against a cancer stem cell marker trigger cell death of a cell expressing a cancer stem cell marker protein by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity are prepared.

The ability of any particular antibody against a cancer stem cell to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, antibodies against a cancer stem cell marker can trigger cell death inhibiting angiogenesis. Angiogenesis is the process by which new blood vessels form from pre-existing vessels and is a fundamental process required for normal growth, for example, during embryonic development, wound healing, and in response to ovulation. Solid tumor growth larger than 1-2 $mm^2$ also requires angiogenesis to supply nutrients and oxygen without which tumor cells die. In certain embodiments, an antibody against a cancer stem cell marker targets vascular cells that express the cancer stem cell marker including, for example, endothelial cells, smooth muscle cells, or components of the extracellular matrix required for vascular assembly. In certain embodiments, an antibody against a cancer stem cell marker inhibits growth factor signaling required by vascular cell recruitment, assembly, maintenance, or survival.

The antibodies against a cancer stem cell marker find use in the diagnostic and therapeutic methods described herein. In certain embodiments, the antibodies of the present invention are used to detect the expression of a cancer stem cell marker protein in biological samples such as, for example, a patient tissue biopsy, pleural effusion, or blood sample. Tissue biopsies can be sectioned and protein detected using, for example, immunofluorescence or immunohistochemistry. In addition, individual cells from a sample can be isolated, and protein expression detected on fixed or live cells by FACS analysis. In certain embodiments, antibodies can be used on protein arrays to detect expression of a cancer stem cell marker, for example, on tumor cells, in cell lysates, or in other protein samples. In certain embodiments, the antibodies of the present invention are used to inhibit the growth of tumor cells by contacting the antibodies with tumor cells in in vitro cell based assays, in vivo animal models, etc. In certain embodiments, the antibodies are used to treat cancer in a patient by administering a therapeutically effective amount of an antibody against a cancer stem cell marker.

The antibodies of the present invention can be prepared by any conventional means known in the art. For example, polyclonal antibodies can be prepared by immunizing an animal (e.g., a rabbit, rat, mouse, goat, donkey, etc.) by multiple subcutaneous or intraperitoneal injections of the relevant antigen (a purified peptide fragment, full-length recombinant protein, fusion protein, etc) optionally conjugated to keyhole limpet hemocyanin (KLH), serum albumin, etc. diluted in sterile saline and combined with an adjuvant (e.g., Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein, 1975, *Nature* 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

In some embodiments of the present invention, the antibody is an antibody which specifically binds to an extracellular domain of human DDR1. In some embodiments, the antibody comprises a heavy chain variable region having at least 90% sequence identity to SEQ ID NO:33; and/or a light chain variable region having at least 90% sequence identity to SEQ ID NO:35. In some embodiments, the antibody comprises a heavy chain variable region having at least 95% sequence identity to SEQ ID NO:33, and/or a light chain variable region having at least 95% sequence identity to SEQ ID NO:35. In some embodiments, the antibody comprises a heavy chain variable region comprising the sequence of SEQ ID NO:33, and/or a light chain variable region comprising the sequence of SEQ ID NO:35. In some embodiments, the antibody is a monoclonal antibody or antibody fragment.

In other embodiments, the antibody comprises a heavy chain CDR1 comprising GYTFTDYFMK (SEQ ID NO:22), a heavy chain CDR2 comprising DINPNNGDTFYIQKFKG (SEQ ID NO:23), and/or a heavy chain CDR3 comprising SRDLAY (SEQ ID NO:24). In some embodiments, the antibody further comprises a light chain CDR1 comprising KSSQSLLYSNGKTYLN (SEQ ID NO:27), a light chain CDR2 comprising QVSKLDS (SEQ ID NO:28), and/or a light chain CDR3 comprising VQGTDFPQT (SEQ ID NO:29). In other embodiments, the antibody comprises a light chain CDR1 comprising KSSQSLLYSNGKTYLN (SEQ ID NO:27), a light chain CDR2 comprising QVSKLDS (SEQ ID NO:28), and/or a light chain CDR3 comprising VQGTDFPQT (SEQ ID NO:29).

In other embodiments, the antibody comprises (a) a heavy chain CDR1 comprising GYTFTDYFMK (SEQ ID NO:22), a heavy chain CDR2 comprising DINPNNGDTFYIQKFKG (SEQ ID NO:23), and a heavy chain CDR3 comprising SRDLAY (SEQ ID NO:24); and/or (b) a light chain CDR1 comprising KSSQSLLYSNGKTYLN (SEQ ID NO:27), a light chain CDR2 comprising QVSKLDS (SEQ ID NO:28), and a light chain CDR3 comprising VQGTDFPQT (SEQ ID NO:29).

In certain embodiments of the invention, the antibody comprises a heavy chain variable region comprising (a) a heavy chain CDR1 comprising GYTFTDYFMK (SEQ ID NO:22), or a variant thereof comprising 1, 2, 3 or 4 amino acid substitutions; (b) a heavy chain CDR2 comprising DINPNNGDTFYIQKFKG (SEQ ID NO:23), or a variant thereof comprising 1, 2, 3 or 4 amino acid substitutions; and/or (c) a heavy chain CDR3 comprising SRDLAY (SEQ ID NO:24), or a variant thereof comprising 1, 2, 3 or 4 amino acid substitutions. In other embodiments, the antibody further comprises a light chain variable region comprising (a) a light chain CDR1 comprising KSSQSLLYSNGKTYLN (SEQ ID NO:27), or a variant thereof comprising 1, 2, 3 or 4 amino acid substitutions; (b) a light chain CDR2 comprising QVSKLDS (SEQ ID NO:28), or a variant thereof comprising 1, 2, 3 or 4 amino acid substitutions; and/or (c) a light chain CDR3 comprising VQGTDFPQT (SEQ ID NO:29), or a variant thereof comprising 1, 2, 3 or 4 amino acid substitutions. In some embodiments, the amino acid substitutions are conservative amino acid substitutions.

In some embodiments, the invention provides a monoclonal antibody, 20M102, produced by the hybridoma cell line deposited as ATCC deposit number PTA-10051. In some embodiments, the invention provides an antibody comprising the same heavy and light chain variable regions as the antibody 20M102. In some embodiments, the invention provides an antibody that is a humanized version of 20M102. In some embodiments, the invention provides an antibody which specifically binds to the same DDR1 epitope as the epitope to which antibody 20M102 binds. In certain embodiments, the invention provides an antibody which specifically competes with any antibody that binds to at least one amino acid in the sequence SASSSWSDSTAAR (SEQ ID NO:30) within DDR1. In other embodiments, the invention provides an antibody which specifically competes with any of the antibodies as described in the aforementioned aspects and embodiments, as well as other embodiments herein.

Alternatively monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, *Nature* 348:552-554; Clackson et al., 1991, *Nature* 352:624-628; and Marks et al., 1991, *J. Mol. Biol.* 222:581-597). The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody, can be substituted 1) for those regions of, for example, a human antibody to generate a chimeric antibody, or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments of the present invention, the monoclonal antibody against a cancer stem cell marker is a humanized antibody. Humanized antibodies are antibodies that contain minimal sequences from non-human (e.g., murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g., mouse, rat, rabbit, hamster, etc.) having the desired specificity, affinity, and/or capability (Jones et al., 1986, *Nature* 321:522-525; Riechmann et al., 1988, *Nature* 332:323-327; Verhoeyen et al., 1988, *Science* 239:1534-1536). The humanized antibody can be further modified by the substitution of additional residues either in the Fv framework region and/or within the replaced non-human residues to refine and optimize antibody specificity, affinity, and/or capability.

In addition, fully human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, *J. Immunol.* 147 (1):86-95; and U.S. Pat. No. 5,750,373). Also, the human antibody can be selected from a phage library, where that phage library expresses human antibodies (Vaughan et al., 1996, *Nat. Biotech.* 14:309-314; Sheets et al., 1998, *Proc. Nat'l. Acad. Sci.* 95:6157-6162; Hoogenboom and Winter, 1991, *J, Mol. Biol.* 227:381; Marks et al., 1991, *J. Mol. Biol.* 222:581). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a cancer stem cell marker. Bispecific antibodies are antibodies that are capable of specifically recognizing and binding at least two different epitopes. The different epitopes can either be within the same molecule (e.g., the same cancer stem cell marker polypeptide) or on different molecules such that both, for example, the antibodies can specifically recognize and bind a cancer stem cell marker as well as, for example, 1) an effector molecule on a leukocyte such as a T-cell receptor (e.g., CD3) or Fc receptor (e.g., CD64, CD32, or CD16) or 2) a cytotoxic agent as described in detail below. Bispecific antibodies can be intact antibodies or antibody fragments.

Exemplary bispecific antibodies can bind to two different epitopes, at least one of which originates in DDR1. Alternatively, an anti-antigenic arm of an immunoglobulin molecule can be combined with an arm which binds to a triggering molecule on a leukocyte such as a T cell receptor molecule (e.g., CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, *Nature* 305:537-539; Brennan et al., 1985, *Science* 229:81; Suresh et al, 1986, *Methods in Enzymol.* 121:120; Traunecker et al., 1991, *EMBO J.* 10:3655-3659; Shalaby et al., 1992, *J. Exp. Med.* 175:217-225: Kostelny et al., 1992, *J. Immunol.* 148:1547-1553; Gruber et al., 1994, *J. Immunol.* 152:5368; and U.S. Pat. No. 5,731,168). Antibodies with more than two valencies are also contemplated. For example, trispecific antibodies can be prepared (Tutt et al., 1991, *J. Immunol.* 147:60)

In certain embodiments is provided an antibody fragment to, for example, increase tumor penetration. Various techniques are known for the production of antibody fragments. Traditionally, these fragments are derived via proteolytic digestion of intact antibodies (for example Morimoto et al., 1993, *Journal of Biochemical and Biophysical Methods,* 24:107-117; Brennan et al., 1985, *Science* 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to DDR1 (see U.S. Pat. No. 4,946,778). In addition, methods can be adapted for the construction of Fab expression libraries (Huse, et al., 1989, *Science* 246:1275-1281) to allow rapid and effective identification of monoclonal Fab fragments with the desired specificity for DDR1, or derivatives, fragments, or homologs thereof. Antibody fragments that contain the idiotypes to a polypeptide of the invention may be produced by techniques in the art including, but not limited to: (a)

an F(ab')2 fragment produced by pepsin digestion of an antibody molecule; (b) an Fab fragment generated by reducing the disulfide bridges of an F(ab')2 fragment, (c) an Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of DDR1 (and/or DDR2). In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g., cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

The variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In some embodiments the modified antibodies will comprise domain deleted constructs or variants wherein the entire CH2 domain has been removed (ΔCH2 constructs). In some embodiments the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques well within the purview of the skilled artisan.

It will be noted that the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, any spacer added to the construct should be relatively non-immunogenic or, even omitted altogether if the desired biochemical qualities of the modified antibodies may be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the antibodies can be conjugated to radioisotopes, such as $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using any one of a number of well known chelators or direct labeling. In other embodiments, the disclosed compositions can comprise antibodies coupled to drugs, prodrugs or lymphokines such as interferon. Conjugates of the antibody and cytotoxic agent are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Conjugates of an antibody and one or more small molecule toxins, such as a calicheamicin, maytansinoids, a trichothene, and CC 1065, and the derivatives of these toxins that have toxin activity, can also be used. In some embodiments, the modified antibodies can be complexed with other immunologically active ligands (e.g. antibodies or fragments thereof) wherein the resulting molecule binds to both the neoplastic cell and an effector cell such as a T cell.

Conjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. The selection of which conjugated or unconjugated modified antibody to use will depend on the type and stage of cancer, use of adjunct treatment (e.g., chemotherapy or external radiation) and patient condition. It will be appreciated that one skilled in the art could readily make such a selection in view of the teachings herein.

Competition assays can be used to determine whether two antibodies bind the same epitope by recognizing identical or sterically overlapping epitopes. Any method known in the art for determining competitive binding (such as e.g., the immunoassays described elsewhere herein) may be used.

The antibodies of the present invention can be assayed for immunospecific binding by any method known in the art. The immunoassays which can be used include, but are not limited to, competitive and non-competitive assay systems using techniques such as Biacore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

In some embodiments, the immunospecificity of an antibody against a cancer stem cell marker is determined using ELISA. An ELISA assay comprises preparing antigen, coating wells of a 96 well microtiter plate with antigen, adding the antibody against a cancer stem cell marker conjugated to a detectable compound such as an enzymatic substrate (e.g. horseradish peroxidase or alkaline phosphatase) to the well, incubating for a period of time and detecting the presence of the antigen. In some embodiments, the antibody against a cancer stem cell marker is not conjugated to a detectable compound, but instead a second conjugated antibody that recognizes the antibody against a cancer stem cell marker is added to the well. In some embodiments, instead of coating the well with the antigen, the antibody against a cancer stem cell marker can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g., Ausubel et al., eds., 1994, Current Protocols in Molecular Biology, Vol. 1, John Wiley & Sons, Inc., New York at 11.2.1).

The binding affinity of an antibody to a cancer stem cell marker antigen and the off-rate of an antibody-antigen interaction can be determined by competitive binding assays. One example of a competitive binding assay is a radioimmunoassay comprising the incubation of labeled antigen (e.g. $^{3}H$ or $^{125}I$), or fragment or variant thereof, with the antibody of interest in the presence of increasing amounts of unlabeled antigen followed by the detection of the antibody bound to the labeled antigen. The affinity of the antibody against a cancer stem cell marker and the binding off-rates can be determined from the data by Scatchard plot analysis. In some embodiments, Biacore kinetic analysis is used to determine the binding on and off rates of antibodies against a cancer stem cell marker. Biacore kinetic analysis comprises analyzing the binding and dissociation of antibodies from chips with immobilized cancer stem cell marker antigens on their surface.

In certain embodiments, the invention encompasses isolated polynucleotides that encode a polypeptide comprising an antibody, or fragment thereof, against human DDR1. Thus, the term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The present invention further relates to variants of the hereinabove described polynucleotides encoding, for example, fragments, analogs, and derivatives. The variant of the polynucleotide can be a naturally occurring allelic variant of the polynucleotide or a non-naturally occurring variant of the polynucleotide. In certain embodiments, the polynucleotide can have a coding sequence which is a naturally occurring allelic variant of the coding sequence of the disclosed polypeptides. As known in the art, an allelic variant is an alternate form of a polynucleotide sequence that has, for example, a substitution, deletion, or addition of one or more nucleotides, which does not substantially alter the function of the encoded polypeptide.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

In certain embodiments, the present invention provides isolated nucleic acid molecules having a nucleotide sequence at least 80% identical, at least 85% identical, at least 90% identical, at least 95% identical, and in some embodiments, at least 96%, 97%, 98% or 99% identical to a polynucleotide encoding a polypeptide comprising an antibody, or fragment thereof, against DDR1 (e.g., human DDR1).

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, 1981, *Advances in Applied Mathematics* 2: 482 489 to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The polypeptides of the present invention can be recombinant polypeptides, natural polypeptides, or synthetic polypeptides comprising an antibody, or fragment thereof, against a DDR1 protein, such as human DDR1. It will be recognized in the art that some amino acid sequences of the invention can be varied without significant effect of the structure or function of the protein. Thus, the invention further includes variations of the polypeptides which show substantial activity or which include regions of an antibody, or fragment thereof, against human DDR1 protein. Such mutants include deletions, insertions, inversions, repeats, and type substitutions.

The polypeptides and analogs can be further modified to contain additional chemical moieties not normally part of the protein. The derivatized moieties can improve the solubility, the biological half life or absorption of the protein. The moieties can also reduce or eliminate any undesirable side effects of the proteins and the like. An overview for such moieties can be found in Remington's Pharmaceutical Sciences, 20th ed., Mack Publishing Co., Easton, Pa. (2000).

The isolated polypeptides described herein can be produced by any suitable method known in the art. Such methods range from direct protein synthesis methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. (See, e.g., Zoeller et al., *Proc. Nat'l. Acad Sci. USA* 81:5662-5066 (1984) and U.S. Pat. No. 4,588,585).

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced.

Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

Recombinant expression vectors are used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives and wider host range plasmids, such as M13 and filamentous single-stranded DNA phages.

Suitable host cells for expression of a cancer stem cell marker protein include prokaryotes, yeast, insect or higher eukaryotic cells. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (1981 *Cell* 23:175), and other cell lines capable of expressing an appropriate vector including, for example, L cells, C127, 3T3, Chinese hamster ovary (CHO), HeLa and BHK cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, 1988, *Bio/Technology,* 6:47.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexa-histidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a recombinant protein or cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

The present invention provides methods for inhibiting the growth of tumorigenic cells expressing a cancer stem cell marker using the antibodies against a cancer stem cell marker described herein. In certain embodiments, the method of inhibiting the growth of tumorigenic cells expressing a cancer stem cell marker comprises contacting the cell with an antibody against a cancer stein cell marker in vitro. For example, an immortalized cell line or a cancer cell line that expresses a cancer stem cell marker is cultured in medium to which is added an antibody against the expressed cancer stem cell marker to inhibit cell growth. In some embodiments, tumor cells comprising tumor stem cells are isolated from a patient sample such as, for example, a tissue biopsy, pleural effusion, or blood sample and cultured in medium to which is added an antibody against a cancer stem cell marker to inhibit cell growth.

In some embodiments, the method of inhibiting the growth of tumorigenic cells expressing a cancer stem cell marker comprises contacting the cell with an antibody against a cancer stem cell marker in vivo. In some embodiments, the method of inhibiting growth of tumorigenic cells expressing DDR1 comprises contacting the cell with an antibody that specifically binds the extracellular domain of DDR1. In some embodiments, the anti-DDR1 antibody inhibits growth of tumorigenic cells by inhibiting the activity of DDR1. In some embodiments, the anti-DDR1 antibody inhibits growth of tumorigenic cells by reducing the frequency of or the number of cancer stem cells in the tumor.

In some embodiments, the present invention provides methods of inhibiting activity of DDR1 on a cell comprising contacting the cell with an effective amount of an antibody that specifically binds the extracellular domain of DDR1. In certain embodiments, the cell is a tumor cell.

In certain embodiments, contacting a tumorigenic cell with an antibody against a cancer stem cell marker is undertaken in an animal model. For example, xenografts expressing a cancer stem cell marker are grown in immunocompromised mice (e.g. NOD/SCID mice) that are administered an antibody against a cancer stem cell marker to inhibit tumor growth. In some embodiments, cancer stem cells that express a cancer stem cell marker are isolated from a patient sample such as, for example, a tissue biopsy, pleural effusion, or blood sample and injected into immunocompromised mice that are then administered an antibody against the cancer stem cell marker to inhibit growth of a solid tumor. In some embodiments, the antibody against a cancer stem cell marker is administered at the same time or shortly after introduction of tumorigenic cells into the animal to prevent tumor growth. In some embodiments, the antibody against a cancer stem cell marker is administered as a therapeutic after the tumorigenic cells have grown to a specified size.

The present invention further provides pharmaceutical compositions comprising antibodies, polypeptides or other agents that target a cancer stem cell marker. These pharmaceutical compositions find use in inhibiting growth of a solid tumor and treating cancer in human patients.

Formulations are prepared for storage and use by combining a purified agent or antibody of the present invention with a pharmaceutically acceptable vehicle (e.g., carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer, intratracheal, intranasal, epidermal and transdermal); oral; or parenteral including intravenous, intraarterial, subcutaneous, intraperitoneal or intramuscular injection or infusion; intratumoral, or intracranial (e.g., intrathecal or intraventricular) administration.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g. water) to form a solid preformulation composition containing a homogeneous mixture of a compound of the present invention, or a non-toxic pharmaceutically acceptable salt thereof. The solid preformulation composition is then subdivided into unit dosage forms of the type described above. The tablets, pills, etc. of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antibodies of the present invention complexed with liposomes (Epstein, et al., 1985, *Proc. Natl. Acad. Sci. USA* 82:3688; Hwang, et al., 1980, *Proc. Natl. Acad. Sci. USA* 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antibodies can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semi-permeable matrices of solid hydrophobic polymers containing the antibody, which matrices are in the form of shaped articles (e.g. films or microcapsules). Examples of sustained-release matrices include polyesters, hydrogels such as poly (2-hydroxyethyl-methacrylate) or poly(vinylalcohol), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

In some embodiments, the treatment involves the combined administration of an antibody or other agent of the present invention and a chemotherapeutic agent or cocktail of multiple different chemotherapeutic agents. Combination therapy often uses agents that work by different mechanisms of action. Combination therapy using agents with different mechanisms of action often results in additive or synergetic effects. Combination therapy may allow for lower doses of each agent than is used in monotherapy thereby reducing toxic side effects. Combination therapy may decrease the likelihood that resistant cancer cells will develop. In some embodiments, the combination therapy comprises an antibody that binds to DDR1 and a chemotherapeutic agent.

In combination therapy, treatment with an antibody can occur prior to, concurrently with, or subsequent to administration of chemotherapies. Chemotherapies contemplated by the invention include chemical substances or drugs which are known in the art and are commercially available, such as doxorubicin, 5-fluorouracil, cytosine arabinoside ("Ara-C"), cyclophosphamide, thiotepa, busulfan, cytoxin, taxol (paclitaxel), methotrexate, cisplatin, melphalan, vinblastine, leucovorin, streptozocin, oxaliplatin and carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

Chemotherapeutic agents useful in the instant invention also include, but are not limited to, alkylating agents such as thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL, Bristol-Myers Squibb Oncology, Princeton, N.J.) and doxetaxel (TAXOTERE, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT 11; topoisomerase inhibitor RFS 2000; difluoromethylornithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCL, daunorubicin citrate, mitoxantrone HCL, actinomycin D, etoposide, topotecan HCl, teniposide (VM-26), and irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, Pemetrexed, tegafur, cytosine arabinoside, THIOGUANINE (GlaxoSmithKline), 5-azacytidine, 6-mercaptopurine, azathioprine, 6-thioguanine, pentostatin, fludarabine phosphate, and cladribine, as well as pharmaceutically acceptable salts, acids, or derivatives of any of these.

In other embodiments, the treatment involves the combined administration of an antibody or other agent of the present invention and radiation therapy. Treatment with the antibody can occur prior to, concurrently with, or subsequent to administration of radiation therapy. Any dosing schedules for such radiation therapy can be used as determined by the skilled practitioner.

In other embodiments, the treatment can involve the combined administration of antibodies of the present invention with other antibodies against additional tumor-associated antigens including, but not limited to, antibodies that bind to the EGF receptor (EGFR) (Erbitux® Bristol-Myers Squibb Company, Princeton, N.J.), the erbB2 receptor (HER2) (Herceptin® Genentech, Inc., South San Francisco, Calif.), and vascular endothelial growth factor (VEGF) (Avastin® Genentech, Inc., South San Francisco, Calif.). Furthermore, treatment can include administration of one or more cytokines; can be accompanied by surgical removal of cancer cells; or any other therapy deemed necessary by a treating physician.

For the treatment of the disease, the appropriate dosage of an agent or antibody of the present invention depends on the type of disease to be treated, the severity and course of the disease, the responsiveness of the disease, whether the antibody is administered for therapeutic or preventative purposes, previous therapy, patient's clinical history, and so on, all at the discretion of the treating physician. The agent or antibody can be administered one time or over a series of treatments lasting from several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody. The administering physician can easily determine optimum dosages, dosing methodologies and repetition rates. In general, dosage is from 0.01 μg to 100 mg per kg of body weight, and can be given once or more daily, weekly, monthly or yearly. The treating physician can estimate repetition rates for dosing based on measured residence times and concentrations of the drug in bodily fluids or tissues.

The present invention provides kits comprising the antibodies described herein and that can be used to perform the methods described herein. In certain embodiments, a kit comprises at least one purified antibody against a cancer stem cell marker in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies of the present invention can be readily incorporated into one of the established kit formats which are well known in the art.

Embodiments of the present disclosure can be further defined by reference to the following examples, which describe in detail preparation of antibodies of the present disclosure and methods for using antibodies of the present disclosure. It will be apparent to those skilled in the art that many modifications, both to materials and methods, may be practiced without departing from the scope of the present disclosure. Wherever possible, the same reference numbers will be used throughout the drawings to refer to the same or like parts. As used herein and in the appended claims, the singular forms "a", "or", and "the" include plural referents unless the context clearly dictates otherwise. Thus, for example, reference to "an antibody" includes a plurality of such antibodies or one or more antibodies and equivalents thereof known to those skilled in the art. Furthermore, all numbers expressing quantities of ingredients, reaction conditions, purity, polypeptide and polynucleotide lengths, and so forth, used in the specification, are modified by the term "about", unless otherwise indicated. Accordingly, the numerical parameters set forth in the specification and claims are approximations that may vary depending upon the desired properties of the present invention.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

EXAMPLES

Example 1

Production of DDR1 Antibodies

Antigen Production

A recombinant polypeptide fragment of the extracellular domain of human DDR1 is generated as an antigen for antibody production. Standard recombinant DNA technology is used to isolate a polynucleotide encoding amino acids 1-417 of DDR1 (for example, nucleotide SEQ ID NO:4; amino acid SEQ ID NO:1). This polynucleotide is ligated in-frame N-terminal to either a human Fc-tag or histidine-tag and cloned into a transfer plasmid vector for baculovirus mediated expression in insect cells. Standard transfection, infection, and cell culture protocols are used to produce recombinant insect cells expressing the corresponding DDR1 polypeptide (O'Reilly et al., Baculovirus expression vectors: A Laboratory Manual, Oxford: Oxford University Press (1994)).

Cleavage of the endogenous signal sequence of human DDR1 is approximated using cleavage prediction software SignalP 3.0, however the actual in vivo cleavage point can differ by a couple of amino acids either direction. The predicated cleavage of DDR1 is between amino acids 1 and 20, thus DDR1 antigen protein comprises approximately amino acid 21 through amino acid 417. Antigen protein is purified from insect cell conditioned medium using Protein A and $Ni^{++}$-chelate affinity chromatography. Purified antigen protein is then dialyzed against PBS (pH=7), concentrated to approximately 1 mg/ml, and sterile filtered in preparation for immunization.

Immunization

Mice are immunized with purified DDR1 antigen protein using standard techniques. Blood from individual mice is screened approximately 70 days after initial immunization for antigen recognition using FACS analysis (described below). The animal with the highest antibody titer is selected for final antigen boost after which spleen cells are isolated for hybridoma production. Hybridoma cells are plated at 1 cell per well in 96 well plates, and the supernatant from each well screened by FACS analysis against antigen protein. Hybridomas with high antibody titer are selected and scaled up in static flask culture. Antibodies are purified from the hybridoma supernatant using protein A or protein G agarose chromatography. Purified monoclonal antibodies are again tested by FACS and are isotyped to select for IgG antibodies.

FACS Analysis

To select monoclonal antibodies produced by hybridoma clones that recognize native cell-surface DDR1 protein, FACs analysis can be used. HEK293 cells are co-transfected with expression vectors encoding a full-length cDNA clone of DDR1 and the transfection marker GFP. Twenty-four to forty-eight hours post-transfection, cells are collected in suspension and incubated on ice with anti-DDR1 antibodies or control IgG to detect background antibody binding. The cells are washed and primary antibodies detected with anti-mouse secondary antibodies conjugated to a fluorescent chromophore. Labeled cells are then sorted by FACS to identify anti-DDR1 antibodies that specifically recognize cell surface expression of native cell-surface DDR1 protein.

Epitope Mapping

To identify antibodies that recognize specific regions of the DDR1 extracellular domain, epitope mapping can be performed. Mammalian expression plasmid vectors comprising a CMV promoter upstream of polynucleotides encoding a series of deletion fragments of the extracellular domain of DDR1 fused to Fc protein can be generated using standard recombinant DNA technology. These recombinant fusion proteins can be expressed in transiently transfected HEK 293 cells from which conditioned medium is collected twenty-four to forty-eight hours post-transfection for ELISA. The Fc fusion proteins in the conditioned media are bound to an ELISA plate coated with anti-human Fc (gamma chain specific), which are then incubated with a DDR1 antibody or a control monoclonal antibody. After washing, the bound antibodies are probed with HRP conjugated anti-mouse antibody. To verify equivalent binding of the various DDR1 Fc fusion proteins, the ELISA plate are also probed with HRP conjugated anti-human Fc antibodies. Bound HRP concentrations are determined at $A_{450}$ nm using an ELISA substrate.

The SPOTs system (Sigma Genosys, The Woodlands, Tex.) can also be used to identify specific epitopes within the extracellular domains recognized by an antibody against DDR1. In this method, a series of 10-residue linear peptides overlapping by one amino acid and covering the entire DDR1 extracellular domain are synthesized and covalently bound to a cellulose membrane by the SPOT synthesis technique. The membrane is pre-incubated for 8 hours at room temperature with blocking buffer and hybridized with antibody overnight at 4° C. The membrane is then washed, incubated with a secondary antibody conjugated to horseradish peroxidase (HRP) (GE Healthcare Life Sciences/Amersham Bioscience, Piscataway, N.J.), re-washed, and visualized with signal development solution containing 3-amino-9-ethylcarbazole. Specific epitopes recognized by an antibody are thus determined.

Chimeric Antibodies

After monoclonal antibodies that specifically recognize human DDR1 are identified, these antibodies can be modified to overcome the human anti-mouse antibody (HAMA) immune response when rodent antibodies are used as therapeutic agents. The variable regions of the heavy-chain and light-chain of the selected monoclonal antibody are isolated by RT-PCR from hybridoma cells and ligated in-frame to human $IgG_1$ heavy-chain and kappa light chain constant regions, respectively, in mammalian expression vectors. Alternatively a human Ig expression vector such as TCAE 5.3 is used that contains the human $IgG_1$ heavy-chain and kappa light-chain constant region genes on the same plasmid (Preston et al., 1998, *Infection & Immunity* 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against DDR1 can undergo further humanization. To generate humanized antibodies, key aspects of the specificity determining motifs of the antibody, potentially including elements from both the three short hypervariable sequences, or complementary determining regions (CDRs), and/or the framework regions required to correctly position the CDR regions of the antibody heavy- and light-chain variable domains described above are engineered using recombinant DNA technology into the germline DNA sequences of human heavy- and light-chain antibody genes, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Human Antibodies

In some embodiments, human antibodies that specifically recognize the extracellular domain of DDR1 can be isolated using phage display technology. A phage display antibody library containing human antibody variable domains displayed as single chain Fv or as Fab domains is screened for specific and high affinity recognition of the DDR1 antigen described above or, for example, the DDR1-Fc fusion of SEQ ID NO:8. The identified variable domain antibody sequences are then reformatted into an Ig expression vector containing human $IgG_1$ heavy-chain and kappa light-chain for expression of human antibodies in CHO cells.

Example 2

In Vitro Cytotoxicity Assays to Evaluate Antibodies Against DDR1

This example describes representative in vitro assays to test the activity of antibodies generated against DDR1 on cytotoxicity.

Complement-Dependent Cytotoxicity Assay

In certain embodiments, cancer cell lines expressing DDR1 or cancer stem cells isolated from a patient sample passaged as a xenograft in immunocompromised mice (described in detail below) can be used to measure complement-dependent cytotoxicity (CDC) mediated by an antibody against DDR1. Cells ($10^6$ cells/ml) are suspended in 200 μl RPMI 1640 culture medium supplemented with antibiotics and 5% FBS. Suspended cells are mixed with antibodies against DDR1 or control antibodies in triplicate and incubated for 1 to 4 hours at 37° C. in 5% $CO_2$. Treated cells are then collected, resuspended in 100 μl FITC-labeled annexin V diluted in culture medium, and incubated at room temperature for 10 minutes. One hundred microliters of propidium iodide solution (25 μg/ml) diluted in HBSS is added and incubated for 5 minutes at room temperature. Cells are collected, resuspended in culture medium, and analyzed by flow cytometry. Flow cytometry of FITC stained cells provides total cell counts, and propidium iodide uptake by dead cells as a percentage of total cell numbers is used to measure cell death in the presence of antibodies against DDR1 compared to control antibodies. The ability of anti-DDR1 antibodies to mediate complement-dependent cytotoxicity is thus determined.

Antibody-Dependent Cellular Cytotoxicity Assay

In certain embodiments, cancer cell lines expressing DDR1 or cancer stem cells isolated from a patient's sample passaged as a xenograft in immunocompromised mice (described in detail below) can be used to measure antibody-dependent cellular cytotoxicity (ADCC) mediated by an antibody against DDR1. Cells ($10^6$ cells/ml) are suspended in 200 μl phenol red-free RPMI 1640 culture medium supplemented with antibiotics and 5% FBS. Peripheral blood mononuclear cells (PBMCs) are isolated from heparinized peripheral blood by Ficoll-Paque™ density gradient centrifugation for use as effector cells. Target cells (T) are then mixed with PBMCeffector cells (E) at E/T ratios of 25:1, 10:1, and 5:1 in 96-well plates in the presence of DDR1 antibody or a control antibody. Controls include incubation of target cells alone and effector cells alone in the presence of antibody. Cell mixtures are incubated for 1 to 6 hours at 37° C. in 5% $CO_2$. Released lactate dehydrogenase (LDH), a stable cytosolic enzyme released upon cell lysis, is then measured by a colorimetric assay (CytoTox96 Non-radioactive Cytotoxicity Assay; Promega; Madison, Wis.). Absorbance data at 490 nm are collected with a standard 96-well plate reader and background corrected. The percentage of specific cytotoxicity is calculated according to the formula: % cytotoxicity=100×(experimental LDH release−effector spontaneous LDH release−target spontaneous LDH release)/(target maximal LDH release−target spontaneous LDH release). The ability of antibodies against DDR1 receptor to mediated antibody-dependent cellular cytotoxicity is thus determined.

Example 3

In Vivo Prevention of Tumor Growth Using Anti-DDR1 Antibodies

This example describes the use of anti-DDR1 antibodies to prevent tumor growth in a xenograft model. Tumor cells from a patient sample (solid tumor biopsy or pleural effusion) that have been passaged as a xenograft in mice are prepared for repassaging into experimental animals. Tumor tissue is removed under sterile conditions, cut up into small pieces, minced completely using sterile blades, and single cell suspensions are obtained by enzymatic digestion and mechanical disruption. Specifically, pleural effusion cells or the resulting tumor pieces are mixed with ultra-pure collagenase III in culture medium (200-250 units of collagenase per mL) and incubated at 37° C. for 3-4 hours with pipetting up and down through a 10-mL pipette every 15-20 minutes. Digested cells are filtered through a 45 μM nylon mesh, washed with RPMI/20% FBS, and washed twice with HBSS. Dissociated tumor cells are then injected subcutaneously either into the mammary fat pads, for breast tumors, or into the flank, for non-breast tumors, of NOD/SCID mice to elicit tumor growth.

In certain in vivo experiments, dissociated tumor cells are first sorted into tumorigenic and non-tumorigenic cells based on cell surface markers before injection into experimental animals. Specifically, tumor cells dissociated as described above are washed twice with HEPES-buffered saline solution (HBSS) containing 2% heat-inactivated calf serum (HICS) and resuspended at $10^6$ cells per 100 μl. Antibodies are added and the cells incubated for 20 minutes on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin;

PharMingen, San Jose, Calif.). Antibodies are directly conjugated to fluorochromes to positively or negatively select cells expressing these markers. Mouse cells are eliminated by selecting against H2Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin-tumorigenic cells are then injected subcutaneously into NOD/SCID mice to elicit tumor growth.

In one, non-limiting example of an in vivo experiment, anti-DDR1 antibodies are analyzed for their ability to reduce the growth of PE13 breast tumor cells. Dissociated PE13 cells comprising both tumorigenic and non-tumorigenic tumor cells (10,000 per animal) are injected subcutaneously into the mammary fat pads or the flank region of 6-8 week old NOD/SCID mice. Two days after tumor cell injection, animals are injected intraperitoneal (i.p.) with 10 mg/kg anti-DDR1 antibodies two times per week. Tumor growth is monitored weekly until growth is detected, after which point tumor growth is measured twice weekly.

In another example, anti-DDR1 antibodies are also analyzed for their ability to reduce the growth of C9 colon tumor cells. Dissociated C9 cells comprising both tumorigenic and non-tumorigenic tumor cells (10,000 per animal) are injected subcutaneously into the flank region of 6-8 week old NOD/SCID mice. Two days after tumor cell injection, animals are injected intraperitoneal (i.p.) with 10 mg/kg anti-DDR1 antibodies two times per week. Tumor growth is monitored weekly until growth is detected, after which point tumor growth is measured twice weekly.

Example 4

In Vivo Prevention of Tumor Growth Using Anti-DDR1 Antibodies in Combination Therapy This example describes the use of anti-DDR1 antibodies to prevent tumor growth in a xenograft model in combination with chemotherapy. Tumor cells from a patient solid tumor biopsy passaged as a xenograft in mice are prepared for repassaging into experimental animals as described in detail above.

In certain embodiments, anti-DDR1 antibodies are analyzed for their ability to affect breast tumor recurrence after combination therapy with a chemotherapeutic agent. Dissociated PE13 cells (10,000 per animal) are injected subcutaneously into the mammary fat pads or the flank region of 6-8 week old NOD/SCID mice and animals are monitored for tumor growth. Once tumors reach an average size of approximately 100 mm$^3$, treatment begins: animals are treated i.p. with 10 mg/kg of anti-DDR1 antibodies or control antibodies in combination with 15 mg/kg taxol administered two times per week for a total of four weeks. Tumor growth is monitored weekly as tumor volume decreases in response to the combination therapy. After four weeks, taxol administration may be ceased while antibody treatment is maintained.

Example 5

In Vivo Treatment of Tumors Using Anti-DDR1 Antibodies

This example describes the use of anti-DDR1 antibodies to treat cancer in a xenograft model. In certain embodiments, tumor cells from a patient sample (solid tumor biopsy or pleural effusion) that have been passaged as a xenograft in mice can be prepared for repassaging into experimental animals. Tumor tissue is removed, cut up into small pieces, minced completely using sterile blades, and single cell suspensions obtained by enzymatic digestion and mechanical disruption. Dissociated tumor cells comprising both tumorigenic and non-tumorigenic tumor cells are then injected subcutaneously either into the mammary fat pads, for breast tumors, or into the flank, for non-breast tumors, of NOD/SCID mice to elicit tumor growth. Alternatively, ESA+, CD44+, CD24−/low, Lin-tumorigenic tumor cells are isolated as described in detail above and injected.

Following tumor cell injection, animals are monitored for tumor growth. Once tumors reach an average size of approximately 150 to 200 mm$^3$, antibody treatment begins. Each animal receives 100 μg of DDR1 antibodies or control antibodies i.p. two to five times per week for a total of 6 weeks. Tumor size is assessed twice a week during these 6 weeks. The ability of DDR1 antibodies to prevent further tumor growth or to reduce tumor size compared to control antibodies is thus determined.

At the end point of antibody treatment, tumors are harvested for further analysis. In some embodiments a portion of the tumor is analyzed by immunofluorescence to assess antibody penetration into the tumor and tumor response. A portion of each harvested tumor from anti-DDR1 treated and control antibody treated mice is flash-frozen in liquid nitrogen, embedded in O.C.T., and cut on a cryostat as 10 μm sections onto glass slides. In some embodiments, a portion of each tumor is formalin-fixed, paraffin-embedded, and cut on a microtome as 10 plm section onto glass slides. Sections are post-fixed and incubated with chromophore-labeled antibodies that specifically recognize injected antibodies to detect anti-DDR1 or control antibodies present in the tumor biopsy. Furthermore antibodies that detect different tumor and tumor-recruited cell types such as, for example, anti-VE cadherin (CD144) or anti-PECAM-1 (CD31) antibodies to detect vascular endothelial cells, anti-smooth muscle alpha-actin antibodies to detect vascular smooth muscle cells, anti-Ki67 antibodies to detect proliferating cells, TUNEL assays (Negoescu et al., 1996, E. J. *Histochem Cytochem.* 44(9):959-68; Negoescu et al., 1998*, Biomed Pharmacother.* 52(6):252-8) to detect dying cells, anti-β-catenin antibodies to detect Wnt signaling, and anti-intracellular domain (ICD) Notch fragment antibodies to detect Notch signaling can be used to assess the effects of antibody treatment on, for example, angiogenesis, tumor growth, and tumor morphology.

In certain embodiments, the effect of anti-DDR1 antibody treatment on tumor cell gene expression is also assessed. Total RNA is extracted from a portion of each harvested tumor from DDR1 antibody treated and control antibody treated mice and used for quantitative RT-PCR. Expression levels of DDR1 as well as additional cancer stem cell markers previously identified (e.g., CD44) are analyzed relative to the house-keeping gene GAPDH as an internal control. Changes in tumor cell gene expression upon DDR1 antibody treatment are thus determined.

In addition, the effect of anti-DDR1 antibody treatment on the presence of cancer stem cells in a tumor is assessed. Tumor samples from DDR1 antibody treated versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin-surface cell marker expression as described in detail above.

The tumorigenicity of cells isolated based on ESA+, CD44+, CD24−/low, Lin-expression following anti-DDR1 antibody treatment can then be assessed. ESA+, CD44+, CD24−/low, Lin-cancer stem cells isolated from DDR1 antibody treated versus control antibody treated mice are re-injected subcutaneously into the mammary fat pads or flank regions of NOD/SCID mice. The tumorigenicity of cancer stem cells based on the number of injected cells required for consistent tumor formation is then determined.

Example 6

Prevention of Metastasis with Anti-DDR1 Antibodies

This example describes methods of treating metastasis using antibodies against DDR1. The role of DDR1 in regulation of the extracellular matrix is well-established and suggests that antibodies directed against DDR1 may inhibit invasion and metastasis of tumor cells. Primary tumor cells or cells from a primary tumor cell line can be transplanted into NOD/SCID mice as described, for example, in Wang et al., 2005, *Lab. Investigation* 85: 1395-1404. In certain embodiments, antibody treatment commences following detection of tumor growth of transplanted cells within the original transplant site. Injection of 10 mg/kg anti-DDR1 antibodies intraperitoneal (i.p.) two times per week continues for up to 54 weeks. The spread of tumor cells to organ systems beyond the original transplant site is monitored compared to PBS injected control animals.

Example 7

Treatment of Human Cancer Using Anti-DDR1 Antibodies

This example describes methods for treating cancer using antibodies against DDR1 to target tumors comprising cancer stem cells and/or other tumor cells in which DDR1 expression has been detected. The presence of cancer stem cell marker expression can first be determined from a tumor biopsy. Tumor cells from a biopsy from a patient diagnosed with cancer are removed under sterile conditions. In some embodiments the tissue biopsy is flash-frozen in liquid nitrogen, embedded in O.C.T., and cut on a cryostat as 10 μm sections onto glass slides. In some embodiments, the tissue biopsy is formalin-fixed, paraffin-embedded, and cut on a microtome as 10 μm section onto glass slides. Sections are incubated with antibodies against DDR1 to detect protein expression.

The presence of cancer stem cells can also be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -DDR1 antibodies to detect cancer stem cells, and the presence of ESA+, CD44+, CD24−/low, Lin-, DDR1+ tumor stem cells is determined by flow cytometry as described in detail above.

In certain embodiments, cancer patients whose tumors are diagnosed as expressing DDR1 are treated with anti-DDR1 antibodies. In certain embodiments, humanized or human monoclonal anti-DDR1 antibodies generated as described above are purified and formulated with a suitable pharmaceutical vehicle for injection. In some embodiments, patients are treated with the DDR1 antibodies at least once a month for at least 10 weeks. In some embodiments, patients are treated with the DDR1 antibodies at least once a week for at least about 14 weeks. Each administration of the antibody should be a pharmaceutically effective dose. In some embodiments, between about 2 to about 100 mg/ml of an anti-DDR1 antibody is administered. In some embodiments, between about 5 to about 40 mg/ml of an anti-DDR1 antibody is administered. The antibody can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis Example 8

Cell-Based Assay for Identification of Anti-DDR1 Antibodies with Agonist or Antagonist Properties This example describes exemplary cell-based assays for identification of DDR1 antibodies with agonist or antagonist properties.

K562 cells are transfected with pcDNA3.1 FLAG-DDR1 using standard procedures. Stable lines expressing FLAG tagged DDR1 are selected with neomycin and one stable line expressing FLAG-DDR1 (SEQ ID NO:37) is selected for analyzing collagen-induced phosphorylation.

Cells are starved in serum-free medium for 36 hours. Cells are then treated with collagen to stimulate phosphorylation of DDR1. To test the antagonist properties of anti-DDR1 antibodies, cells are pretreated with 5 or 50 μg/ml of the indicated antibodies, subsequently stimulated with rat tail collagen I at a final concentration of 10 μg/ml and tyrosine phosphorylation of DDR1 is assessed. To evaluate the agonist properties of the antibodies, cells are incubated with the antibodies in the absence of collagen and tyrosine phosphorylation of DDR1 is assessed. At the indicated time intervals after treatments, cells are lysed in sample buffer. Proteins are separated by SDS-polyacrylamide gel electrophoresis (PAGE) and are transferred to a nitrocellulose membrane. Membranes are blocked in TBS-T (Tris-Buffered Saline plus 0.1% Tween 20) containing 5% nonfat milk. Antibodies (anti-phosphotyrosine, 4G10 clone; and anti-Flag epitope, M2 clone) are incubated for 1 h at room temperature in PBS-T with 0.5% milk. Bound primary antibodies are detected with appropriate secondary antibodies conjugated with HRP and ECL plus.

K562 cells expressing FLAG tagged DDR1 are treated for 4 hours with candidate antibodies to DDR1 in the absence of exogenous collagen. Treatment with antibodies that increase tyrosine phosphorylation of DDR1 indicates that the antibodies have agonist properties. Stimulation of the cells with collagen type I causes an increase in tyrosine phosphorylation of DDR1. An ability of an antibody to block the stimulation of DDR1 on the K562 cells in response to collagen indicates that the antibody being tested is an antagonist of DDR1. The assay is not limited to any one particular tumor cell line or type (for example, K562 cells as described above), as would be known to those skilled in the art.

Example 9

Detection of DDR1 Protein Expression by Tumors

The expression of DDR1 in a variety of tumor cell lines has been reported previously. Therefore, the expression of DDR1 on primary human tumor derived xenograft models was analyzed.

OMP-C27 (colon tumor) and OMP-Lu4 (lung tumor) xenograft tumors were embedded in OCT compound and frozen. 5 μm cryosections were incubated with blocking solution (PBS with 5% horse serum), followed by incubation with polyclonal mouse anti-DDR1 serum diluted 1:200 in blocking solution. After multiple wash steps, murine polyclonal anti-DDR1 antibodies were detected with Alexa 594 goat anti-mouse antibodies.

Using murine polyclonal antibodies to human DDR1, DDR1 protein was detected on the cell surface of human tumor cells. Specifically example images of cryosections of a colon tumor model (OMP-C27) and a lung tumor model (OMP-Lu4) are shown, wherein DDR1 protein could be detected (FIG. 1), whereas control antibody did not stain tumor cells in both OMP-C27 and OMP-Lu4 tumors.

Example 10

Correlation of DDR1 Expression with LGR5 Expression

To study the potential function of DDR1 in stem cells, we compared the expression pattern of DDR1 to LGR5, a known stem cell marker in colon and intestine, using standard Pearson correlation. Within a large set of expression data from normal/malignant samples, we performed correlation analysis of expression values between DDR1 and LGR5 in colon/intestine (446), breast (163), kidney (153), liver (107), lung (217), ovary (145), pancreas (85) and prostate (128) samples. The results of the expression correlation study are shown below in Table 2. The expression patterns of DDR1 and LGR5 showed statistically significant positive correlation in the colon, liver, ovary and pancreas samples (in bold).

TABLE 2

Correlation of DDR1 expression with LGR5 expression across normal and cancer samples

| Colon | Breast | Kidney | Liver | Lung | Ovary | Prostate | Pancreas |
|---|---|---|---|---|---|---|---|
| **0.541*** | 0.0101 | 0.131 | **0.496** | 0.124 | **0.410** | −0.299 | **0.330** |
| p < 0.0001 | p = 0.90 | p = 0.11 | p < 0.0001 | p = 0.07 | p < 0.0001 | p < 0.001 | p < 0.004 |

*Correlation value >0 signifies positive correlation

Example 11

Correlation of DDR1 Expression with Activation of Notch Signaling

To study the potential function of DDR1 in stem cells, we compared the expression pattern of DDR1 to Hes1 expression, a marker of Notch pathway activation, using standard Pearson correlation. Within a large set of expression data from normal/malignant samples, we performed correlation analysis of expression values between DDR1 and Hes1 in colon/intestine (446), breast (163), kidney (153), liver (107), lung (217), ovary (145), pancreas (85) and prostate (128) samples. The results of the expression correlation study are shown below in Table 3. The expression patterns of DDR1 and Hes1 showed statistically significant positive correlation in the colon, breast, renal, lung, prostate, and pancreas samples (in bold).

TABLE 3

Correlation of DDR1 expression with Hes1 expression across normal and cancer samples

| Colon | Breast | Kidney | Liver | Lung | Ovary | Prostate | Pancreas |
|---|---|---|---|---|---|---|---|
| **0.722*** | **0.626** | **0.581** | 0.120 | **0.430** | 0.003 | **0.625** | **0.622** |
| p < 0.0001 | p < 0.0001 | p < 0.0001 | p = 0.22 | p < 0.0001 | p = 0.97 | p < 0.0001 | p < 0.0001 |

*Correlation value >0 signifies positive correlation

Example 12

Limiting Dilution Assays to Assess the Reduction of the Number of Cancer Stem Cells Limiting dilution assays (LDA) can be used to assess the effect of a DDR1-modulating agent or antibody on solid tumor cancer stem cells and on the tumorigenicity of a tumor comprising the cancer stem cells. The assays can be used to determine the frequency of cancer stem cells in tumors from animals treated with the DDR1-modulating antibody or other agent and to compare that frequency to the frequency of cancer stem cells in tumors from control animals.

For instance, in one non-limiting example of a limiting dilution assay, C17 colon tumors from mice that have been treated with either control or a candidate anti-DDR1 antibody at 10 mg/kg twice per week are isolated after 38 days of treatment. Isolated tumors are dissociated and FACS analyzed to determine the ratio of mouse to human cells. Human cells in increasingly lower numbers are then re-injected into immunocompromised mice. For example, mice may be injected with 1000, 333, 111, or 37 isolated human tumor cells (comprising both tumorigenic and non-tumorigenic tumor cells) in the right flank region. Tumor volume is assessed twice per week. At the desired time point (e.g., day 28, 34, or 42) the percentage of mice with detectable tumors is determined in all groups injected with anti-DDR1 antibody treated tumor cells and compared to the percentage of mice with detectable tumors in the controls. For example, the number of mice injected with 1000 control-treated tumor cells that have detectable tumors is determined and compared to the number of mice injected with 1000 DDR1-antibody treated tumor cells that have detectable tumors.

The stem cell frequency can be calculated using L-Calc™ software (downloadable from www. followed by stemcell.com/search/default.asp). Briefly, based on Poisson statistics, exactly one stem cell exists among the known number of injected cells if 37% of the animals fail to develop tumors.

Example 13

Production of Monoclonal DDR1 Antibodies

A recombinant polypeptide fragment of the extracellular domain of human DDR1 was generated as an antigen for antibody production as described herein. Briefly, standard recombinant DNA technology was used to isolate a polynucleotide encoding amino acids 1-417 of DDR1 (nucleotide SEQ ID NO:4; amino acid SEQ ID NO: 1). The polynucleotide was ligated in-frame N-terminal to either a human Fc-tag or histidine-tag and cloned into a transfer plasmid vector for baculovirus-mediated expression in insect cells. Standard transfection, infection, and cell culture protocols were used to produce recombinant insect cells expressing the corresponding DDR1 polypeptide (O'Reilly et al., 1994, Baculovirus expression vectors: A Laboratory Manual. Oxford: Oxford University Press).

DDR1 protein was purified from insect cell conditioned medium using Protein A and Ni++-chelate affinity chromatography as known to one skilled in the art. Purified DDR1 protein was dialyzed against PBS (pH=7), concentrated to approximately 1 mg/ml, and sterile filtered in preparation for immunization.

Mice (n=3) were immunized with purified DDR1 protein using standard techniques known to one skilled in the art. Blood from individual mice was screened approximately 70 days after initial immunization for antigen recognition using FACS analysis (as described herein). The animal with the highest antibody titer was selected for final antigen boost after which spleen cells were isolated for hybridoma production. Hybridoma cells were plated at 1 cell per well in 96 well plates, and the supernatant from each well screened by FACS analysis against antigen protein. Several hybridomas with high antibody titer were selected and scaled up in static flask culture. Antibodies were purified from the hybridoma supernatant using protein A or protein G agarose chromatography. Purified monoclonal antibodies were again tested by FACS and were isotyped to select for IgG antibodies.

To select monoclonal antibodies produced by hybridoma clones that recognize native cell-surface DDR1 protein, FACS analysis was used. HEK293 cells were co-transfected with expression vectors encoding a full-length cDNA clone of DDR1 and the transfection marker GFP. Twenty-four to forty-eight hours post-transfection, cells were collected in suspension and incubated on ice with anti-DDR1 antibodies or control IgG1 to detect background antibody binding. The cells were washed and primary antibodies bound to the DDR1-expressing cells were detected with anti-mouse secondary antibodies conjugated to a fluorescent chromophore. Labeled cells were then sorted by FACS to identify anti-DDR1 antibodies that specifically recognize cell surface expression of native cell-surface DDR1 protein. Two monoclonal antibodies that recognize and bind to DDR1 were identified, antibodies 20M102 and 20M104 (FIG. 2). A hybridoma expressing antibody 20M102, was deposited with American Type Culture Collection (ATCC), 10801 University Blvd., Manassas, Va., USA, under the conditions of the Budapest Treaty on May 21, 2009, and assigned deposit number PTA-10051.

Example 14

DDR1 Variants for Screening of Antibodies

DDR1 variants containing point mutations in the extracellular domain were produced by methods known to one of skill in the art. For example, site-directed mutagenesis of DDR2 has been done to study collagen binding sites (Ichikawa et al., 2007, *EMBO J.* 26:4168-4176). Briefly, site-directed mutagenesis was performed following the Stratagene QuikChange protocol and using pcDNA DDR1-FLAG as the wild-type template plasmid DNA. Specifically, the following mutations were generated in the extracellular domain of DDR1: W53A, D68A, R105A, L110A, E113Q, and S175A (using numbering based upon SEQ ID NO:2).

Full length cDNA encoding FLAG-tagged human DDR1 variants were transiently transfected into HEK293 cells using standard procedures as known to one skilled in the art. To determine the capacity of antibodies to bind the DDR1 variants, antibodies were incubated with HEK293 cells transfected with plasmid encoding either wild type DDR1 or one of the point mutation variants. All cells were co-transfected with plasmid encoding GFP. The cells were analyzed by FACS as described herein for binding of the antibodies to wild type DDR1 and to DDR1 variants.

As shown in FIG. 3A, antibodies 20M102 and 20M104 did not bind, or bound at substantially reduced levels, to the W53A DDR1 variant as compared to wild-type DDR1. There was no apparent reduction in binding to any of the other DDR1 mutants (FIGS. 3A and 3B). The data demonstrated that the tryptophan (W) residue at position 53 is important for binding of antibodies 20M102 and 20M104 to DDR1.

Example 15

Analysis of Anti-DDR1 Antibodies for Agonist or Antagonist Properties

Full length cDNA encoding FLAG-tagged human DDR1 (nucleotide SEQ ID NO:36; amino acid SEQ ID NO:37) in pcDNA3.1 vector was transfected into HEK293 cells using standard procedures as known to one skilled in the art. 48 hours after transfection neomycin was added to the culture medium at a concentration of 2 mg/ml. After 10 days under selection conditions, single cell clones were expanded and assessed for cell surface expression of DDR1 by FACS as described herein. Clones expressing FLAG-tagged DDR1 were identified and expanded for use in assays.

HEK293-DDR1 expressing cells were plated in 12 well plates, grown for 48 hours in DMEM with 10%/o serum, then serum starved for 36 hours. Cells were pre-incubated with anti-DDR1 antibodies at concentrations of 1, 5 and 50 μg/ml for 15 min, and subsequently incubated in the presence or absence of rat tail collagen type 1 (30 μg/ml) for 3 hours.

Western blot analysis was used to evaluate the tyrosine phosphorylation status of DDR1 after treatment. Cells were lysed in 1 ml of ice-cold lysis buffer (20 mM Tris-Cl pH7.5, 150 mM NaCl, 1 mM EDTA, 1 mM EGTA, 1% Triton, 2.5 mM sodium pyrophosphate, 1 mM beta-glycerophosphate, 1 mM sodium orthovanadate, 1 μg/ml leupeptin). Lysates were centrifuged for 5 min at 20,000 g to clear cellular debris from the supernatant. For immunoprecipitations, 20 μl of agarose beads conjugated to anti-FLAG M2 antibody were mixed with supernatants and incubated for 2 hours on a rotator. The agarose beads were washed twice with lysis buffer, followed by resuspension in denaturing sample buffer. Proteins were separated by SDS-polyacrylamide gel electrophoresis (SDS-PAGE) and transferred to nitrocelluose membranes. Membranes were blocked in TBS-T (Tris-Buffered Saline plus 0.1% Tween 20) containing 5% nonfat milk for approximately 1 hour. The membranes were washed, and then incubated with primary antibodies (anti-phosphotyrosine, 4G10 clone, and anti-FLAG epitope, M2 clone) for 1 hour at room temperature in PBS-T with 0.5% milk. Bound primary antibodies were detected with appropriate secondary antibodies conjugated with HRP and visualized using an ECL Plus Western Blotting Detection System (GE Healthcare Life Sciences/Amersham Bioscience, Piscataway, N.J.).

It is known that DDR1-expressing cells respond to treatment with collagen by increased phosphorylation of DDR1 on tyrosine residues. As shown in FIG. 4, the addition of antibody 20M102 in the presence of collagen inhibited the phosphorylation of DDR1 in a dose-dependent manner (see lanes 7-9). In contrast, the addition of 20M104 in the presence of collagen did not block the phosphorylation of DDR1 (see lanes 13-15). Detection of total DDR1 protein with anti-FLAG antibody revealed equivalent amounts of DDR1 protein among various treatment conditions. The data demonstrated that 20M102 acted as an antagonist of collagen-induced phosphorylation of DDR1 in HEK293 cells. Finally, the addition of antibodies 20M102 or 20M104 in the absence of collagen did not alter the phosphorylation of DDR1 demonstrating that neither antibody displayed agonist properties in the HEK293 cells (see lanes 4-6, 20M102 and lanes 10-12, 20M104). The antagonist/agonist properties of antibodies 20M102 and 20M104 may be cell type dependent. For example, 20M102 demonstrated different properties in a phosphorylation assay in a different cell line.

Example 16

Detection of DDR1 Protein Expression in OMP-C37 Tumor Cells

Immunoflouroscence staining was performed on sections of tumor samples. Colon tumor OMP-C37 xenografts were embedded in OCT compound and frozen. 5 μm cryosections were incubated with blocking solution (PBS with 2% bovine serum albumin). The cryosections were then incubated with primary anti-DDR1 antibody 20M102 or an anti-trinitrophenol (hapten) antibody as control antibody. Both antibodies were diluted in PBS with 2% bovine serum albumin to a concentration of 5 μg/ml. After multiple wash steps, bound antibodies were detected with Alexa 594-labeled goat anti-mouse secondary antibody. Nuclei were stained with DAPI by standard methods.

FIG. 5 shows representative images of cryosections of colon tumor OMP-C37, demonstrating that the DDR1 protein was detected with 20M102 antibody. Immunofluorescence (light gray in image) showed the localization of DDR1 protein in the OMP-037 colon tumor (FIG. 5A), while there was no detectable immunofluorescence in the sample stained with control antibody (FIG. 5B). FIGS. 5C and 5D are representative images of nuclear staining of cryosections stained with DAPI.

Example 17

Inhibition of Tumor Growth in vivo by 20M102 Antibody

Anti-DDR1 antibodies were analyzed in combination with chemotherapy for the ability to reduce growth of OMP-C37 colon tumor cells in vivo. Dissociated human OMP-C37 cells (10,000 per animal) were injected subcutaneously into the right flank region of 6-8 week old NOD/SCID mice. Tumor growth was monitored and tumor measurements were initiated once tumors were palpable. 46 days after cell injection, tumors were measured to be an average volume of 139 $mm^3$, and treatments were commenced. Animals were treated with anti-DDR1 20M102 antibody with or without concurrent treatment with chemotherapy agent irinotecan. Groups of 10 animals each were injected intraperitoneally (i.p.) with 10 mg/kg 20M102 antibody or control antibody two times per week for the duration of the experiment. Animals receiving combination therapy were administered irinotecan one time per week (15 mg/kg in saline). Tumor growth was monitored weekly for a total of 7 weeks.

NOD/SCID mice with established OMP-C37 tumors were treated with either control antibody, 20M102 antibody, irinotecan, or a combination of 20M102 and irinotecan. As shown in FIG. 6, treatment with 20M102 antibody (squares) alone did not significantly reduce tumor volume as compared to control treated animals (diamonds). However, the combination treatment of 20M102 and irinotecan (circles) reduced the growth of OMP-C37 colon tumors by 44% as compared to irinotecan treatment alone (p=0.01). This experiment showed that anti-DDR1 antibody, 20M102, has anti-tumor growth activity in OMP-037 colon tumor model in combination with the chemotherapeutic agent irinotecan.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All documents, e.g., scientific publications, patents, patent applications and patent publications, recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

Sequences

```
DDR1 immunized fragment amino acid sequence (SEQ ID NO: 1)
MGPEALSSLLLLLLVASGDADMKGHFDPAKCRYALGMQDRTIPDSDISASSSWSDSTAAR

HSRLESSDGDGAWCPAGSVFPKEEEYLQVDLQRLHLVALVGTQGRHAGGLGKEFSRSYRL

RYSRDGRRWMGWKDRWGQEVISGNEDPEGVVLKDLGPPMVARLVRFYPRADRVMSVCLRV

ELYGCLWRDGLLSYTAPVGQTMYLSEAVYLNDSTYDGHTVGGLQYGGLGQLADGVVGLDD

FRKSQELRVWPGYDYVGWSNHSFSSGYVEMEFEFDRLRAFQAMQVHCNNMHTLGARLPGG

VECRFRRGPAMAWEGEPMRHNLGGNLGDPRARAVSVPLGGRVARFLQCRFLFAGPWLLFS

EISFISDVVNNSSPALGGTFPPAPWWPPGPPPTNFSSLELEPRGQQPVAKAEGSPTA

DDR1 transcript A full length amino acid sequence (SEQ ID NO: 2)
MGPEALSSLLLLLLVASGDADMKGHFDPAKCRYALGMQDRTIPDSDISASSSWSDSTAAR

HSRLESSDGDGAWCPAGSVFPKEEEYLQVDLQRLHLVALVGTQGRHAGGLGKEFSRSYRL
```

-continued

RYSRDGRRWMGWKDRWGQEVISGNEDPEGVVLKDLGPPMVARLVRFYPRADRVMSVCLRV

ELYGCLWRDGLLSYTAPVGQTMYLSEAVYLNDSTYDGHTVGGLQYGGLGQLADGVVGLDD

FRKSQELRVWPGYDYVGWSNHSFSSGYVEMEFEFDRLRAFQAMQVHCNNMHTLGARLPGG

VECRFRRGPAMAWEGEPMRHNLGGNLGDPRARAVSVPLGGRVARFLQCRFLFAGPWLLFS

EISFISDVVNNSSPALGGTFPPAPWWPPGPPPTNFSSLELEPRGQQPVAKAEGSPTAILI

GCLVAIILLLLLIIALMLWRLHWRRLLSKAERRVLEEELTVHLSVPGDTILINNRPGPRE

PPPYQEPRPRGNPPHSAPCVPNGSAYSGDYMEPEKPGAPLLPPPPQNSVPHYAEADIVTL

QGVTGGNTYAVPALPPGAVGDGPPRVDFPRSRLRFKEKLGEGQFGEVHLCEVDSPQDLVS

LDFPLNVRKGHPLLVAVKILRPDATKNARNDFLKEVKIMSRLKDPNIIRLLGVCVQDDPL

CMITDYMENGDLNQFLSAHQLEDKAAEGAPGDGQAAQGPTISYPMLLHVAAQIASGMRYL

ATLNFVHRDLATRNCLVGENFTIKIADFGMSRNLYAGDYYRVQGRAVLPIRWMAWECILM

GKFTTASDVWAFGVTLWEVLMLCRAQPFGQLTDEQVIENAGEFFRDQGRQVYLSRPPACP

QGLYELMLRCWSRESEQRPPFSQLHRFLAEDALNTV

Human DDR2 full length amino acid sequence (SEQ ID NO: 3)
MILIPRMLLVLFLLLPILSSAKAQVNPAICRYPLGMSGGQIPDEDITASSQWSESTAAKY

GRLDSEEGDGAWCPEIPVEPDDLKEFLQIDLHTLHFITLVGTQGRHAGGHGIEFAPMYKI

NYSRDGTRWISWRNRHGKQVLDGNSNPYDIFLKDLEPPIVARFVRFIPVTDHSMNVCMRV

ELYGCVWLDGLVSYNAPAGQQFVLPGGSIIYLNDSVYDGAVGYSMTEGLGQLTDGVSGLD

DFTQTHEYHVWPGYDYVGWRNESATNGYIEIMFEFDRIRNFTTMKVHCNNMFAKGVKIFK

EVQCYFRSEASEWEPNAISFPLVLDDVNPSARFVTVPLHHRMASAIKCQYHFADTWMMFS

EITFQSDAAMYNNSEALPTSPMAPTTYDPMLKVDDSNTRILIGCLVAIIFILLAIIVIIL

WRQFWQKMLEKASRRMLDDEMTVSLSLPSDSSMFNNNRSSSPSEQGSNSTYDRIFPLRPD

YQEPSRLIRKLPEFAPGEEESGCSGVVKPVQPSGPEGVPHYAEADIVNLQGVTGGNTYSV

PAVTMDLLSGKDVAVEEFPRKLLTFKEKLGEGQFGEVHLCEVEGMEKFKDKDFALDVSAN

QPVLVAVKMLRADANKNARNDFLKEIKIMSRLKDPNIIHLLSVCITDDPLCMITEYMENG

DLNQFLSRHEPPNSSSSDVRTVSYTNLKFMATQIASGMKYLSSLNFVHRDLATRNCLVGK

NYTIKIADFGMSRNLYSGDYYRIQGRAVLPIRWMSWESILLGKFTTASDVWAFGVTLWET

FTFCQEQPYSQLSDEQVIENTGEFFRDQGRQTYLPQPAICPDSVYKLMLSCWRRDTKNRP

SFQEIHLLLLQQGDE

DDR1 immunized fragment nucleotide sequence (SEQ ID NO: 4)
ATGGGACCAGAGGCCCTGTCATCTTTACTGCTGCTGCTCTTGGTGGCAAGTGGAGATGCT

GACATGAAGGGACATTTTGATCCTGCCAAGTGCCGCTATGCCCTGGGCATGCAGGACCGG

ACCATCCCAGACAGTGACATCTCTGCTTCCAGCTCCTGGTCAGATTCCACTGCCGCCCGC

CACAGCAGGTTGGAGAGCAGTGACGGGGATGGGGCCTGGTGCCCCGCAGGGTCGGTGTTT

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACTGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

-continued

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

GAAATCTCCTTCATCTCTGATGTGGTGAACAATTCCTCTCCGGCACTGGGAGGCACCTTC

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCGG

DDR1 transcript A nucleotide sequence (SEQ ID NO: 5)
ATGGGACCAGAGGCCCTGTCATCTTTACTGCTGCTGCTCTTGGTGGCAAGTGGAGATGCT

GACATGAAGGGACATTTTGATCCTGCCAAGTGCCGCTATGCCCTGGGCATGCAGGACCGG

ACCATCCCAGACAGTGACATCTCTGCTTCCAGCTCCTGGTCAGATTCCACTGCCGCCCGC

CACAGCAGGTTGGAGAGCAGTGACGGGGATGGGGCCTGGTGCCCCGCAGGGTCGGTGTTT

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACTGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

GAAATCTCCTTCATCTCTGATGTGGTGAACAATTCCTCTCCGGCACTGGGAGGCACCTTC

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCATCCTCATC

GGCTGCCTGGTGGCCATCATCCTGCTCCTGCTGCTCATCATTGCCCTCATGCTCTGGCGG

CTGCACTGGCGCAGGCTCCTCAGCAAGGCTGAACGGAGGGTGTTGGAAGAGGAGCTGACG

GTTCACCTCTCTGTCCCTGGGGACACTATCCTCATCAACAACCGCCCAGGTCCTAGAGAG

CCACCCCCGTACCAGGAGCCCCGGCCTCGTGGGAATCCGCCCCACTCCGCTCCCTGTGTC

CCCAATGGCTCTGCCTACAGTGGGGACTATATGGAGCCTGAGAAGCCAGGCGCCCCGCTT

CTGCCCCCACCTCCCCAGAACAGCGTCCCCCATTATGCCGAGGCTGACATTGTTACCCTG

CAGGGCGTCACCGGGGGCAACACCTATGCTGTGCCTGCACTGCCCCCAGGGGCAGTCGGG

GATGGGCCCCCCAGAGTGGATTTCCCTCGATCTCGACTCCGCTTCAAGGAGAAGCTTGGC

GAGGGCCAGTTTGGGGAGGTGCACCTGTGTGAGGTCGACAGCCCTCAAGATCTGGTTAGT

CTTGATTTCCCCCTTAATGTGCGTAAGGGACACCCTTTGCTGGTAGCTGTCAAGATCTTA

-continued

CGGCCAGATGCCACCAAGAATGCCAGGAATGATTTCCTGAAAGAGGTGAAGATCATGTCG

AGGCTCAAGGACCCAAACATCATTCGGCTGCTGGGCGTGTGTGTGCAGGACGACCCCCTC

TGCATGATTACTGACTACATGGAGAACGGCGACCTCAACCAGTTCCTCAGTGCCCACCAG

CTGGAGGACAAGGCAGCCGAGGGGGCCCCTGGGGACGGGCAGGCTGCGCAGGGGCCCACC

ATCAGCTACCCAATGCTGCTGCATGTGGCAGCCCAGATCGCCTCCGGCATGCGCTATCTG

GCCACACTCAACTTTGTACATCGGGACCTGGCCACGCGGAACTGCCTAGTTGGGGAAAAT

TTCACCATCAAAATCGCAGACTTTGGCATGAGCCGGAACCTCTATGCTGGGGACTATTAC

CGTGTGCAGGGCCGGGCAGTGCTGCCCATCCGCTGGATGGCCTGGGAGTGCATCCTCATG

GGGAAGTTCACGACTGCGAGTGACGTGTGGGCCTTTGGTGTGACCCTGTGGGAGGTGCTG

ATGCTCTGTAGGGCCCAGCCCTTTGGGCAGCTCACCGACGAGCAGGTCATCGAGAACGCG

GGGGAGTTCTTCCGGGACCAGGGCCGGCAGGTGTACCTGTCCCGGCCGCCTGCCTGCCCG

CAGGGCCTATATGAGCTGATGCTTCGGTGCTGGAGCCGGGAGTCTGAGCAGCGACCACCC

TTTTCCCAGCTGCATCGGTTCCTGGCAGAGGATGCACTCAACACGGTGTGA

DDR2 full length nucleotide sequence (SEQ ID NO: 6)
ATGATCCTGATTCCCAGAATGCTCTTGGTGCTGTTCCTGCTGCTGCCTATCTTGAGTTCT

GCAAAAGCTCAGGTTAATCCAGCTATATGCCGCTATCCTCTGGGCATGTCAGGAGGCCAG

ATTCCAGATGAGGACATCACAGCTTCCAGTCAGTGGTCAGAGTCCACAGCTGCCAAATAT

GGAAGGCTGGACTCAGAAGAAGGGGATGGAGCCTGGTGCCCTGAGATTCCAGTGGAACCT

GATGACCTGAAGGAGTTTCTGCAGATTGACTTGCACACCCTCCATTTTATCACTCTGGTG

GGGACCCAGGGGCGCCATGCAGGAGGTCATGGCATCGAGTTTGCCCCCATGTACAAGATC

AATTACAGTCGGGATGGCACTCGCTGGATCTCTTGGCGGAACCGTCATGGGAAACAGGTG

CTGGATGGAAATAGTAACCCCTATGACATTTTCCTAAAGGACTTGGAGCCGCCCATTGTA

GCCAGATTTGTCCGGTTCATTCCAGTCACCGACCACTCCATGAATGTGTGTATGAGAGTG

GAGCTTTACGGCTGTGTCTGGCTAGATGGCTTGGTGTCTTACAATGCTCCAGCTGGGCAG

CAGTTTGTACTCCCTGGAGGTTCCATCATTTATCTGAATGATTCTGTCTATGATGGAGCT

GTTGGATACAGCATGACAGAAGGGCTAGGCCAATTGACCGATGGTGTGTCTGGCCTGGAC

GATTTCACCCAGACCCATGAATACCACGTGTGGCCCGGCTATGACTATGTGGGCTGGCGG

AACGAGAGTGCCACCAATGGCTACATTGAGATCATGTTTGAATTTGACCGCATCAGGAAT

TTCACTACCATGAAGGTCCACTGCAACAACATGTTTGCTAAAGGTGTGAAGATCTTTAAG

GAGGTACAGTGCTACTTCCGCTCTGAAGCCAGTGAGTGGGAACCTAATGCCATTTCCTTC

CCCCTTGTCCTGGATGACGTCAACCCCAGTGCTCGGTTTGTCACGGTGCCTCTCCACCAC

CGAATGGCCAGTGCCATCAAGTGTCAATACCATTTTGCAGATACCTGGATGATGTTCAGT

GAGATCACCTTCCAATCAGATGCTGCAATGTACAACAACTCTGAAGCCCTGCCCACCTCT

CCTATGGCACCCACAACCTATGATCCAATGCTTAAAGTTGATGACAGCAACACTCGGATC

CTGATTGGCTGCTTGGTGGCCATCATCTTTATCCTCCTGGCCATCATTGTCATCATCCTC

TGGAGGCAGTTCTGGCAGAAAATGCTGGAGAAGGCTTCTCGGAGGATGCTGGATGATGAA

ATGACAGTCAGCCTTTCCCTGCCAAGTGATTCTAGCATGTTCAACAATAACCGCTCCTCA

TCACCTAGTGAACAAGGGTCCAACTCGACTTACGATCGCATCTTTCCCCTTCGCCCTGAC

TACCAGGAGCCATCCAGGCTGATACGAAAACTCCCAGAATTTGCTCCAGGGGAGGAGGAG

TCAGGCTGCAGCGGTGTTGTGAAGCCAGTCCAGCCCAGTGGCCCTGAGGGGGTGCCCCAC

TATGCAGAGGCTGACATAGTGAACCTCCAAGGAGTGACAGGAGGCAACACATACTCAGTG

-continued

CCTGCCGTCACCATGGACCTGCTCTCAGGAAAAGATGTGGCTGTGGAGGAGTTCCCCAGG

AAACTCCTAACTTTCAAAGAGAAGCTGGGAGAAGGACAGTTTGGGGAGGTTCATCTCTGT

GAAGTGGAGGGAATGGAAAAATTCAAAGACAAAGATTTTGCCCTAGATGTCAGTGCCAAC

CAGCCTGTCCTGGTGGCTGTGAAAATGCTCCGAGCAGATGCCAACAAGAATGCCAGGAAT

GATTTTCTTAAGGAGATAAAGATCATGTCTCGGCTCAAGGACCCAAACATCATCCATCTA

TTATCTGTGTGTATCACTGATGACCCTCTCTGTATGATCACTGAATACATGGAGAATGGA

GATCTCAATCAGTTTCTTTCCCGCCACGAGCCCCCTAATTCTTCCTCCAGCGATGTACGC

ACTGTCAGTTACACCAATCTGAAGTTTATGGCTACCCAAATTGCCTCTGGCATGAAGTAC

CTTTCCTCTCTTAATTTTGTTCACCGAGATCTGGCCACACGAAACTGTTTAGTGGGTAAG

AACTACACAATCAAGATAGCTGACTTTGGAATGAGCAGGAACCTGTACAGTGGTGACTAT

TACCGGATCCAGGGCCGGGCAGTGCTCCCTATCCGCTGGATGTCTTGGGAGAGTATCTTG

CTGGGCAAGTTCACTACAGCAAGTGATGTGTGGGCCTTTGGGGTTACTTTGTGGGAGACT

TTCACCTTTTGTCAAGAACAGCCCTATTCCCAGCTGTCAGATGAACAGGTTATTGAGAAT

ACTGGAGAGTTCTTCCGAGACCAAGGGAGGCAGACTTACCTCCCTCAACCAGCCATTTGT

CCTGACTCTGTGTATAAGCTGATGCTCAGCTGCTGGAGAAGAGATACGAAGAACCGTCCC

TCATTCCAAGAAATCCACCTTCTGCTCCTTCAACAAGGCGACGAGTGA

Nucleotide sequence of DDR1-Fc (SEQ ID NO: 7)
ATGGGACCAGAGGCCCTGTCATCTTTACTGCTGCTGCTCTTGGTGGCAAGTGGAGATGCT

GACATGAAGGGACATTTTGATCCTGCCAAGTGCCGCTATGCCCTGGGCATGCAGGACCGG

ACCATCCCAGACAGTGACATCTCTGCTTCCAGCTCCTGGTCAGATTCCACTGCCGCCCGC

CACAGCAGGTTGGAGAGCAGTGACGGGGATGGGGCCTGGTGCCCCGCAGGGTCGGTGTTT

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACTGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

GAAATCTCCTTCATCTCTGATGTGGTGAACAATTCCTCTCCGGCACTGGGAGGCACCTTC

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCGGGCGCGCC

GACAAAACTCACACATGCCCACCGTGCCCAGCACCTGAACTCCTGGGGGGACCGTCAGTC

TTCCTCTTCCCCCCAAAACCCAAGGACACCCTCATGATCTCCCGGACCCCTGAGGTCACA

TGCGTGGTGGTGGACGTGAGCCACGAAGACCCTGAGGTCAAGTTCAACTGGTACGTGGAC

-continued

GGCGTGGAGGTGCATAATGCCAAGACAAAGCCGCGGGAGGAGCAGTACAACAGCACGTAC

CGTGTGGTCAGCGTCCTCACCGTCCTGCACCAGGACTGGCTGAATGGCAAGGAGTACAAG

TGCAAGGTCTCCAACAAAGCCCTCCCAGCCCCCATCGAGAAAACCATCTCCAAAGCCAAA

GGGCAGCCCCGAGAACCACAGGTGTACACCCTGCCCCCATCCCGGGATGAGCTGACCAAG

AACCAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGACTCC

GACGGCTCCTTCTTCCTCTACAGCAAGCTCACCGTGGACAAGAGCAGGTGGCAGCAGGGG

AACGTCTTCTCATGCTCCGTGATGCATGAGGCTCTGCACAACCACTACACACAGAAGAGC

CTCTCCCTGTCTCCGGGTAAA

Protein sequence of DDR1-Fc (SEQ ID NO: 8)
MGPEALSSLLLLLLVASGDADMKGHFDPAKCRYALGMQDRTIPDSDISASSSWSDSTAAR

HSRLESSDGDGAWCPAGSVFPKEEEYLQVDLQRLHLVALVGTQGRHAGGLGKEFSRSYRL

RYSRDGRRWMGWKDRWGQEVISGNEDPEGVVLKDLGPPMVARLVRFYPRADRVMSVCLRV

ELYGCLWRDGLLSYTAPVGQTMYLSEAVYLNDSTYDGHTVGGLQYGGLGQLADGVVGLDD

FRKSQELRVWPGYDYVGWSNHSFSSGYVEMEFEFDRLRAFQAMQVHCNNMHTLGARLPGG

VECRFRRGPAMAWEGEPMRHNLGGNLGDPRARAVSVPLGGRVARFLQCRFLFAGPWLLFS

EISFISDVVNNSSPALGGTFPPAPWWPPGPPPTNFSSLELEPRGQQPVAKAEGSPTAGRA

DKTHTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

Human DDR1a full length amino acid sequence (SEQ ID NO: 9)
MGPEALSSLLLLLLVASGDADMKGHFDPAKCRYALGMQDRTIPDSDISASSSWSDSTAAR

HSRLESSDGDGAWCPAGSVFPKEEEYLQVDLQRLHLVALVGTQGRHAGGLGKEFSRSYRL

RYSRDGRRWMGWKDRWGQEVISGNEDPEGVVLKDLGPPMVARLVRFYPRADRVMSVCLRV

ELYGCLWRDGLLSYTAPVGQTMYLSEAVYLNDSTYDGHTVGGLQYGGLGQLADGVVGLDD

FRKSQELRVWPGYDYVGWSNHSFSSGYVEMEFEFDRLRAFQAMQVHCNNMHTLGARLPGG

VECRFRRGPAMAWEGEPMRHNLGGNLGDPRARAVSVPLGGRVARFLQCRFLFAGPWLLFS

EISFISDVVNNSSPALGGTFPPAPWWPPGPPPTNFSSLELEPRGQQPVAKAEGSPTAILI

GCLVAIILLLLLIIALMLWRLHWRRLLSKAERRVLEEELTVHLSVPGDTILINNRPGPRE

PPPYQEPRPRGNPPHSAPCVPNGSAYSGDYMEPEKPGAPLLPPPPQNSVPHYAEADIVTL

QGVTGGNTYAVPALPPGAVGDGPPRVDFPRSRLRFKEKLGEGQFGEVHLCEVDSPQDLVS

LDFPLNVRKGHPLLVAVKILRPDATKNARNDFLKEVKIMSRLKDPNIIRLLGVCVQDDPL

CMITDYMENGDLNQFLSAHQLEDKAAEGAPGDGQAAQGPTISYPMLLHVAAQIASGMRYL

ATLNFVHRDLATRNCLVGENFTIKIADFGMSRNLYAGDYYRVQGRAVLPIRWMAWECILM

GKFTTASDVWAFGVTLWEVLMLCRAQPFGQLTDEQVIENAGEFFRDQGRQVYLSRPPACP

QGLYELMLRCWSRESEQRPPFSQLHRFLAEDALNTV

Human DDR1a full length nucleotide sequence (SEQ ID NO: 10)
ATGGGACCAGAGGCCCTGTCATCTTTACTGCTGCTGCTCTTGGTGGCAAGTGGAGATGCT

GACATGAAGGGACATTTTGATCCTGCCAAGTGCCGCTATGCCCTGGGCATGCAGGACCGG

ACCATCCCAGACAGTGACATCTCTGCTTCCAGCTCCTGGTCAGATTCCACTGCCGCCCGC

CACAGCAGGTTGGAGAGCAGTGACGGGGATGGGGCCTGGTGCCCCGCAGGGTCGGTGTTT

-continued

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACTGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

GAAATCTCCTTCATCTCTGATGTGGTGAACAATTCCTCTCCGGCACTGGGAGGCACCTTC

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCATCCTCATC

GGCTGCCTGGTGGCCATCATCCTGCTCCTGCTGCTCATCATTGCCCTCATGCTCTGGCGG

CTGCACTGGCGCAGGCTCCTCAGCAAGGCTGAACGGAGGGTGTTGGAAGAGGAGCTGACG

GTTCACCTCTCTGTCCCTGGGGACACTATCCTCATCAACAACCGCCCAGGTCCTAGAGAG

CCACCCCCGTACCAGGAGCCCCGGCCTCGTGGGAATCCGCCCCACTCCGCTCCCTGTGTC

CCCAATGGCTCTGCCTACAGTGGGGACTATATGGAGCCTGAGAAGCCAGGCGCCCCGCTT

CTGCCCCCACCTCCCCAGAACAGCGTCCCCCATTATGCCGAGGCTGACATTGTTACCCTG

CAGGGCGTCACCGGGGGCAACACCTATGCTGTGCCTGCACTGCCCCCAGGGGCAGTCGGG

GATGGGCCCCCCAGAGTGGATTTCCCTCGATCTCGACTCCGCTTCAAGGAGAAGCTTGGC

GAGGGCCAGTTTGGGGAGGTGCACCTGTGTGAGGTCGACAGCCCTCAAGATCTGGTTAGT

CTTGATTTCCCCCTTAATGTGCGTAAGGGACACCCTTTGCTGGTAGCTGTCAAGATCTTA

CGGCCAGATGCCACCAAGAATGCCAGGAATGATTTCCTGAAAGAGGTGAAGATCATGTCG

AGGCTCAAGGACCCAAACATCATTCGGCTGCTGGGCGTGTGTGTGCAGGACGACCCCCTC

TGCATGATTACTGACTACATGGAGAACGGCGACCTCAACCAGTTCCTCAGTGCCCACCAG

CTGGAGGACAAGGCAGCCGAGGGGGCCCCTGGGGACGGGCAGGCTGCGCAGGGGCCCACC

ATCAGCTACCCAATGCTGCTGCATGTGGCAGCCCAGATCGCCTCCGGCATGCGCTATCTG

GCCACACTCAACTTTGTACATCGGGACCTGGCCACGCGGAACTGCCTAGTTGGGGAAAAT

TTCACCATCAAAATCGCAGACTTTGGCATGAGCCGGAACCTCTATGCTGGGGACTATTAC

CGTGTGCAGGGCCGGGCAGTGCTGCCCATCCGCTGGATGGCCTGGGAGTGCATCCTCATG

GGGAAGTTCACGACTGCGAGTGACGTGTGGGCCTTTGGTGTGACCCTGTGGGAGGTGCTG

ATGCTCTGTAGGGCCCAGCCCTTTGGGCAGCTCACCGACGAGCAGGTCATCGAGAACGCG

GGGGAGTTCTTCCGGGACCAGGGCCGGCAGGTGTACCTGTCCCGGCCGCCTGGCTGCCCG

CAGGGCCTATATGAGCTGATGCTTCGGTGCTGGAGCCGGGAGTCTGAGCAGCGACCACCC

TTTTCCCAGCTGCATCGGTTCCTGGCAGAGGATGCACTCAACACGGTGTGA

-continued

Human DDR1b full length nucleotide sequence (SEQ ID NO: 11)

ATGGGACCAGAGGCCCTGTCATCTTTACTGCTGCTGCTCTTGGTGGCAAGTGGAGATGCT

GACATGAAGGGACATTTTGATCCTGCCAAGTGCCGCTATGCCCTGGGCATGCAGGACCGG

ACCATCCCAGACAGTGACATCTCTGCTTCCAGCTCCTGGTCAGATTCCACTGCCGCCCGC

CACAGCAGGTTGGAGAGCAGTGACGGGGATGGGGCCTGGTGCCCCGCAGGGTCGGTGTTT

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACCGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

GAAATCTCCTTCATCTCTGATGTGGTGAACAATTCCTCTCCGGCACTGGGAGGCACCTTC

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCATCCTCATC

GGCTGCCTGGTGGCCATCATCCTGCTCCTGCTGCTCATCATTGCCCTCATGCTCTGGCGG

CTGCACTGGCGCAGGCTCCTCAGCAAGGCTGAACGGAGGGTGTTGGAAGAGGAGCTGACG

GTTCACCTCTCTGTCCCTGGGGACACTATCCTCATCAACAACCGCCCAGGTCCTAGAGAG

CCACCCCCGTACCAGGAGCCCCGGCCTCGTGGGAATCCGCCCCACTCCGCTCCCTGTGTC

CCCAATGGCTCTGCGTTGCTGCTCTCCAATCCAGCCTACCGCCTCCTTCTGGCCACTTAC

GCCCGTCCCCCTCGAGGCCCGGGCCCCCCACACCCGCCTGGGCCAAACCCACCAACACC

CAGGCCTACAGTGGGGACTATATGGAGCCTGAGAAGCCAGGCGCCCCGCTTCTGCCCCCA

CCTCCCCAGAACAGCGTCCCCCATTATGCCGAGGCTGACATTGTTACCCTGCAGGGCGTC

ACCGGGGGCAACACCTATGCTGTGCCTGCACTGCCCCCAGGGGCAGTCGGGGATGGGCCC

CCCAGAGTGGATTTCCCTCGATCTCGACTCCGCTTCAAGGAGAAGCTTGGCGAGGGCCAG

TTTGGGGAGGTGCACCTGTGTGAGGTCGACAGCCCTCAAGATCTGGTTAGTCTTGATTTC

CCCCTTAATGTGCGTAAGGGACACCCTTTGCTGGTAGCTGTCAAGATCTTACGGCCAGAT

GCCACCAAGAATGCCAGGAATGATTTCCTGAAAGAGGTGAAGATCATGTCGAGGCTCAAG

GACCCAAACATCATTCGGCTGCTGGGCGTGTGTGTGCAGGACGACCCCCTCTGCATGATT

ACTGACTACATGGAGAACGGCGACCTCAACCAGTTCCTCAGTGCCCACCAGCTGGAGGAC

AAGGCAGCCGAGGGGGCCCCTGGGGACGGGCAGGCTGCGCAGGGGCCCACCATCAGCTAC

CCAATGCTGCTGCATGTGGCAGCCCAGATCGCCTCCGGCATGCGCTATCTGGCCACACTC

AACTTTGTACATCGGGACCTGGCCACGCGGAACTGCCTAGTTGGGGAAAATTTCACCATC

AAAATCGCAGACTTTGGCATGAGCCGGAACCTCTATGCTGGGGACTATTACCGTGTGCAG

-continued

GGCCGGGCAGTGCTGCCCATCCGCTGGATGGCCTGGGAGTGCATCCTCATGGGGAAGTTC

ACGACTGCGAGTGACGTGTGGGCCTTTGGTGTGACCCTGTGGGAGGTGCTGATGCTCTGT

AGGGCCCAGCCCTTTGGGCAGCTCACCGACGAGCAGGTCATCGAGAACGCGGGGGAGTTC

TTCCGGGACCAGGGCCGGCAGGTGTACCTGTCCCGGCCGCCTGCCTGCCCGCAGGGCCTA

TATGAGCTGATGCTTCGGTGCTGGAGCCGGGAGTCTGAGCAGCGACCACCCTTTTCCCAG

CTGCATCGGTTCCTGGCAGAGGATGCACTCAACACGGTGTGA

Human DDR1b full length amino acid sequence (SEQ ID NO: 12)
MGPEALSSLLLLLLVASGDADMKGHFDPAKCRYALGMQDRTIPDSDISASSSWSDSTAAR

HSRLESSDGDGAWCPAGSVFPKEEEYLQVDLQRLHLVALVGTQGRHAGGLGKEFSRSYRL

RYSRDGRRWMGWKDRWGQEVISGNEDPEGVVLKDLGPPMVARLVRFYPRADRVMSVCLRV

ELYGCLWRDGLLSYTAPVGQTMYLSEAVYLNDSTYDGHTVGGLQYGGLGQLADGVVGLDD

FRKSQELRVWPGYDYVGWSNHSFSSGYVEMEFEFDRLRAFQAMQVHCNNMHTLGARLPGG

VECRFRRGPAMAWEGEPMRHNLGGNLGDPRARAVSVPLGGRVARFLQCRFLFAGPWLLFS

EISFISDVVNNSSPALGGTFPPAPWWPPGPPPTNFSSLELEPRGQQPVAKAEGSPTAILI

GCLVAIILLLLLIIALMLWRLHWRRLLSKAERRVLEEELTVHLSVPGDTILINNRPGPRE

PPPYQEPRPRGNPPHSAPCVPNGSALLLSNPAYRLLLATYARPPRGPGPPTPAWAKPTNT

QAYSGDYMEPEKPGAPLLPPPPQNSVPHYAEADIVTLQGVTGGNTYAVPALPPGAVGDGP

PRVDFPRSRLRFKEKLGEGQFGEVHLCEVDSPQDLVSLDFPLNVRKGHPLLVAVKILRPD

ATKNARNDFLKEVKIMSRLKDPNIIRLLGVCVQDDPLCMITDYMENGDLNQFLSAHQLED

KAAEGAPGDGQAAQGPTISYPMLLHVAAQIASGMRYLATLNFVHRDLATRNCLVGENFTI

KIADFGMSRNLYAGDYYRVQGRAVLPIRWMAWECILMGKFTTASDVWAFGVTLWEVLMLC

RAQPFGQLTDEQVIENAGEFFRDQGRQVYLSRPPACPQGLYELMLRCWSRESEQRPPFSQ

LHRFLAEDALNTV

Human DDR1c full length nucleotide sequence (SEQ ID NO: 13)
ATGGGACCAGAGGCCCTGTCATCTTTACTGCTGCTGCTCTTGGTGGCAAGTGGAGATGCT

GACATGAAGGGACATTTTGATCCTGCCAAGTGCCGCTATGCCCTGGGCATGCAGGACCGG

ACCATCCCAGACAGTGACATCTCTGCTTCCAGCTCCTGGTCAGATTCCACTGCCGCCCGC

CACAGCAGGTTGGAGAGCAGTGACGGGGATGGGGCCTGGTGCCCCGCAGGGTCGGTGTTT

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACCGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

-continued

GAAATCTCCTTCATCTCTGATGTGGTGAACAATTCCTCTCCGGCACTGGGAGGCACCTTC

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCATCCTCATC

GGCTGCCTGGTGGCCATCATCCTGCTCCTGCTGCTCATCATTGCCCTCATGCTCTGGCGG

CTGCACTGGCGCAGGCTCCTCAGCAAGGCTGAACGGAGGGTGTTGGAAGAGGAGCTGACG

GTTCACCTCTCTGTCCCTGGGGACACTATCCTCATCAACAACCGCCCAGGTCCTAGAGAG

CCACCCCCGTACCAGGAGCCCCGGCCTCGTGGGAATCCGCCCCACTCCGCTCCCTGTGTC

CCCAATGGCTCTGCGTTGCTGCTCTCCAATCCAGCCTACCGCCTCCTTCTGGCCACTTAC

GCCCGTCCCCCTCGAGGCCCGGGCCCCCCCACACCCGCCTGGGCCAAACCCACCAACACC

CAGGCCTACAGTGGGGACTATATGGAGCCTGAGAAGCCAGGCGCCCCGCTTCTGCCCCCA

CCTCCCCAGAACAGCGTCCCCCATTATGCCGAGGCTGACATTGTTACCCTGCAGGGCGTC

ACCGGGGGCAACACCTATGCTGTGCCTGCACTGCCCCCAGGGGCAGTCGGGGATGGGCCC

CCCAGAGTGGATTTCCCTCGATCTCGACTCCGCTTCAAGGAGAAGCTTGGCGAGGGCCAG

TTTGGGGAGGTGCACCTGTGTGAGGTCGACAGCCCTCAAGATCTGGTTAGTCTTGATTTC

CCCCTTAATGTGCGTAAGGGACACCCTTTGCTGGTAGCTGTCAAGATCTTACGGCCAGAT

GCCACCAAGAATGCCAGCTTCTCCTTGTTCTCCAGGAATGATTTCCTGAAAGAGGTGAAG

ATCATGTCGAGGCTCAAGGACCCAAACATCATTCGGCTGCTGGGCGTGTGTGTGCAGGAC

GACCCCCTCTGCATGATTACTGACTACATGGAGAACGGCGACCTCAACCAGTTCCTCAGT

GCCCACCAGCTGGAGGACAAGGCAGCCGAGGGGGCCCCTGGGGACGGGCAGGCTGCGCAG

GGGCCCACCATCAGCTACCCAATGCTGCTGCATGTGGCAGCCCAGATCGCCTCCGGCATG

CGCTATCTGGCCACACTCAACTTTGTACATCGGGACCTGGCCACGCGGAACTGCCTAGTT

GGGGAAAATTTCACCATCAAAATCGCAGACTTTGGCATGAGCCGGAACCTCTATGCTGGG

GACTATTACCGTGTGCAGGGCCGGGCAGTGCTGCCCATCCGCTGGATGGCCTGGGAGTGC

ATCCTCATGGGGAAGTTCACGACTGCGAGTGACGTGTGGGCCTTTGGTGTGACCCTGTGG

GAGGTGCTGATGCTCTGTAGGGCCCAGCCCTTTGGGCAGCTCACCGACGAGCAGGTCATC

GAGAACGCGGGGGAGTTCTTCCGGGACCAGGGCCGGCAGGTGTACCTGTCCCGGCCGCCT

GCCTGCCCGCAGGGCCTATATGAGCTGATGCTTCGGTGCTGGAGCCGGGAGTCTGAGCAG

CGACCACCCTTTTCCCAGCTGCATCGGTTCCTGGCAGAGGATGCACTCAACACGGTGTGA

Human DDR1c full length amino acid sequence (SEQ ID NO: 14)
MGPEALSSLLLLLLVASGDADMKGHFDPAKCRYALGMQDRTIPDSDISASSSWSDSTAAR

HSRLESSDGDGAWCPAGSVFPKEEEYLQVDLQRLHLVALVGTQGRHAGGLGKEFSRSYRL

RYSRDGRRWMGWKDRWGQEVISGNEDPEGVVLKDLGPPMVARLVRFYPRADRVMSVCLRV

ELYGCLWRDGLLSYTAPVGQTMYLSEAVYLNDSTYDGHTVGGLQYGGLGQLADGVVGLDD

FRKSQELRVWPGYDYVGWSNHSFSSGYVEMEFEFDRLRAFQAMQVHCNNMHTLGARLPGG

VECRFRRGPAMAWEGEPMRHNLGGNLGDPRARAVSVPLGGRVARFLQCRFLFAGPWLLFS

EISFISDVVNNSSPALGGTFPPAPWWPPGPPPTNFSSLELEPRGQQPVAKAEGSPTAILI

GCLVAIILLLLLIIALMLWRLHWRRLLSKAERRVLEEELTVHLSVPGDTILINNRPGPRE

PPPYQEPRPRGNPPHSAPCVPNGSALLLSNPAYRLLLATYARPPRGPGPPTPAWAKPTNT

QAYSGDYMEPEKPGAPLLPPPPQNSVPHYAEADIVTLQGVTGGNTYAVPALPPGAVGDGP

PRVDFPRSRLRFKEKLGEGQFGEVHLCEVDSPQDLVSLDFPLNVRKGHPLLVAVKILRPD

ATKNASFSLFSRNDFLKEVKIMSRLKDPNIIRLLGVCVQDDPLCMITDYMENGDLNQFLS

-continued

AHQLEDKAAEGAPGDGQAAQGPTISYPMLLHVAAQIASGMRYLATLNFVHRDLATRNCLV

GENFTIKIADFGMSRNLYAGDYYRVQGRAVLPIRWMAWECILMGKFTTASDVWAFGVTLW

EVLMLCRAQPFGQLTDEQVIENAGEFFRDQGRQVYLSRPPACPQGLYELMLRCWSRESEQ

RPPFSQLHRFLAEDALNTV

Human DDR1 mature ECD amino acid sequence (SEQ ID NO: 15)
DMKGHFDPAKCRYALGMQDRTIPDSDISASSSWSDSTAARHSRLESSDGDGAWCPAGSVF

PKEEEYLQVDLQRLHLVALVGTQGRHAGGLGKEFSRSYRLRYSRDGRRWMGWKDRWGQEV

ISGNEDPEGVVLKDLGPPMVARLVRFYPRADRVMSVCLRVELYGCLWRDGLLSYTAPVGQ

TMYLSEAVYLNDSTYDGHTVGGLQYGGLGQLADGVVGLDDFRKSQELRVWPGYDYVGWSN

HSFSSGYVEMEFEFDRLRAFQAMQVHCNNMHTLGARLPGGVECRFRRGPAMAWEGEPMRH

NLGGNLGDPRARAVSVPLGGRVARFLQCRFLFAGPWLLFSEISFISDVVNNSSPALGGTF

PPAPWWPPGPPPTNFSSLELEPRGQQPVAKAEGSPTA

20M102 Heavy chain nucleotide sequence (SEQ ID NO: 16)
Signal sequence is underlined
ATGAAATGGACCTGGGTCATCCTCTTTCTCTTGTCAGGAACTGGAGGTGTCCTCTCTGAG

GTCCAGCTGCAACAGTCTGGATCTGAGCTGGTGAAGCCTGGGGCTTCAGTGAAGATGTCC

TGCAAGGCTTCTGGATACACCTTCACTGACTACTTCATGAAGTGGGTGAAGCAGAGCCAT

GGAAAGAGCCTTGAATGGATTGGAGATATTAATCCCAACAATGGTGATACTTTCTACATC

CAGAAGTTCAAGGGCAAGGCCACTTTGACTGTAGACAAATCCTCCAGTACAGCCTACATG

CAGCTCAACAGCCTGACATCTGAGGACTCTGCAGTCTATTACTGTTCAAGAGACCTTGCT

TACTGGGGCCAAGGGACTCTGGTCGCTGTCTCCTCAGCCAAAACGACACCCCCATCTGTC

TATCCACTGGCCCCTGGATCTGCTGCCCAAACTAACTCCATGGTGACCCTGGGATGCCTG

GTCAAGGGCTATTTCCCTGAGCCAGTGACAGTGACCTGGAACTCTGGATCCCTGTCCAGC

GGTGTGCACACCTTCCCAGCTGTCCTGCAGTCTGACCTCTACACTCTGAGCAGCTCAGTG

ACTGTCCCCTCCAGCACCTGGCCCAGCGAGACCGTCACCTGCAACGTTGCCCACCCGGCC

AGCAGCACCAAGGTGGACAAGAAAATTGTGCCCAGGGATTGTGGTTGTAAGCCTTGCATA

TGTACAGTCCCAGAAGTATCATCTGTCTTCATCTTCCCCCCAAAGCCCAAGGATGTGCTC

ACCATTACTCTGACTCCTAAGGTCACGTGTGTTGTGGTAGACATCAGCAAGGATGATCCC

GAGGTCCAGTTCAGCTGGTTTGTAGATGATGTGGAGGTGCACACAGCTCAGACGCAACCC

CGGGAGGAGCAGTTCAACAGCACTTTCCGCTCAGTCAGTGAACTTCCCATCATGCACCAG

GACTGGCTCAATGGCAAGGAGTTCAAATGCAGGGTCAACAGTGCAGCTTTCCCTGCCCCC

ATCGAGAAAACCATCTCCAAAACCAAAGGCAGACCGAAGGCTCCACAGGTGTACACCATT

CCACCTCCCAAGGAGCAGATGGCCAAGGATAAAGTCAGTCTGACCTGCATGATAACAGAC

TTCTTCCCTGAAGACATTACTGTGGAGTGGCAGTGGAATGGGCAGCCAGCGGAGAACTAC

AAGAACACTCAGCCCATCATGGACACAGATGGCTCTTACTTCGTCTACAGCAAGCTCAAT

GTGCAGAAGAGCAACTGGGAGGCAGGAAATACTTTCACCTGCTCTGTGTTACATGAGGGC

CTGCACAACCACCATACTGAGAAGAGCCTCTCCCACTCTCCTGGTAAATGA

20M102 Heavy chain amino acid sequence (SEQ ID NO: 17)
Signal sequence is underlined
MKWTWVILFLLSGTGGVLSEVQLQQSGSELVKPGASVKMSCKASGYTFTDYFMKWVKQSH

GKSLEWIGDINPNNGDTFYIQKFKGKATLTVDKSSSTAYMQLNSLTSEDSAVYYCSRDLA

YWGQGTLVAVSSAKTTPPSVYPLAPGSAAQTNSMVTLGCLVKGYFPEPVTVTWNSGSLSS

GVHTFPAVLQSDLYTLSSSVTVPSSTWPSETVTCNVAHPASSTKVDKKIVPRDCGCKPCI

-continued

CTVPEVSSVFIFPPKPKDVLTITLTPKVTCVVVDISKDDPEVQFSWFVDDVEVHTAQTQP

REEQFNSTFRSVSELPIMHQDWLNGKEFKCRVNSAAFPAPIEKTISKTKGRPKAPQVYTI

PPPKEQMAKDKVSLTCMITDFFPEDITVEWQWNGQPAENYKNTQPIMDTDGSYFVYSKLN

VQKSNWEAGNTFTCSVLHEGLHNHHTEKSLSHSPGK

20MI02 Light chain nucleotide sequence (SEQ ID NO: 18)
Signal sequence is underlined
ATGAAGTTGCCTGTTAGGCTGTTGGTGCTCTGGATTCAGGAAACCAACGGTGATGTTGTG

ATGACCCAGACTCCACTCACTTTGTCGGTTAACATTGGACAACCAGCCTCTATCTCTTGC

AAGTCAAGTCAGAGCCTCTTATATAGTAATGGGAAAACCTATTTGAATTGGTTATTACAG

AGGCCAGGCCAGTCTCCAAGGCGCCTAATCTATCAGGTGTCTAAACTGGACTCTGGAGTC

CCTGACAGGTTCACTGGCAGTGGATCAGGAACAGATTTTACATTGAAAATCAGCAGAGTG

GAGGCTGAGGATTTGGGAGTTTATTACTGCGTGCAAGGTACAGATTTTCCTCAGACGTTC

GGTGGAGGCACCAAGCTGGAAATCAAACGGGCTGATGCTGCACCAACTGTATCCATCTTC

CCACCATCCAGTGAGCAGTTAACATCTGGAGGTGCCTCAGTCGTGTGCTTCTTGAACAAC

TTCTACCCCAAAGACATCAATGTCAAGTGGAAGATTGATGGCAGTGAACGACAAAATGGC

GTCCTGAACAGTTGGACTGATCAGGACAGCAAAGACAGCACCTACAGCATGAGCAGCACC

CTCACGTTGACCAAGGACGAGTATGAACGACATAACAGCTATACCTGTGAGGCCACTCAC

AAGACATCAACTTCACCCATCGTCAAGAGCTTCTTCAACAGGAATGAGTGTTAG

20M102 Light chain amino acid sequence (SEQ ID NO: 19)
Signal sequence is underlined
MKLPVRLLVLWIQETNGDVVMTQTPLTLSVNIGQPASISCKSSQSLLYSNGKTYLNWLLQ

RPGQSPRRLIYQVSKLDSGVPDRFTGSGSGTDFTLKISRVEAEDLGVYYCVQGTDFPQTF

GGGTKLEIKRADAAPTVSIFPPSSEQLTSGGASVVCFLNNFYPKDINVKWKIDGSERQNG

VLNSWTDQDSKDSTYSMSSTLTLTKDEYERHNSYTCEATHKTSTSPIVKSFNRNEC

20M102 Heavy chain variable region nucleotide sequence (SEQ ID NO: 20)
Signal sequence is underlined
ATGAAATGGACCTGGGTCATCCTCTTTCTCTTGTCAGGAACTGGAGGTGTCCTCTCTGAG

GTCCAGCTGCAACAGTCTGGATCTGAGCTGGTGAAGCCTGGGGCTTCAGTGAAGATGTCC

TGCAAGGCTTCTGGATACACCTTCACTGACTACTTCATGAAGTGGGTGAAGCAGAGCCAT

GGAAAGAGCCTTGAATGGATTGGAGATATTAATCCCAACAATGGTGATACTTTCTACATC

CAGAAGTTCAAGGGCAAGGCCACTTTGACTGTAGACAAATCCTCCAGTACAGCCTACATG

CAGCTCAACAGCCTGACATCTGAGGACTCTGCAGTCTATTACTGTTCAAGAGACCTTGCT

TACTGGGGCCAAGGGACTCTGGTCGCTGTC

20M102 Heavy chain variable region amino acid sequence (SEQ ID NO: 21)
Signal sequence is underlined
MKWTWVILFLLSGTGGVLSEVQLQQSGSELVKPGASVKMSCKASGYTFTDYFMKWVKQSH

GKSLEWIGDINPNNGDTFYIQKFKGKATLTVDKSSSTAYMQLNSLTSEDSAVYYCSRDLA

YWGQGTLVAV

20M102 Heavy chain CDR1 amino acid sequence (SEQ ID NO: 22)
GYTFTDYFMK

20M102 Heavy chain CDR2 amino acid sequence (SEQ ID NO: 23)
DINPNNGDTFYIQKFKG

20M102 Heavy chain CDR3 amino acid sequence (SEQ ID NO: 24)
SRDLAY

-continued

20M102 Light chain variable region nucleotide sequence (SEQ ID NO: 25)
Signal sequence is underlined
ATGAAGTTGCCTGTTAGGCTGTTGGTGCTCTGGATTCAGGAAACCAACGGTGATGTTGTG

ATGACCCAGACTCCACTCACTTTGTCGGTTAACATTGGACAACCAGCCTCTATCTCTTGC

AAGTCAAGTCAGAGCCTCTTATATAGTAATGGGAAAACCTATTTGAATTGGTTATTACAG

AGGCCAGGCCAGTCTCCAAGGCGCCTAATCTATCAGGTGTCTAAACTGGACTCTGGAGTC

CCTGACAGGTTCACTGGCAGTGGATCAGGAACAGATTTTACATTGAAAATCAGCAGAGTG

GAGGCTGAGGATTTGGGAGTTTATTACTGCGTGCAAGGTACAGATTTTCCTCAGACGTTC

GGTGGAGGC

20M102 Light chain variable region amino acid sequence (SEQ ID NO: 26)
Signal sequence is underlined
MKLPVRLLVLWIQETNGDVVMTQTPLTLSVNIGQPASISCKSSQSLLYSNGKTYLNWLLQ

RPGQSPRRLIYQVSKLDSGVPDRFTGSGSGTDFTLKISRVEAEDLGVYYCVQGTDFPQTF

GGG

20M102 Light chain CDR1 amino acid sequence (SEQ ID NO: 27)
KSSQSLLYSNGKTYLN

20M102 Light chain CDR2 amino acid sequence (SEQ ID NO: 28)
QVSKLDS

20M102 Light chain CDR3 amino acid sequence (SEQ ID NO: 29)
VQGTDFPQT

Partial DDR1 amino acid sequence (SEQ ID NO: 30)
SASSSWSDSTAAR

Partial DDR1 amino acid sequence with substitution (SEQ ID NO: 31)
SASSSASDSTAAR 20M102 Heavy chair variable region nucleotide sequence without signal sequence (SEQ ID NO: 32)
GAGGTCCAGCTGCAACAGTCTGGATCTGAGCTGGTGAAGCCTGGGGCTTCAGTGAAGATG

TCCTGCAAGGCTTCTGGATACACCTTCACTGACTACTTCATGAAGTGGGTGAAGCAGAGC

CATGGAAAGAGCCTTGAATGGATTGGAGATATTAATCCCAACAATGGTGATACTTTCTAC

ATCCAGAAGTTCAAGGGCAAGGCCACTTTGACTGTAGACAAATCCTCCAGTACAGCCTAC

ATGCAGCTCAACAGCCTGACATCTGAGGACTCTGCAGTCTATTACTGTTCAAGAGACCTT

GCTTACTGGGGCCAAGGGACTCTGGTCGCTGTC

20M102 Heavy chain variable region amino acid sequence without signal sequence (SEQ ID NO: 33)
EVQLQQSGSELVKPGASVKMSCKASGYTFTDYFMKWVKQSHGKSLEWIGDINPNNGDTFY

IQKFKGKATLTVDKSSSTAYMQLNSLTSEDSAVYYCSRDLAYWGQGTLVAV

20M102 Light chain variable region nucleotide sequence without signal sequence (SEQ ID NO: 34)
GATGTTGTGATGACCCAGACTCCACTCACTTTGTCGGTTAACATTGGACAACCAGCCTCT

ATCTCTTGCAAGTCAAGTCAGAGCCTCTTATATAGTAATGGGAAAACCTATTTGAATTGG

TTATTACAGAGGCCAGGCCAGTCTCCAAGGCGCCTAATCTATCAGGTGTCTAAACTGGAC

TCTGGAGTCCCTGACAGGTTCACTGGCAGTGGATCAGGAACAGATTTTACATTGAAAATC

AGCAGAGTGGAGGCTGAGGATTTGGGAGTTTATTACTGCGTGCPAGGTACAGATTTTCCT

CAGACGTTCGGTGGAGGC

20M102 Light chain variable region amino acid sequence without signal sequence (SEQ ID NO: 35)
DVVMTQTPLTLSVNIGQPASISCKSSQSLLYSNGKTYLNWLLQRPGQSPRRLIYQVSKLD

SGVPDRFTGSGSGTDFTLKISRVEAEDLGVYYCVQGTDFPQTFGGG

Human DDR1-FLAG construct sequence (SEQ ID NO: 36)

-continued

ATGTCTGCACTTCTGATCCTAGCTCTTGTTGGAGCTGCAGTTGCTGACTACAAAGACCAT

GACGGTGATTATAAAGATCATGACATCGATTACAAGGATGACGATGACAAGGCGATCGCG

GACATGAAGGGACATTTTGATCCTGCCAAGTGCCGCTATGCCCTGGGCATGCAGGACCGG

ACCATCCCAGACAGTGACATCTCTGCTTCCAGCTCCTGGTCAGATTCCACTGCCGCCCGC

CACAGCAGGTTGGAGAGCAGTGACGGGGATGGGGCCTGGTGCCCCGCAGGGTCGGTGTTT

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACTGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

GAAATCTCCTTCATCTCTGATGTGGTGAACAATTCCTCTCCGGCACTGGGAGGCACCTTC

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCATCCTCATC

GGCTGCCTGGTGGCCATCATCCTGCTCCTGCTGCTCATCATTGCCCTCATGCTCTGGCGG

CTGCACTGGCGCAGGCTCCTCAGCAAGGCTGAACGGAGGGTGTTGGAAGAGGAGCTGACG

GTTCACCTCTCTGTCCCTGGGGACACTATCCTCATCAACAACCGCCCAGGTCCTAGAGAG

CCACCCCCGTACCAGGAGCCCCGGCCTCGTGGGAATCCGCCCCACTCCGCTCCCTGTGTC

CCCAATGGCTCTGCCTACAGTGGGGACTATATGGAGCCTGAGAAGCCAGGCGCCCCGCTT

CTGCCCCCACCTCCCCAGAACAGCGTCCCCCATTATGCCGAGGCTGACATTGTTACCCTG

CAGGGCGTCACCGGGGGCAACACCTATGCTGTGCCTGCACTGCCCCCAGGGGCAGTCGGG

GATGGGCCCCCCAGAGTGGATTTCCCTCGATCTCGACTCCGCTTCAAGGAGAAGCTTGGC

GAGGGCCAGTTTGGGGAGGTGCACCTGTGTGAGGTCGACAGCCCTCAAGATCTGGTTAGT

CTTGATTTCCCCCTTAATGTGCGTAAGGGACACCCTTTGCTGGTAGCTGTCAAGATCTTA

CGGCCAGATGCCACCAAGAATGCCAGGAATGATTTCCTGAAAGAGGTGAAGATCATGTCG

AGGCTCAAGGACCCAAACATCATTCGGCTGCTGGGCGTGTGTGTGCAGGACGACCCCCTC

TGCATGATTACTGACTACATGGAGAACGGCGACCTCAACCAGTTCCTCAGTGCCCACCAG

CTGGAGGACAAGGCAGCCGAGGGGGCCCCTGGGGACGGGCAGGCTGCGCAGGGGCCCACC

ATCAGCTACCCAATGCTGCTGCATGTGGCAGCCCAGATCGCCTCCGGCATGCGCTATCTG

GCCACACTCAACTTTGTACATCGGGACCTGGCCACGCGGAACTGCCTAGTTGGGGAAAAT

TTCACCATCAAAATCGCAGACTTTGGCATGAGCCGGAACCTCTATGCTGGGGACTATTAC

CGTGTGCAGGGCCGGGCAGTGCTGCCCATCCGCTGGATGGCCTGGGAGTGCATCCTCATG

GGGAAGTTCACGACTGCGAGTGACGTGTGGGCCTTTGGTGTGACCCTGTGGGAGGTGCTG

-continued

ATGCTCTGTAGGGCCCAGCCCTTTGGGCAGCTCACCGACGAGCAGGTCATCGAGAACGCG

GGGGAGTTCTTCCGGGACCAGGGCCGGCAGGTGTACCTGTCCCGGCCGCCTGCCTGCCCG

CAGGGCCTATATGAGCTGATGCTTCGGTGCTGGAGCCGGGAGTCTGAGCAGCGACCACCC

TTTTCCCAGCTGCATCGGTTCCTGGCAGAGGATGCACTCAACACGGTGTGA

Human DDR1-FLAG construct full length amino acid sequence (SEQ ID NO: 37)
MSALLILALVGAAVADYKDHDGDYKDHDIDYKDDDDKAIADMKGHFDPAKCRYALGMQDR

TIPDSDISASSSWSDSTAARHSRLESSDGDGAWCPAGSVFPKEEEYLQVDLQRLHLVALV

GTQGRHAGGLGKEFSRSYRLRYSRDGRRWMGWKDRWGQEVISGNEDPEGVVLKDLGPPMV

ARLVRFYPRADRVMSVCLRVELYGCLWRDGLLSYTAPVGQTMYLSEAVYLNDSTYDGHTV

GGLQYGGLGQLADGVVGLDDFRKSQELRVWPGYDYVGWSNHSFSSGYVEMEFEFDRLRAF

QAMQVHCNNMHTLGARLPGGVECRFRRGPAMAWEGEPMRHNLGGNLGDPRARAVSVPLGG

RVARFLQCRFLFAGPWLLFSEISFISDVVNNSSPALGGTFPPAPWWPPGPPPTNFSSLEL

EPRGQQPVAKAEGSPTAILIGCLVAIILLLLLIIALMLWRLHWRRLLSKAERRVLEEELT

VHLSVPGDTILINNRPGPREPPPYQEPRPRGNPPHSAPCVPNGSAYSGDYMEPEKPGAPL

LPPPPQNSVPHYAEADIVTLQGVTGGNTYAVPALPPGAVGDGPPRVDFPRSRLRFKEKLG

EGQFGEVHLCEVDSPQDLVSLDFPLNVRKGHPLLVAVKILRPDATKNARNDFLKEVKIMS

RLKDPNIIRLLGVCVQDDPLCMITDYMENGDLNQFLSAHQLEDKAAEGAPGDGQAAQGPT

ISYPMLLHVAAQIASGMRYLATLNFVHRDLATRNCLVGENFTIKIADFGMSRNLYAGDYY

RVQGRAVLPIRWMAWECILMGKFTTASDVWAFGVTLWEVLMLCRAQPFGQLTDEQVIENA

GEFFRDQGRQVYLSRPPACPQGLYELMLRCWSRESEQRPPFSQLHRFLAEDALNTV

Human DDR1 W53A Mutant-FLAG construct (SEQ ID NO: 38)
ATGTCTGCACTTCTGATCCTAGCTCTTGTTGGAGCTGCAGTTGCTGACTACAAAGACCAT

GACGGTGATTATAAAGATCATGACATCGATTACAAGGATGACGATGACAAGGCGATCGCG

GACATGAAGGGACATTTTGATCCTGCCAAGTGCCGCTATGCCCTGGGCATGCAGGACCGG

ACCATCCCAGACAGTGACATCTCTGCTTCCAGCTCCGCGTCAGATTCCACTGCCGCCCGC

CACAGCAGGTTGGAGAGCAGTGACGGGGATGGGGCCTGGTGCCCCGCAGGGTCGGTGTTT

CCCAAGGAGGAGGAGTACTTGCAGGTGGATCTACAACGACTGCACCTGGTGGCTCTGGTG

GGCACCCAGGGACGGCATGCCGGGGGCCTGGGCAAGGAGTTCTCCCGGAGCTACCGGCTG

CGTTACTCCCGGGATGGTCGCCGCTGGATGGGCTGGAAGGACCGCTGGGGTCAGGAGGTG

ATCTCAGGCAATGAGGACCCTGAGGGAGTGGTGCTGAAGGACCTTGGGCCCCCCATGGTT

GCCCGACTGGTTCGCTTCTACCCCCGGGCTGACCGGGTCATGAGCGTCTGTCTGCGGGTA

GAGCTCTATGGCTGCCTCTGGAGGGATGGACTCCTGTCTTACACTGCCCCTGTGGGGCAG

ACAATGTATTTATCTGAGGCCGTGTACCTCAACGACTCCACCTATGACGGACATACCGTG

GGCGGACTGCAGTATGGGGGTCTGGGCCAGCTGGCAGATGGTGTGGTGGGGCTGGATGAC

TTTAGGAAGAGTCAGGAGCTGCGGGTCTGGCCAGGCTATGACTATGTGGGATGGAGCAAC

CACAGCTTCTCCAGTGGCTATGTGGAGATGGAGTTTGAGTTTGACCGGCTGAGGGCCTTC

CAGGCTATGCAGGTCCACTGTAACAACATGCACACGCTGGGAGCCCGTCTGCCTGGCGGG

GTGGAATGTCGCTTCCGGCGTGGCCCTGCCATGGCCTGGGAGGGGGAGCCCATGCGCCAC

AACCTAGGGGGCAACCTGGGGGACCCCAGAGCCCGGGCTGTCTCAGTGCCCCTTGGCGGC

CGTGTGGCTCGCTTTCTGCAGTGCCGCTTCCTCTTTGCGGGGCCCTGGTTACTCTTCAGC

GAAATCTCCTTCATCTCTGATGTGGTGAACAATTCCTCTCCGGCACTGGGAGGCACCTTC

-continued

CCGCCAGCCCCCTGGTGGCCGCCTGGCCCACCTCCCACCAACTTCAGCAGCTTGGAGCTG

GAGCCCAGAGGCCAGCAGCCCGTGGCCAAGGCCGAGGGGAGCCCGACCGCCATCCTCATC

GGCTGCCTGGTGGCCATCATCCTGCTCCTGCTGCTCATCATTGCCCTCATGCTCTGGCGG

CTGCACTGGCGCAGGCTCCTCAGCAAGGCTGAACGGAGGGTGTTGGAAGAGGAGCTGACG

GTTCACCTCTCTGTCCCTGGGGACACTATCCTCATCAACAACCGCCCAGGTCCTAGAGAG

CCACCCCCGTACCAGGAGCCCCGGCCTCGTGGGAATCCGCCCCACTCCGCTCCCTGTGTC

CCCAATGGCTCTGCCTACAGTGGGGACTATATGGAGCCTGAGAAGCCAGGCGCCCCGCTT

CTGCCCCCACCTCCCCAGAACAGCGTCCCCCATTATGCCGAGGCTGACATTGTTACCCTG

CAGGGCGTCACCGGGGGCAACACCTATGCTGTGCCTGCACTGCCCCCAGGGGCAGTCGGG

GATGGGCCCCCCAGAGTGGATTTCCCTCGATCTCGACTCCGCTTCAAGGAGAAGCTTGGC

GAGGGCCAGTTTGGGGAGGTGCACCTGTGTGAGGTCGACAGCCCTCAAGATCTGGTTAGT

CTTGATTTCCCCCTTAATGTGCGTAAGGGACACCCTTTGCTGGTAGCTGTCAAGATCTTA

CGGCCAGATGCCACCAAGAATGCCAGGAATGATTTCCTGAAAGAGGTGAAGATCATGTCG

AGGCTCAAGGACCCAAACATCATTCGGCTGCTGGGCGTGTGTGTGCAGGACGACCCCCTC

TGCATGATTACTGACTACATGGAGAACGGCGACCTCAACCAGTTCCTCAGTGCCCACCAG

CTGGAGGACAAGGCAGCCGAGGGGGCCCCTGGGGACGGGCAGGCTGCGCAGGGGCCCACC

ATCAGCTACCCAATGCTGCTGCATGTGGCAGCCCAGATCGCCTCCGGCATGCGCTATCTG

GCCACACTCAACTTTGTACATCGGGACCTGGCCACGCGGAACTGCCTAGTTGGGGAAAAT

TTCACCATCAAAATCGCAGACTTTGGCATGAGCCGGAACCTCTATGCTGGGGACTATTAC

CGTGTGCAGGGCCGGGCAGTGCTGCCCATCCGCTGGATGGCCTGGGAGTGCATCCTCATG

GGGAAGTTCACGACTGCGAGTGACGTGTGGGCCTTTGGTGTGACCCTGTGGGAGGTGCTG

ATGCTCTGTAGGGCCCAGCCCTTTGGGCAGCTCACCGACGAGCAGGTCATCGAGAACGCG

GGGGAGTTCTTCCGGGACCAGGGCCGGCAGGTGTACCTGTCCCGGCCGCCTGCCTGCCCG

CAGGGCCTATATGAGCTGATGCTTCGGTGCTGGAGCCGGGAGTCTGAGCAGCGACCACCC

TTTTCCCAGCTGCATCGGTTCCTGGCAGAGGATGCACTCAACACGGTGTGA

Human DDR1 W53A Mutant-FLAG construct full length amino acid sequence (SEQ ID NO: 39)

MSALLILALVGAAVADYKDHDGDYKDHDIDYKDDDDKAIADMKGHFDPAKCRYALGMQDR

TIPDSDISASSSASDSTAARHSRLESSDGDGAWCPAGSVFPKEEEYLQVDLQRLHLVALV

GTQGRHAGGLGKEFSRSYRLRYSRDGRRWMGWKDRWGQEVISGNEDPEGVVLKDLGPPMV

ARLVRFYPRADRVMSVCLRVELYGCLWRDGLLSYTAPVGQTMYLSEAVYLNDSTYDGHTV

GGLQYGGLGQLADGVVGLDDFRKSQELRVWPGYDYVGWSNHSFSSGYVEMEFEFDRLRAF

QAMQVHCNNMHTLGARLPGGVECRFRRGPAMAWEGEPMRHNLGGNLGDPRARAVSVPLGG

RVARFLQCRFLFAGPWLLFSEISFISDVVNNSSPALGGTFPPAPWWPPGPPPTNFSSLEL

EPRGQQPVAKAEGSPTAILIGCLVAIILLLLLIIALMLWRLHWRRLLSKAERRVLEEELT

VHLSVPGDTILINNRPGPREPPPYQEPRPRGNPPHSAPCVPNGSAYSGDYMEPEKPGAPL

LPPPPQNSVPHYAEADIVTLQGVTGGNTYAVPALPPGAVGDGPPRVDFPRSRLRFKEKLG

EGQFGEVHLCEVDSPQDLVSLDFPLNVRKGHPLLVAVKILRPDATKNARNDFLKEVKIMS

RLKDPNIIRLLGVCVQDDPLCMITDYMENGDLNQFLSAHQLEDKAAEGAPGDGQAAQGPT

ISYPMLLHVAAQIASGMRYLATLNFVHRDLATRNCLVGENFTIKIADFGMSRNLYAGDYY

RVQGRAVLPIRWMAWECILMGKFTTASDVWAFGVTLWEVLMLCRAQPFGQLTDEQVIENA

GEFFRDQGRQVYLSRPPACPQGLYELMLRCWSRESEQRPPFSQLHRFLAEDALNTV

FLAG Tag sequence (SEQ ID NO: 40)
DYKDDDDK

DDR1 Discoidin Domain sequence (SEQ ID NO: 41)
CRYALGMQDRTIPDSDISASSSWSDSTAARHSRLESSDGDGAWCPAGSVFPKEEEYLQVD

LQRLHLVALVGTQGRHAGGLGKEFSRSYRLRYSRDGRRWMGWKDRWGQEVISGNEDPEGV

VLKDLGPPMVARLVRFYPRADRVMSVCLRVELYGC

What is claimed is:

1. A method of treating cancer in a subject, comprising administering to the subject a therapeutically effective amount of an antibody that specifically binds to the extracellular domain of human discoidin domain receptor 1 (DDR1), wherein the cancer expresses DDR1 and the antibody comprises:

(a) a heavy chain CDR1 comprising GYTFTDYFMK (SEQ ID NO:22), a heavy chain CDR2 comprising DINPNNGDTFYIQKFKG (SEQ ID NO:23), and a heavy chain CDR3 comprising SRDLAY (SEQ ID NO:24) and (b) a light chain CDR1 comprising KSSQSLLYSNGKTYLN (SEQ ID NO:27), a light chain CDR2 comprising QVSKLDS (SEQ ID NO:28), and a light chain CDR3 comprising VQGTDFPQT (SEQ ID NO:29).

2. The method of claim 1, wherein the antibody comprises a heavy chain variable region having at least 90% sequence identity to SEQ ID NO:33; and a light chain variable region having at least 90% sequence identity to SEQ ID NO:35.

3. The method of claim 1, wherein the antibody comprises a heavy chain variable region comprising SEQ ID NO:33 and a light chain variable region comprising SEQ ID NO:35.

4. The method of claim 1, wherein the antibody is a recombinant antibody, a monoclonal antibody, a chimeric antibody, a humanized antibody, a human antibody, an antibody fragment, a bispecific antibody, a monospecific antibody, a monovalent antibody, an IgG1 antibody, or an IgG2 antibody.

5. The method of claim 1, wherein the antibody:

(i) modulates the activity of DDR1;

(ii) inhibits binding of a ligand to DDR1;

(iii) is an antagonist of DDR1;

(iv) inhibits activation of DDR1; and/or (v) blocks collagen-induced tyrosine phosphorylation of DDR1.

6. The method of claim 1, wherein the cancer is selected from the group consisting of a breast cancer, colorectal cancer, hepatic cancer, renal cancer, lung cancer, pancreatic cancer, melanoma, ovarian cancer, prostate cancer, and head and neck cancer.

7. A method of treating cancer in a subject, comprising administering to the subject a therapeutically effective amount of an antibody that specifically binds to the extracellular domain of human discoidin domain receptor 1 (DDR1), wherein the cancer expresses DDR1 and the antibody competes for specific binding to human DDR1 with a second antibody and wherein the second antibody comprises:

(a) a heavy chain CDR1 comprising GYTFTDYFMK (SEQ ID NO:22), a heavy chain CDR2 comprising DINPNNGDTFYIQKFKG (SEQ ID NO:23), and a heavy chain CDR3 comprising SRDLAY (SEQ ID NO:24); and (b) a light chain CDR1 comprising KSSQSLLYSNGKTYLN (SEQ ID NO:27), a light chain CDR2 comprising QVSKLDS (SEQ ID NO:28), and a light chain CDR3 comprising VQGTDFPQT (SEQ ID NO:29).

8. The method of claim 7, wherein the second antibody is antibody 20M102 which is produced by the hybridoma deposited with ATCC having deposit number PTA-10051.

9. The method of claim 7, wherein the antibody is a recombinant antibody, a monoclonal antibody, a chimeric antibody, a humanized antibody, a human antibody, an antibody fragment, a bispecific antibody, a monospecific antibody, a monovalent antibody, an IgG1 antibody, or an IgG2 antibody.

10. The method of claim 7, wherein the antibody:

(i) modulates the activity of DDR1;

(ii) inhibits binding of a ligand to DDR1;

(iii) is an antagonist of DDR1;

(iv) inhibits activation of DDR1; and/or (v) blocks collagen-induced tyrosine phosphorylation of DDR1.

11. The method of claim 7, further comprising administering at least one additional therapeutic agent to the subject.

12. The method of claim 11, wherein the additional therapeutic agent is a chemotherapeutic agent.

13. The method of claim 7, wherein the antibody is administered in a pharmaceutical composition.

14. The method of claim 7, wherein the cancer is selected from the group consisting of a breast cancer, colorectal cancer, hepatic cancer, renal cancer, lung cancer, pancreatic cancer, melanoma, ovarian cancer, prostate cancer, and head and neck cancer.

15. A method of inhibiting growth of a tumor or a tumor cell, comprising contacting the tumor or tumor cell with an effective amount of an isolated antibody that specifically binds the extracellular domain of human discoidin domain receptor 1 (DDR1), wherein the tumor or tumor cell expresses DDR1 and the antibody comprises:

(a) a heavy chain CDR1 comprising GYTFTDYFMK (SEQ ID NO:22), a heavy chain CDR2 comprising DINPNNGDTFYIQKFKG (SEQ ID NO:23), and a heavy chain CDR3 comprising SRDLAY (SEQ ID NO:24); and (b) a light chain CDR1 comprising KSSQSLLYSNGKTYLN (SEQ ID NO:27), a light chain CDR2 comprising QVSKLDS (SEQ ID NO:28), and a light chain CDR3 comprising VQGTDFPQT (SEQ ID NO:29).

16. The method of claim 15, wherein the antibody comprises a heavy chain variable region having at least 90% sequence identity to SEQ ID NO:33; and a light chain variable region having at least 90% sequence identity to SEQ ID NO:35.

17. A method of inhibiting growth of a tumor or a tumor cell, comprising contacting the tumor or tumor cell with an effective amount of an isolated antibody; wherein the antibody competes for specific binding to human DDR1 with a second antibody, wherein the second antibody comprises:

(a) a heavy chain CDR1 comprising GYTFTDYFMK (SEQ ID NO:22), a heavy chain CDR2 comprising DINPNNGDTFYIQKFKG (SEQ ID NO:23), and a heavy chain CDR3 comprising SRDLAY (SEQ ID NO:24); and (b) a light chain CDR1 comprising KSSQSLLYSNGKTYLN (SEQ ID NO:27), a light chain CDR2 comprising QVSKLDS (SEQ ID NO:28), and a light chain CDR3 comprising VQGTDFPQT (SEQ ID NO:29).

18. The method of claim 15, wherein the antibody binds the same DDR1 epitope as the epitope to which antibody 20M102 binds, wherein the antibody 20M102 is produced by the hybridoma deposited as ATCC deposit number PTA-10051.

19. The method of claim 7, wherein the antibody binds an epitope comprising at least one amino acid in the sequence SASSSWSDSTAAR (SEQ ID NO:30) within DDR1.

20. The method of claim 7, wherein the antibody binds an epitope comprising at least the tryptophan residue (W) of the sequence SASSSWSDSTAAR (SEQ ID NO:30) within DDR1.

21. The method of claim 17, wherein the antibody binds an epitope comprising at least one amino acid in the sequence SASSSWSDSTAAR (SEQ ID NO:30) within DDR1.

22. The method of claim 17, wherein the antibody binds an epitope comprising at least the tryptophan residue (W) of the sequence SASSSWSDSTAAR (SEQ ID NO:30) within DDR1.

* * * * *